US012766123B2

(12) United States Patent
Klopp et al.

(10) Patent No.: US 12,766,123 B2
(45) Date of Patent: *Oct. 20, 2026

(54) COMPOSITIONS OF TRIGLYCERIDES AND USES THEREOF

(71) Applicant: Ultragenyx Pharmaceutical Inc., Novato, CA (US)

(72) Inventors: John Klopp, San Francisco, CA (US); Gabrielle Morris, Novato, CA (US); Emil Kakkis, San Rafael, CA (US); Steven Jungles, Naperville, IL (US)

(73) Assignee: Ultragenyx Pharmaceutical Inc., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/002,217

(22) Filed: Dec. 26, 2024

(65) Prior Publication Data

US 2025/0120934 A1 Apr. 17, 2025

Related U.S. Application Data

(63) Continuation of application No. 18/167,551, filed on Feb. 10, 2023, now Pat. No. 12,551,461, which is a (Continued)

(51) Int. Cl.

*A61K 31/23* (2006.01)

*A61K 9/14* (2006.01)

(Continued)

(52) U.S. Cl.

CPC .............. *A61K 31/23* (2013.01); *A61K 9/143* (2013.01); *A61K 9/146* (2013.01); *A61K 9/1611* (2013.01); *A61K 9/1652* (2013.01); *A61K 31/20* (2013.01)

(58) Field of Classification Search

None

See application file for complete search history.

(56) References Cited

U.S. PATENT DOCUMENTS

| | | |
|---|---|---|
| 3,337,596 A | 8/1967 | Thompson |
| 4,753,963 A | 6/1988 | Jandacek et al. |

(Continued)

FOREIGN PATENT DOCUMENTS

| | | | |
|---|---|---|---|
| CN | 101919453 A | 12/2010 |
| CN | 103079555 A | 5/2013 |

(Continued)

OTHER PUBLICATIONS

Abraham, S. et al., "Weight and Height of Adults 18-74 Years of Age: United States, 1971-74," U.S. Department of Health, Education and Welfare, Data from the National Health Survey, DHEW Publication No. (PHS) 79-1659, National Center for Health Statistics, Vital and Health Statistics, Series 11, No. 211 (May 1979), 56 pages.

(Continued)

*Primary Examiner* — Isis A Ghali

(74) *Attorney, Agent, or Firm* — COOLEY LLP

(57) ABSTRACT

The present invention includes solid compositions of triglycerides with one or more fatty acids, such as triheptanoin and glycerol phenylbutyrate, and therapeutic use thereof. The solid compositions can be prepared by spray-drying or other processes.

9 Claims, 40 Drawing Sheets

Related U.S. Application Data continuation of application No. 16/445,557, filed on Jun. 19, 2019, now abandoned, which is a continuation of application No. 14/419,601, filed as application No. PCT/US2014/065693 on Nov. 14, 2014, now abandoned.

(60) Provisional application No. 61/904,369, filed on Nov. 14, 2013.

(51) Int. Cl.
*A61K 9/16* (2006.01)
*A61K 31/20* (2006.01)

(56) References Cited

U.S. PATENT DOCUMENTS

| | | | |
|---|---|---|---|
| 5,604,119 | A | 2/1997 | Haraldsson et al. |
| 5,746,933 | A | 5/1998 | Ishida et al. |
| 5,885,616 | A | 3/1999 | Hsiao et al. |
| 5,908,631 | A | 6/1999 | Arnaud et al. |
| 5,968,979 | A | 10/1999 | Brusilow |
| 6,228,820 | B1 | 5/2001 | Sakai et al. |
| 6,346,262 | B1 | 2/2002 | Levy |
| 6,465,401 | B1 | 10/2002 | Kodali et al. |
| 8,106,093 | B2 | 1/2012 | Roe |
| 8,404,215 | B1 | 3/2013 | Scharschmidt et al. |
| 8,642,012 | B2 | 2/2014 | Scharschmidt |
| 8,697,748 | B2 | 4/2014 | Roe |
| 12,551,461 | B2 | 2/2026 | Klopp et al. |
| 2002/0137640 | A1 | 9/2002 | Memita et al. |
| 2003/0162833 | A1 | 8/2003 | Roe |
| 2006/0004099 | A1 | 1/2006 | Roe |
| 2007/0123588 | A1 | 5/2007 | Charles |
| 2007/0148746 | A1 | 6/2007 | Schoerken et al. |
| 2008/0090902 | A1 | 4/2008 | Pandey et al. |
| 2009/0017118 | A1 | 1/2009 | Samuelsen et al. |
| 2011/0201558 | A1 | 8/2011 | Roe et al. |
| 2011/0306663 | A1 | 12/2011 | Schiffmann et al. |
| 2012/0231077 | A1 | 9/2012 | Samuelsen et al. |
| 2013/0005818 | A1 | 1/2013 | Roe |
| 2014/0221482 | A1 | 8/2014 | Mochel et al. |
| 2016/0166525 | A1 | 6/2016 | Ischiropoulos et al. |
| 2016/0243071 | A1 | 8/2016 | Klopp et al. |
| 2020/0069631 | A1 | 3/2020 | Klopp et al. |
| 2021/0353581 | A1 | 11/2021 | Mohsen |
| 2023/0181513 | A1 | 6/2023 | Klopp et al. |
| 2025/0120935 | A1 | 4/2025 | Klopp |
| 2025/0120936 | A1 | 4/2025 | Klopp |

FOREIGN PATENT DOCUMENTS

| | | | | |
|---|---|---|---|---|
| EP | 0421581 | A1 | 4/1991 | |
| EP | 2262536 | A2 | 12/2010 | |
| EP | 3300727 | A1 | 4/2018 | |
| EP | 3068383 | B1 | 9/2020 | |
| JP | S5215834 | A | 2/1977 | |
| JP | S63309162 | A | 12/1988 | |
| JP | H03188018 | A | 8/1991 | |
| JP | H0692848 | A | 4/1994 | |
| JP | H06145688 | A | 5/1994 | |
| JP | H06178664 | A | 6/1994 | |
| JP | H0840891 | A | 2/1996 | |
| JP | H08311480 | A | 11/1996 | |
| JP | 2849155 | B2 | 1/1999 | |
| JP | 2002536304 | A | 10/2002 | |
| JP | 2004091524 | A | 3/2004 | |
| JP | 2007505124 | A | 3/2007 | |
| JP | 2007314492 | A | 12/2007 | |
| JP | 2008533048 | A | 8/2008 | |
| JP | 2008537732 | A | 9/2008 | |
| JP | 2009107954 | A | 5/2009 | |
| JP | 2009520005 | A | 5/2009 | |
| JP | 2009525992 | A | 7/2009 | |
| JP | 2010526123 | A | 7/2010 | |
| JP | 2012501451 | A | 1/2012 | |
| JP | 2012180337 | A | 9/2012 | |
| JP | 2013516416 | A | 5/2013 | |
| JP | 2013528648 | A | 7/2013 | |
| JP | 2015510010 | A | 4/2015 | |
| JP | 2016504323 | A | 2/2016 | |
| JP | 2017501972 | A | 1/2017 | |
| JP | 2020111585 | A | 7/2020 | |
| MX | 2007000304 | A | 6/2007 | |
| MX | 2012014520 | A | 3/2013 | |
| WO | WO-0045649 | A1 * | 8/2000 | ............. A23L 33/12 |
| WO | WO-2004022050 | A1 | 3/2004 | |
| WO | WO-2005023233 | A2 | 3/2005 | |
| WO | WO-2005120485 | A1 | 12/2005 | |
| WO | WO-2006014353 | A2 | 2/2006 | |
| WO | WO-2006099325 | A2 | 9/2006 | |
| WO | WO-2006099358 | A2 | 9/2006 | |
| WO | WO-2007080263 | A1 | 7/2007 | |
| WO | WO-2007090408 | A2 | 8/2007 | |
| WO | WO-2007139024 | A1 | 12/2007 | |
| WO | WO-2008099025 | A2 | 8/2008 | |
| WO | WO-2011082111 | A1 | 7/2011 | |
| WO | WO-2011159364 | A1 | 12/2011 | |
| WO | WO-2011159634 | A1 | 12/2011 | |
| WO | WO-2013012699 | A2 | 1/2013 | |
| WO | WO-2013121906 | A1 | 8/2013 | |
| WO | WO-2013126990 | A1 | 9/2013 | |
| WO | WO-2013158616 | A1 | 10/2013 | |
| WO | WO-2014093901 | A1 | 6/2014 | |
| WO | WO-2015073803 | A1 | 5/2015 | |
| WO | WO-2015073816 | A1 | 5/2015 | |

OTHER PUBLICATIONS

Ahuja, S., "Overview: Isolation and Characterization of Impurities," In: Handbook of Isolation and Characterization of Impurities in Pharmaceuticals, Satinder Ahuja and Karen Mills Alsante (Eds.), Separation Science and Technology, vol. 5, 1st ed., Academic Press (Jun. 2003), 25 pages.

Beyer et al., "Quantitative NMR spectroscopy of biologically active substances and excipients," Bioanal Rev., Dec. 2010, vol. 2, pp. 1-22.

Borges, Triheptanoin-A Medium chain with odd chain fatty acids: Anew anaplerotic anticonvulsant treatment?, Epilepsy Res., Jul. 2012, pp. 239-244, vol. 100, No. 3.

Cwik, V. A., "Disorders of Lipid Metabolism in Skeletal Muscle," Metabolic Myopathies, vol. 18, No. 1, Feb. 2000, pp. 167-184.

European Medicines Agency, "ICH Topic Q 3 A (R2), Impurities in new Drug Substances. ICH Step 5. Note for Guidance on Impurities Testing: Impurities in New Drug Substances," Oct. 25, 2006, EMEA 2006, Reference No. CPMP/ICH/2737/99, Retrieved from the Internet: Oct. 17, 2023 from https://www.ich.org/page/quality-guidelines, 15 pages.

European Medicines Agency, "ICH Topic Q 6 A Specifications: Test Procedures and Acceptance Criteria for New Drug Substances and New Drug Products: Chemical Substances. Step 5. Note for Guidance Specifications: Test Procedures and Acceptance Criteria for New Drug Substances and New Drug Products: Chemical Substances (CPMP/ICH/367/96)" May 2000, EMEA 2006, Reference No. CPMP/ICH/367/96, Retrieved from the Internet: Oct. 17, 2023 from https://www.ich.org/page/quality-guidelines, 32 pages.

European Medicines Agency, "ICH Topic Q 6 B Specifications: Test Procedures and Acceptance Criteria for Biotechnological/Biological Products. Step 5. Note for Guidance on Specifications: Test Procedures and Acceptance Criteria for Biotechnological/Biological Products." Sep. 1999, EMEA 2006, Reference No. (CPMP/ICH/365/96), Retrieved from the Internet: Oct. 17, 2023 from https://www.ich.org/page/quality-guidelines, 17 pages.

Extended European Search Report for European Application No. 14861440.7, mailed Oct. 10, 2017, 17 pages.

Extended European Search Report for European Application No. 20196269.3, mailed Jan. 14, 2021, 11 pages.

Extended Partial European Search Report for European Application No. 14861440.7, mailed Jun. 13, 2017, 21 pages.

(56) References Cited

OTHER PUBLICATIONS

Fomon, S. J. et al. , "Body composition of reference children from birth to age 10 years," Am J Clin. Nutr. 35, (May 1982), pp. 1169-1175.
Gillingham, M. et al., "Dietary Management of Long-chain 3-hydroxyacyl-CoA dehydrogenase deficiency (LCHADD). A Case Report and Survey," J Inher. Metab. Dis. (1999), vol. 22, pp. 123-131.
Gillingham, M. et al., "Optimal dietary therapy of long-chain 3-hydroxyacyl-CoA dehydrogenase deficiency," Molecular Genetics and Metabolism, (May 2003), vol. 79, pp. 114-123.
Gillingham, Study of Triheptanoin for Treatment of Long-Chain Fatty Acid Oxidation Disorder (Triheptanoin), [Abstract] U.S. National Library of Medicine, ClinicalTrials.gov Identifier: NCT01379625, 2011, 8 pages.
Hartman, L. et al., "Preparation of Medium Chain Triglycerides with the Use of Physical Refining," European Journal of Lipid Science and Technology (1989), vol. 91, pp. 324-327.
Hasenhuettl, G. L. et al. (eds.), "Analysis of Food Emulsifiers," In: Food Emulsifiers and Their Applications, Springer Science+ Business Media Dordrecht (1997), pp. 39-66.
International Search Report and Written Opinion for International Application No. PCT/US2014/065693, mailed Jan. 30, 2015, 10 pages.
Joyce, P. et al., "The Role of Porous Nanostructure in Controlling Lipase-Mediated Digestion of Lipid Loaded into Silica Particles," Langmuir, Feb. 2014, vol. 30, No. 10, pp. 2779-2788.
Kinman, R. P. et al., "Potential of Triheptanoate Emulsion for the Parenteral and Enteral Treatment of Long-chain Fatty Acid Oxidation Disorders: Metabolic Studies in Normal Rats." Mol. Genet. Metab. (Mar. 2004), vol. 81, pp. 162.
Knuniants, I. L., "Triglyceride," Brief Chemical Encyclopedia, Sovetskaya Encyclopedia, Moscow, 1963, vol. 2, p. 62, 2 pages, with translation of relevant passage "Triglyceride".
Kostecka, M. et al. "Properties and Oxidative Stabilities of Enzymatically Interesterified Chicken Fat and Sunflower Oil Blend", J. Oleo. Sci. 2013. 62(11):893-900.
Madsen et al., "No effect of triheptanoin on exercise performance in McArdle disease" Ann Clin Transl Neurol. Oct. 2019;6(10):1949-1960.
McCarthy et al., "Reference Standards to Support Quality of Synthetic Peptide Therapeutics". Pharm Res. Jun. 2023; 40(6): 1317-1328. Epub Mar. 22, 2023.
Ogilvie, I. et al., "Very long-chain acyl coenzyme A dehydrogenase deficiency presenting with exercise-induced myoglobinuria," Neurology (1994), vol. 44, pp. 467-473.
Rajagopalan, R., "Review of Regulatory Guidance on Impurities," In: Handbook of Isolation and Characterization of Impurities in Pharmaceuticals, Satinder Ahuja and Karen Mills Alsante, Eds., Separation Science and Technology, vol. 5, 1st ed., Academic Press (Jun. 2003), 11 pages.
Rentel et al., "Assay, Purity, and Impurity Profile of Phosphorothioate Oligonucleotide Therapeutics by Ion Pair-HPLC-MS". Nucleic Acid Ther. Jun. 2022; 32(3): 206-220. Epub Mar. 2, 2022.
Roe, C. R. et al., "Carnitine palmitoyltransferase II deficiency: successful anaplerotic diet therapy". Neurology. Jul. 22, 2008; 71(4): 260-264.
Roe, C. R. et al., "Treatment of cardiomyopathy and rhabdomyolysis in long-chain fat oxidation disorders using an anaplerotic odd-chain triglyceride," Journal of Clinical Investigation, 110(2):259-269 (Jul. 2002).
Semak, V. et al., "Synthesis of triheptanoin and formulation as a solid diet for rodents—Supporting Information," WILEY-VCH Verlag Gmbh & Co. KGaA, Weinheim, 2012, 5 pages. DOI: 10.1002/ejlt.201100425.
Semak, V. et al., "Synthesis of triheptanoin and formulation as a solid diet of rodents," Eur. J. Lipid Sci. Technol., Aug. 2012, vol. 114, Issue 8, pp. 889-895.
Semak, V., "Synthesis of 1S-ethyl-4-substituted quinolizidines and other potentially bioactive compounds," Doctoral Thesis, Universitat de Barcelona, 2012, 239 pages.
Traul, K. A. et al., "Review of the Toxicologic Properties of Medium-chain Triglycerides," Food and Chemical Toxicology (2000), vol. 38, pp. 79-98.
Ultragenyx Pharmaceutical Inc., "Ultragenyx Gains Worldwide Rights for Triheptanoin (UX007)", Jul. 2013, Retrieved from the Internet: https://www.globenewswire.com/en/news-release/ 2013/07/11/559492/20739/en/Uitragenyx-Gains-Worldwide-Rights-for-Triheptanoin-UX007.html. Retrieved from the Internet on Mar. 14, 2023, 4 pages.
U.S. Pharmacopeia, Pharmacopeial Forum, vol. 28, No. 4, Jul.-Aug. 2002 at p. 1646, 1,212 pages.
Banfai, B. et al., "Content uniformity and assay requirements in current regulations," Journal of Chromatography A, Jul. 2007, vol. 1156, Issues 1-2, pp. 206-212.
Fuse, T. et al., "Determination of acid values of fats and oils by flow injection analysis with electrochemical detection," Journal of Pharmaceutical and Biomedical Analysis, Jun. 1997, vol. 15, Issues 9-10, pp. 1515-1519.
ASTM International, "Standard Test Method for Acid Value of Fatty Acids and Polymerized Fatty Acids," D 1980-87 (May 1998), 2 pages.
ASTM International, "Standard Test Method for Determination of Free Fatty Acids Contained in Animal, Marine, and Vegetable Fats and Oils Used in Fat Liquors and Stuffing Compounds," D 5555-95 (May 1995), 1 page.
ASTM International, "Standard Test Method for Hydroxyl Value of Fatty Oils and Acids," D 1957-86 (Mar. 1986), 2 pages.
Gu, L. et al., "Parenteral and enteral metabolism of anaplerotic triheptanoin in normal rats. II. Effects on lipolysis, glucose production, and liver acyl-CoA profile," Am J Physiol Endocrinol Metab., vol. 298, No. 2 (Feb. 2010), pp. E362-E371. First published Nov. 10, 2009; doi:10.1152/ajpendo.00384.2009.
International Conference on Harmonisation; Draft Revised Guidance on Impurities in New Drug Substances; Department of Health and Human Services, Food and Drug Administration, Notice, Federal Register, vol. 65, No. 140 (Jul. 2000), pp. 45085-45090.
Kinman, R. P. et al., "Parenteral and enteral metabolism of anaplerotic triheptanoin in normal rats," Am J Physiol Endocrinol Metab., vol. 291, No. 4 (Oct. 2006), pp. E860-E866. First published May 16, 2006; doi:10.1152/ajpendo.00366.2005.
McCue, M. E. et al., "Effect of triheptanoin on muscle metabolism during submaximal exercise in horses," AJVR, vol. 70, No. 8 (Aug. 2009), pp. 1043-1052.
McDonald, T. S. et al., "Alterations of hippocampal glucose metabolism by even versus uneven medium chain triglycerides," Journal of Cerebral Blood Flow & Metabolism, vol. 34, No. 1 (Oct. 2013), 8 pages.
Mochel, F. et al., "Pyruvate carboxylase deficiency: clinical and biochemical response to anaplerotic diet therapy," Molecular Genetics and Metabolism, 84(4):305-312 (Apr. 2005).
Odle, J. et al., "Utilization of Medium-Chain Triglycerides by Neonatal Piglets: II. Effects of Even- and Odd-Chain Triglyceride Consumption over the First 2 Days of Life on Blood Metabolites and Urinary Nitrogen Excretion," Journal of Animal Science, vol. 67, Issue 12 (Dec. 1989), pp. 3340-3351.
Pascual, J. M. et al., "Triheptanoin for Glucose Transporter Type I Deficiency (G1D) Modulation of Human Ictogenesis, Cerebral Metabolic Rate, and Cognitive Indices by a Food Supplement," JAMA Neurol., vol. 71, No. 10, (Aug. 2014), 11 pages.
Roe, C. R. et al., "Adult Polyglucosan Body Disease (APBD): Anaplerotic diet therapy (Triheptanoin) and demonstration of defective methylation pathways," Molecular Genetics and Metabolism, vol. 101 (Jul. 2010) pp. 246-252.
Roe, C. R. et al., "Anaplerotic diet therapy in inherited metabolic disease: Therapeutic potential," J Inherit Metab Dis., vol. 29 (Feb. 2006), pp. 332-340.
Roe, C. R. et al., "Anaplerotic treatment of long-chain fat oxidation disorders with triheptanoin: Review of 15 years Experience," Molecular Genetics and Metabolism, vol. 116 (Oct. 2015) pp. 260-268.

(56) References Cited

OTHER PUBLICATIONS

Saudubray, J. M. et al., "Recognition and management of fatty acid oxidation defects: a series of 107 patients," J Inherit Metab Dis., vol. 22, No. 4 (Jun. 1999), pp. 488-502.
Sucher, K. P., "Medium Chain Triglycerides. A Review of Their Enteral Use in Clinical Nutrition," Nutrition in Clinical Practice, vol. 1, Issue 3 (Jun. 1986), pp. 146-150.
Tefera, T. W. et al., "Triheptanoin Protects Motor Neurons and Delays the Onset of Motor Symptoms in a Mouse Model of Amyotrophic Lateral Sclerosis," PLoS ONE 11(8):e0161816 (Aug. 2016), 24 pages.
Thomas, N. K. et al., "Triheptanoin in acute mouse seizure models," Epilepsy Research, vol. 99, No. 3 (May 2012) pp. 312-317.
Vockley, J. et al., "Long-term major clinical outcomes in patients with long chain fatty acid oxidation disorders before and after transition to triheptanoin treatment A retrospective chart review," Molecular Genetics and Metabolism, vol. 116 (Jun. 2015), pp. 53-60.
Vockley, J. et al., "Triheptanoin treatment in patients with pediatric cardiomyopathy associated with long chain-fatty acid oxidation disorders," vol. 119, Issue 3 (Aug. 2016), 9 pages.
Willis, S. et al., "Anticonvulsant effects of a triheptanoin diet in two mouse chronic seizure models," Neurobiology of Disease, vol. 40 (Aug. 2010), pp. 565-572.
World Health Organization and the Food and Agriculture Organization of the United Nations, "Introduction" and "General conclusions and recommendations of the consultation," Chapter 1 In: Fats and oils in human nutrition, Report of a joint expert consultation, Organized by the Food and Agriculture Organization of the United Nations and the World Health Organization, Rome, Italy, Oct. 19-26, 1993, FAO Food and Nutrition Paper 57 (Oct. 1993), 26 pages.
Zoggeler, T. et al., "Long-term experience with triheptanoin in 12 Austrian patients with long-chain fatty acid oxidation disorders," Orphanet Journal of Rare Diseases, vol. 16, No. 28 (Jan. 2021), 9 pages.
Bruckner, J. et al. (1981), "Studies on the Chemical Properties of Medium Chain Triglycerides and Acetoglycerides," Zeszyty Problemowe Postepow Nauk Rolniczych, vol. 211, pp. 91-98.
Johnson, W., Jr., Cosmetic Ingredient Review Expert Panel (Oct. 2001), "Final Report on the Safety Assessment of Trilaurin, Triarachidin, Tribehenin, Tricaprin, Tricaprylin, Trierucin, Triheptanoin, Triheptylundecanoin, Triisononanoin, Triisopalmitin, Triisostearin, Trilinolein, Trimyristin, Trioctanoin, Triolein, Tripalmitin, Tripalmitolein, Triricinolein, Tristearin, Triundecanoin, Glyceryl Triacetyl Hydroxystearate, Glyceryl Triacetyl Ricinoleate, and Glyceryl Stearate Diacetate," International Journal of Toxicology, vol. 20(Suppl. 4), pp. 61-94.
Da Rocha Ataide, T. et al. (Jun. 2007), "Chemical synthesis of tricaproin, trienantin and tricaprylin," International Journal of Food Science and Technology, vol. 42, Issue 12, pp. 1504-1508.
Da Rocha Ataide, T. et al. (Mar. 2009), "Toxicological Analysis of the Chronic Consumption of Diheptanoin and Triheptanoin in Rats," International Journal of Food Science and Technology, vol. 44, Issue, 3, pp. 484-492.
Gertz, C. et al. (Nov. 2002), "Analysis of acrylamide and mechanisms of its formation in deep-fried products," European Journal of Lipid Science and Technology, vol. 104, Issue 11, pp. 762-771.
Labban, A. K. et al. (Nov. 1991), "Heat Capacity and Thermophysical Properties of n-Heptanoic Acid From 5 to 350 K," Canadian J Chem., vol. 69, Issue 11, pp. 1796-1803.
List, G. R. et al. (Jul. 2005), "Storage Handling, and Transport of Oils and Fats," Chap. 4 In: Bailey's Industrial Oil and Fat Products, F. Shahidi, Ed., Sixth Edition, John Wiley & Sons, Inc. pp. 191-229.
Mahajan, S. S. et al. (Dec. 2004), "Aroma Compounds in Sweet Whey Powder," Journal of Dairy Science, vol. 87, pp. 4057-4063.
Marchis, D. et al. (Jun. 2013), "A Monitoring Study of Glyceroltriheptanoate (GTH) in Animal By-products Through a Validated GC-MS Analytical Method," Food Control, vol. 34, pp. 624-629.
U.S. Department of Health and Human Services, Food and Drug Administration (Aug. 2006), Guidance for Industry, "Q3B(R2) Impurities in New Drug Products," Revision 3, Retrieved from the Internet: https://www.fda.gov/media/71733/download, 18 pages.
U.S. Department of Health and Human Services, Food and Drug Administration (Jun. 2008), Guidance for Industry, "Q3A Impurities in New Drug Substances," Revision 2, Retrieved from the Internet: https://www.fda.gov/media/71727/download, 17 pages.
U.S. Department of Health and Human Services, Food and Drug Administration (Nov. 2003), Guidance for Industry, "Q1A(R2) Stability Testing of New Drug Substances and Products," Revision 2, Retrieved from the Internet: https://www.fda.gov/media/71707/download, 25 pages.
Wakelyn, P. J. et al. (2006), "Solvent Extraction to Obtain Edible Oil Products," Chap. 5 In: Handbook of Functional Lipids, Functional Foods and Nutraceuticals Series, C.C. Akoh (Ed.), CRC Press, Taylor & Francis Group, Boca Raton, Copyright Year: 2006, pp. 89-131.
Waterman, K. C. et al. (Jun. 2003), "Impurities in Drug Products," Chap. 4 In: Handbook of Isolation and Characterization of Impurities in Pharmaceuticals, S. Ahuja (Ed.), Academic Press, pp. 75-88.
Wilhelm, H. M. et al. (Feb. 2011), "Aging Markers for In-Service Natural Ester-Based Insulating Fluids," IEEE Transactions on Dielectrics and Electrical Insulation, vol. 18, No. 3, pp. 714-719.

* cited by examiner

B-Hydroxybutyric Acid (C4-OH) and B-Hydroxyvaleric Acid (C5-OH) Metabolite PK Following Triheptanoin Powder Oil Dosing on Day 1 in Male and Female Mini-pigs Combined Glutamic Acid Metabolite PK Following Triheptanoin Powder and Powder-ER Dosing (Fold Change Relative to Oil Dosing) on Days 1 and 7 in Male and Female Mini-pigs

COMPOSITIONS OF TRIGLYCERIDES AND USES THEREOF

CROSS-REFERENCE TO RELATED APPLICATION

This application is a Continuation of U.S. application Ser. No. 18/167,551, filed on Feb. 10, 2023, which is a Continuation of U.S. application Ser. No. 16/445,557, filed on Jun. 19, 2019, which is a Continuation of U.S. application Ser. No. 14/419,601, filed on Feb. 4, 2015, which is a U.S. National Stage Application of International Application No. PCT/US2014/065693, filed on Nov. 14, 2014, which claims the benefit of U.S. Provisional Patent Application No. 61/904,369 filed Nov. 14, 2013, the contents of each of which are herein incorporated by reference in their entirety for all purposes.

FIELD OF THE INVENTION

The present invention relates to solid compositions of triglycerides with one or more fatty acids, such as triheptanoin and glycerol phenylbutyrate, and the therapeutic use thereof.

BACKGROUND OF THE INVENTION

Current dosage form of the triglycerides drug, e.g., triheptanoin, is a liquid with the consistency of oil. Several problems are associated with the liquid dosage form due to its physical and physiological properties. First, the liquid dosage forms, such as oil, are difficult to be administered due to low miscibility with food or drinks. Second, the oil formulations are difficult to be handled, carried, and dispensed. Furthermore, upon administration, the oil composition is hydrolyzed and released rapidly in the stomach leading to gastric upset, gastric retention, and likely gastrin-related stomach spasm and emesis. In addition, the oil formulations can cause diarrhea by reforming oil droplets and causing a mineral-oil like excess lubrication. Upon repetitive administration of the oil, some patients experience gastric stress which causes vomiting and/or diarrhea. Thus, the tolerability in the oil form can be a dose-limiting toxicity or lead to adverse effects, and the reduced administrable dose would negatively impact the treatment effect for a fatty acid oxidation disorder or deficiency (FAOD); adult polyglucosan body disease; a mitochondrial fat oxidation defect; a glycogen storage disease; a mitochondrial myopathy; glucose transporter type 1 (GLUT1) deficiency syndrome, or other related diseases.

SUMMARY OF THE INVENTION

Among other things, the present invention is directed to a solid composition comprising an ester derived from a polyol and one or more fatty acids as an active ingredient, and a solid substance. To give an example of the ester, triglycerides with one or more fatty acids are suitable for use in accordance with the present invention.

In one aspect, the present invention provides a solid composition comprising triglycerides with one or more odd-numbered carbon fatty acids as an active ingredient and a solid substance; wherein the active ingredient has purity greater than 98% and the one or more odd-numbered carbon fatty acids are selected from the group consisting of C5, C7, C9, C11, C13, C15, and any combinations thereof; and the solid composition comprises at least about 50% by weight the triglycerides. The present invention also provides a solid composition comprising a plurality of solid particles, each particle comprising triglycerides with one or more odd-numbered carbon fatty acids as an active ingredient adsorbed onto a solid substance; wherein the active ingredient has purity greater than 98% and the one or more odd-numbered carbon fatty acids are selected from the group consisting of C5, C7, C9, C11, C13, C15, and any combinations thereof; and the solid composition comprises at least about 50% by weight the triglycerides.

In another aspect, the present invention provides a solid composition comprising triglycerides with one or more phenylalkanoic acids and/or phenylalkenoic acids as an active ingredient and a solid substance; wherein the active ingredient has purity greater than 95% and the solid composition comprises at least about 50% by weight the triglycerides. The present invention also provides a solid composition comprising a plurality of solid particles, each particle comprising triglycerides with one or more phenylalkanoic acids and/or phenylalkenoic acids as an active ingredient adsorbed onto a solid substance; wherein the active ingredient has purity greater than 95% and the solid composition comprises at least about 50% by weight the triglycerides.

In some embodiments, the solid composition comprises at least about 50%, about 55%, about 60%, about 65%, about 70%, about 75%, about 80%, about 85%, or about 90% of the active ingredient by weight of the composition.

In some embodiments, the solid substance includes a solid carrier. The solid carrier can be a fumed silica. Additionally or alternatively, the solid carrier can be selected from the group consisting of $SiO_2$, $TiO_2$, $Al_2O_3$, zeolites, Cab-O-Sil, and combinations thereof.

The solid substance can further comprise one or more sustained release polymers.

In some embodiments, the sustained release polymer is a film-forming, water insoluble polymer. The film-forming, water insoluble polymer can be selected from the group consisting of ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly (phenyl methacrylate), poly(methyl acrylate), poly(isopropyl acrylate), poly(isobutyl acrylate), poly(octadecyl acrylate), poly(ethylene), poly(ethylene) low density, poly (ethylene) high density, poly(propylene), poly(ethylene oxide), poly(ethylene terephthalate), poly(vinyl isobutyl ether), poly(vinyl acetate), poly(vinyl chloride) or polyurethane, or mixtures thereof. In one embodiment, the film-forming, water insoluble polymer is cellulose acetate.

In some embodiments, the sustained release polymer comprises one or more pH dependent polymers. The pH dependent polymer can be selected from a group consisting of a methyl acrylate-methacrylic acid copolymer, a cellulose acetate succinate, a hydroxy propyl methyl cellulose phthalate, a hydroxy propyl methyl cellulose acetate succinate (hypromellose acetate succinate), a polyvinyl acetate phthalate (PVAP), a methyl methacrylate-methacrylic acid copolymer, alginate and stearic acid, and any combinations thereof.

In some embodiments, the solid composition comprises, by weight of the composition, about 50% to about 80% of the active ingredient; about 10% to about 30% of the solid carrier; and about 10% to about 30% of the sustained release polymer. In some embodiments, the active ingredient, the solid carrier, and the sustained release polymer are in a weight ratio of about 2:1:1.

The solid composition in accordance with the present invention can be in form of a powder. In some embodiments, the powder comprises particles having an average diameter of less than about 10 micron. The particles can have an average diameter of less than about 9 microns, less than about 8 microns, less than about 7 microns, less than about 6 microns, less than about 5 microns, less than about 4 microns, less than about 3 microns, less than about 2 microns, less than about 1000 nm, less than about 900 nm, less than about 800 run, less than about 700 nm, less than about 600 nm, less than about 500 nm, less than about 400 nm, less than about 300 nm, less than about 290 nm, less than about 280 nm, less than about 270 nm, less than about 260 nm, less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, less than about 50 nm, less than about 40 nm, less than about 30 nm, less than about 20 nm, less than about 10 nm, less than about 9 nm, less than about 8 nm, less than about 7 nm, less than about 6 nm, or less than about 5 nm.

In some embodiments, the solid substance has a surface area of at least 20 $m^2/g$.

In some embodiments, the solid particles are formed by spray drying a spray suspension comprising the triglycerides with one or more odd-numbered carbon fatty acids as an active ingredient and the solid substance.

The solid composition in accordance with the present invention can include triglycerides with seven carbon fatty acids. In some embodiments, the solid composition further comprises triglycerides with one or more odd-numbered carbon fatty acids selected from the group consisting of C5, C9, C11, C13, C15, and any combinations thereof.

In some embodiments, the triglycerides is a triheptanoin oil comprising greater than about 98% pure glycerol triheptanoate as an active ingredient. The triheptanoin oil can comprise less than 1% w/w of a non-C7 triglyceride or a combination of non-C7 triglycerides.

The solid composition in accordance with the present invention can further include a pharmaceutically acceptable excipient.

In some embodiments, the solid composition includes an active ingredient that has purity greater than 97% after about four weeks of exposure to about 25° C. at about 60% relative humidity when package in a sealed container. In some embodiments, the solid composition has a water content of no more than 1.0% by weight after about four weeks of exposure to about 25° C. at about 60% relative humidity when package in a sealed container. In some embodiments, the solid composition includes an active ingredient that has purity greater than 98% after about four weeks of exposure to about 25° C. at about 60% relative humidity when package in a sealed container. In some embodiments, the solid composition has a water content of no more than 0.5% by weight after about four weeks of exposure to about 25° C. at about 60% relative humidity when package in a sealed container. In some embodiments, the solid composition includes an active ingredient that has purity greater than 99% after about four weeks of exposure to about 25° C. at about 60% relative humidity when package in a sealed container. In some embodiments, the solid composition has a water content of no more than 0.35% by weight after about four weeks of exposure to about 25° C. at about 60% relative humidity when package in a sealed container.

In some embodiments, the solid composition includes an active ingredient that has purity greater than 97% after about four weeks of exposure to about 40° C. at about 75% relative humidity when package in a sealed container. In some embodiments, the solid composition has a water content of no more than 1.0% by weight after about four weeks of exposure to 40° C. at about 75% relative humidity when package in a sealed container. In some embodiments, the solid composition includes an active ingredient that has purity greater than 98% after about four weeks of exposure to about 40° C. at about 75% relative humidity when package in a sealed container. In some embodiments, the solid composition has a water content of no more than 0.5% by weight after about four weeks of exposure to 40° C. at about 75% relative humidity when package in a sealed container. In some embodiments, the solid composition includes an active ingredient that has purity greater than 99% after about four weeks of exposure to about 40° C. at about 75% relative humidity when package in a sealed container. In some embodiments, the solid composition has a water content of no more than 0.45% by weight after about four weeks of exposure to 40° C. at about 75% relative humidity when package in a sealed container.

The present invention provides a method of treating a disease, disorder, or condition in a subject comprising orally administering to the subject a therapeutically effective amount of a solid composition in accordance with the present invention, wherein the disease, disorder, or condition is selected from any one or more of the following: a fatty acid oxidation disorder or deficiency; adult polyglucosan body disease; a mitochondrial fat oxidation defect (e.g., relating to carnitine palmitoyl transferase I, carnitine palmitoyl transferase II, carnitine acylcarnitine translocase, very long chain acyl-CoA dehydrogenase, trifunctional protein, long chain hydroxyacyl-CoA dehydrogenase, multiple acyl-CoA dehydrogenase, short chain acyl CoA dehydrogenase, alpha glucosidase, brancher enzyme, debrancher enzyme, myophosphorylase, or phosphofructokinase); a glycogen storage disease (e.g., glycogen storage disease Type II); glucose transporter type 1 (GLUT1) deficiency syndrome; and a mitochondrial myopathy.

Also provided is a method of treating a disease, disorder, or condition in a subject comprising orally administering to the subject a therapeutically effective amount of a solid composition in accordance with the present invention, wherein the disease, disorder, or condition is selected from any one or more of the following: urea cycle disorders (UCD) and hepatic encephalopathy (HE).

In some embodiments, the solid composition is co-administered with a food, drink, or comestible composition.

DETAILED DESCRIPTION OF THE INVENTION

Figure 1:
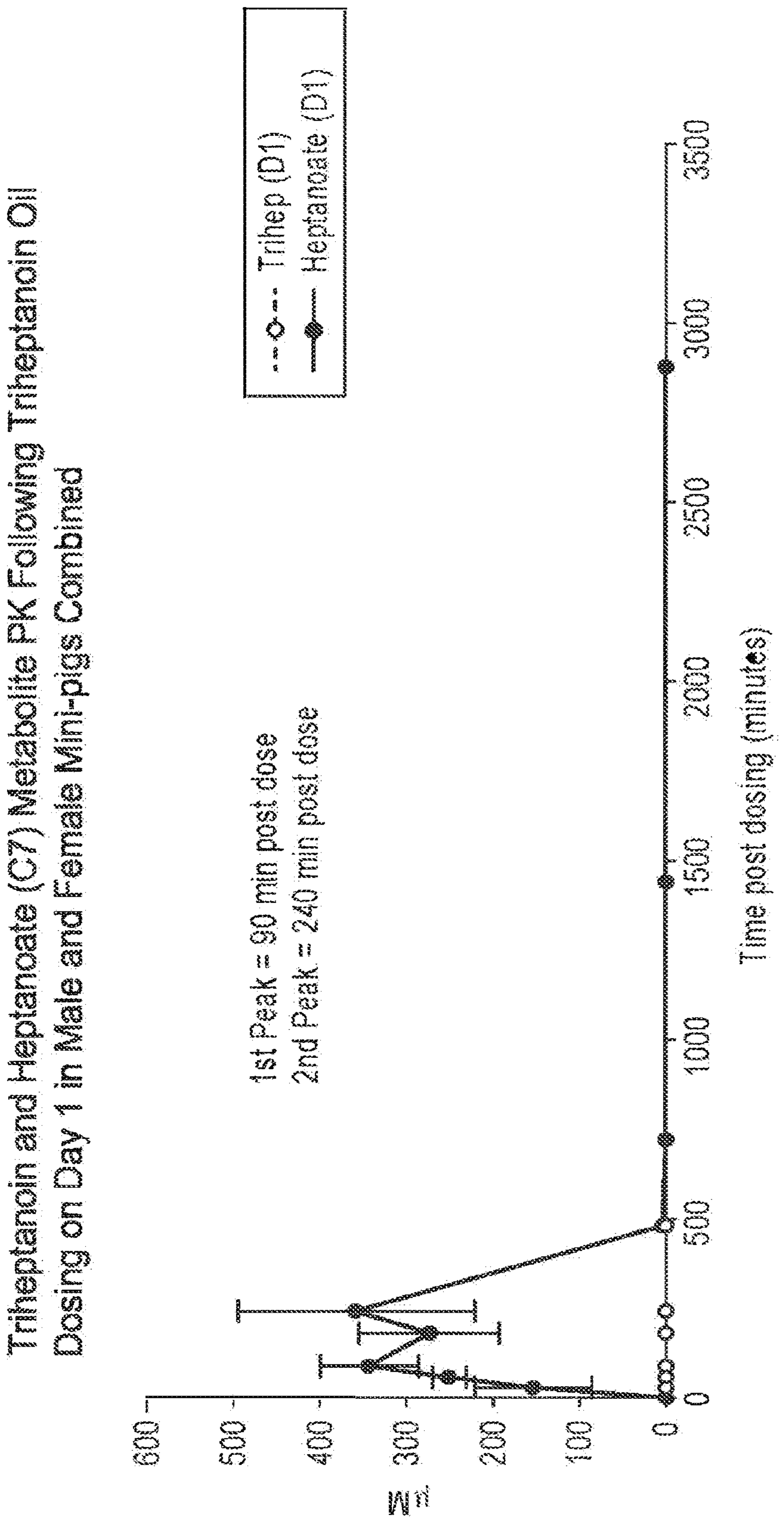
FIG. 1 is the metabolite pharmacokinetics (PK) profile of triheptanoin and heptanoate following triheptanoin oil dosing on Day 1 in male and female mini-pigs combined.
Figure 2:
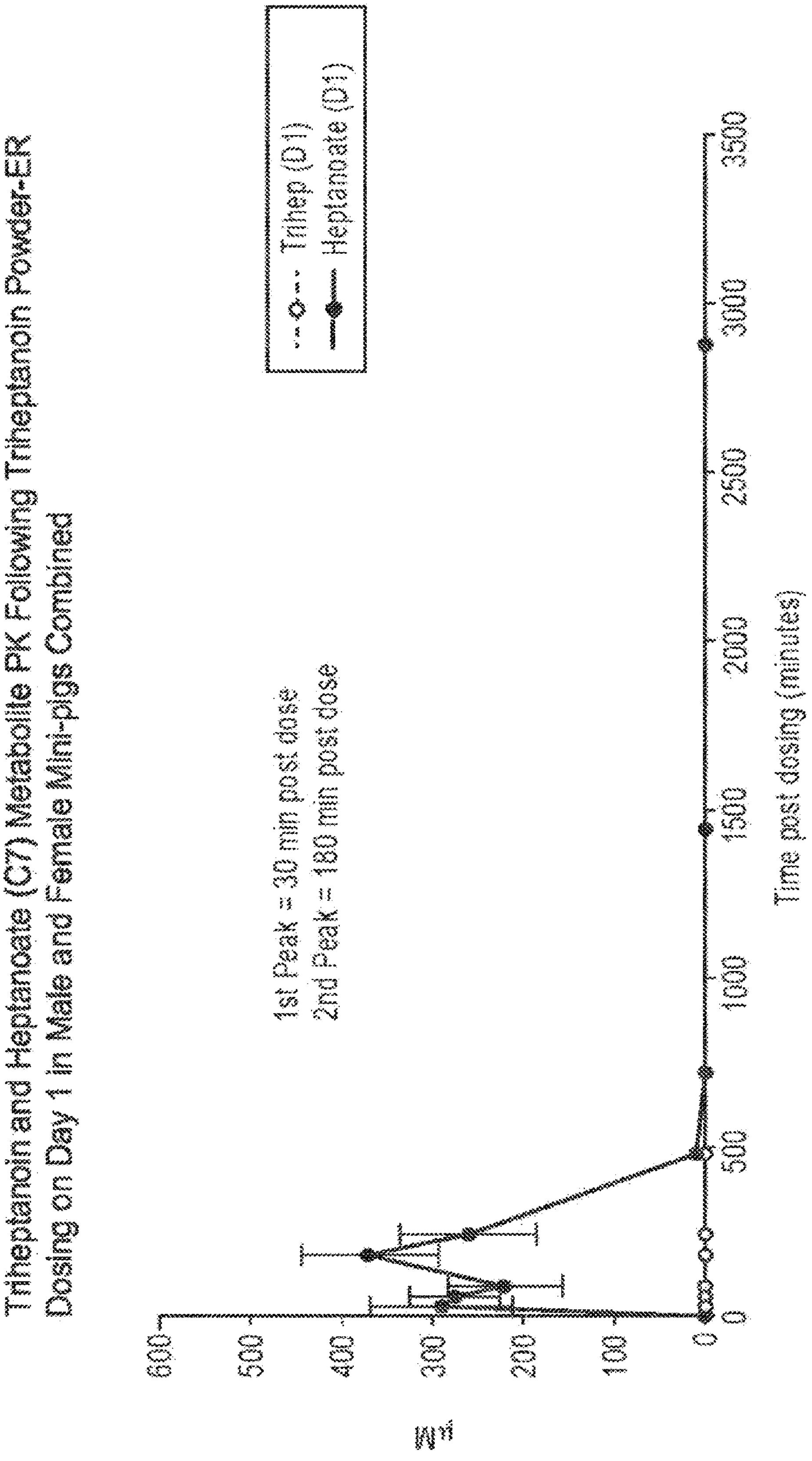
FIG. 2 is the metabolite PK profile of triheptanoin and heptanoate following triheptanoin powder-ER dosing on Day 1 in male and female mini-pigs combined.
Figure 3:
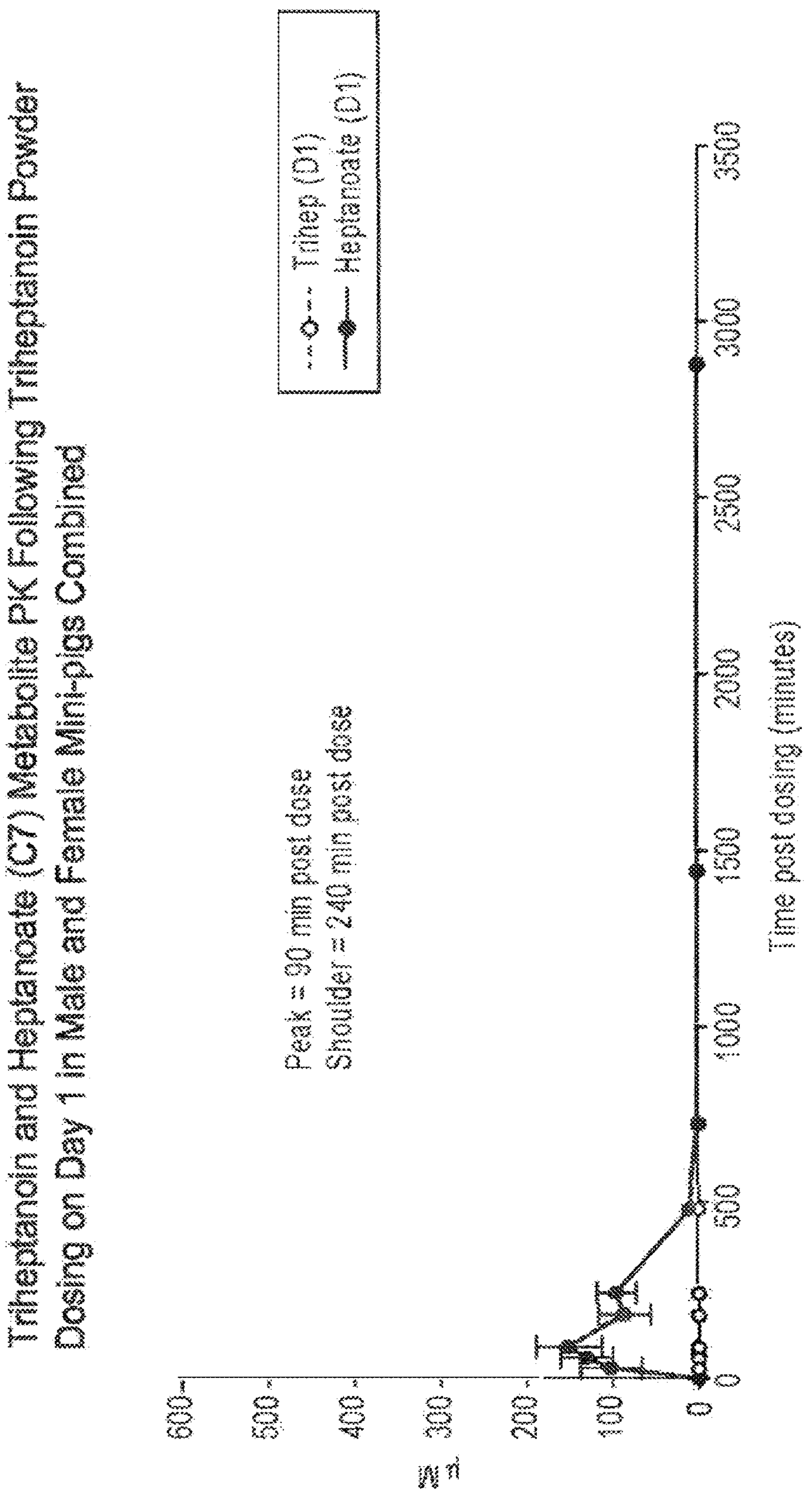
FIG. 3 is the metabolite PK profile of triheptanoin and heptanoate following triheptanoin powder dosing on Day 1 in male and female mini-pigs combined.
Figure 4:
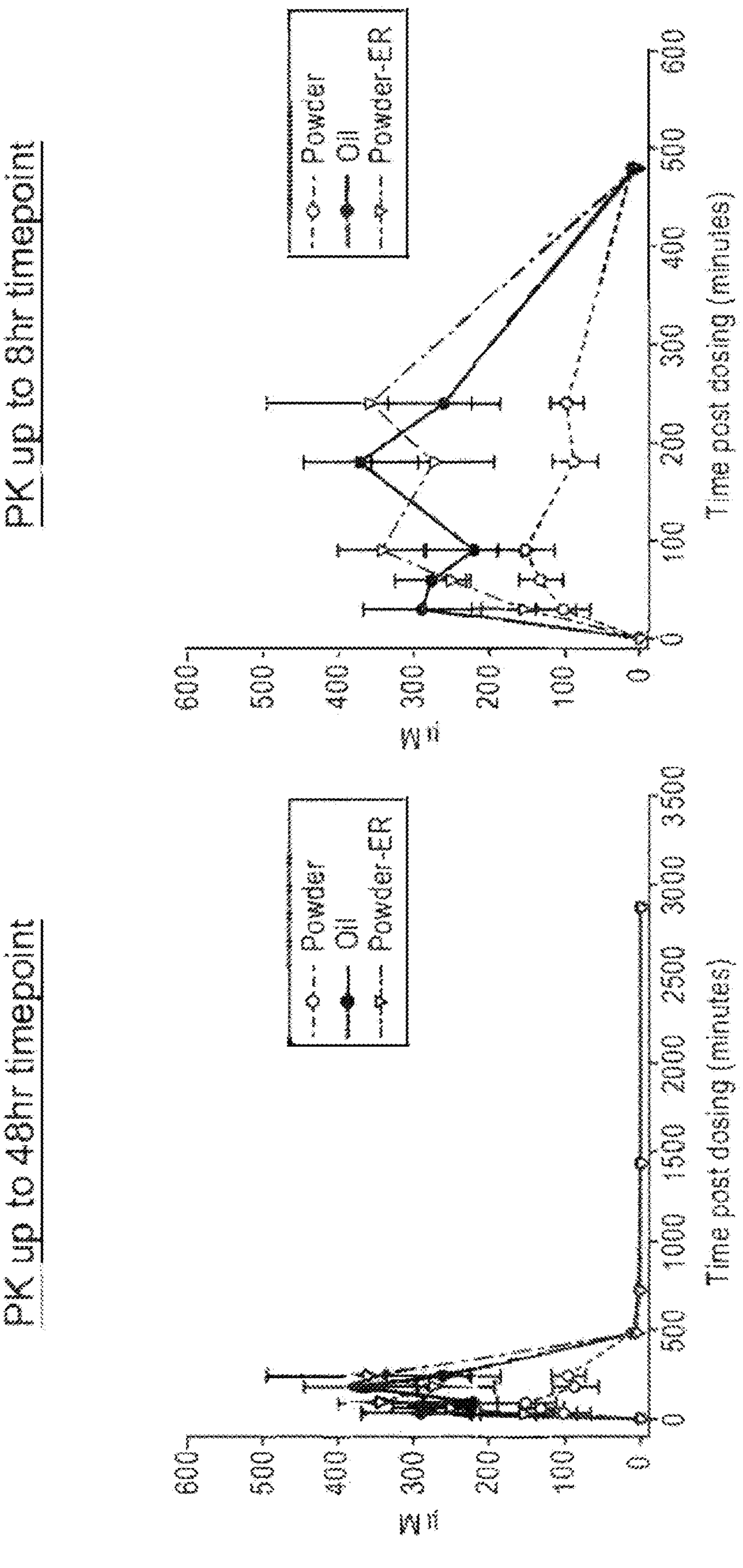
FIG. 4 is the metabolite PK profile up to 48 hours (left) or 8 hours (right) of heptanoate following triheptanoin oil, powder and powder-ER dosing on Day 1 in male and female mini-pigs combined. Heptanoate (C7) metabolite PK following triheptanoin oil, powder and powder-ER dosing on Day 1 in male and female mini-pigs combined.
Figure 5:
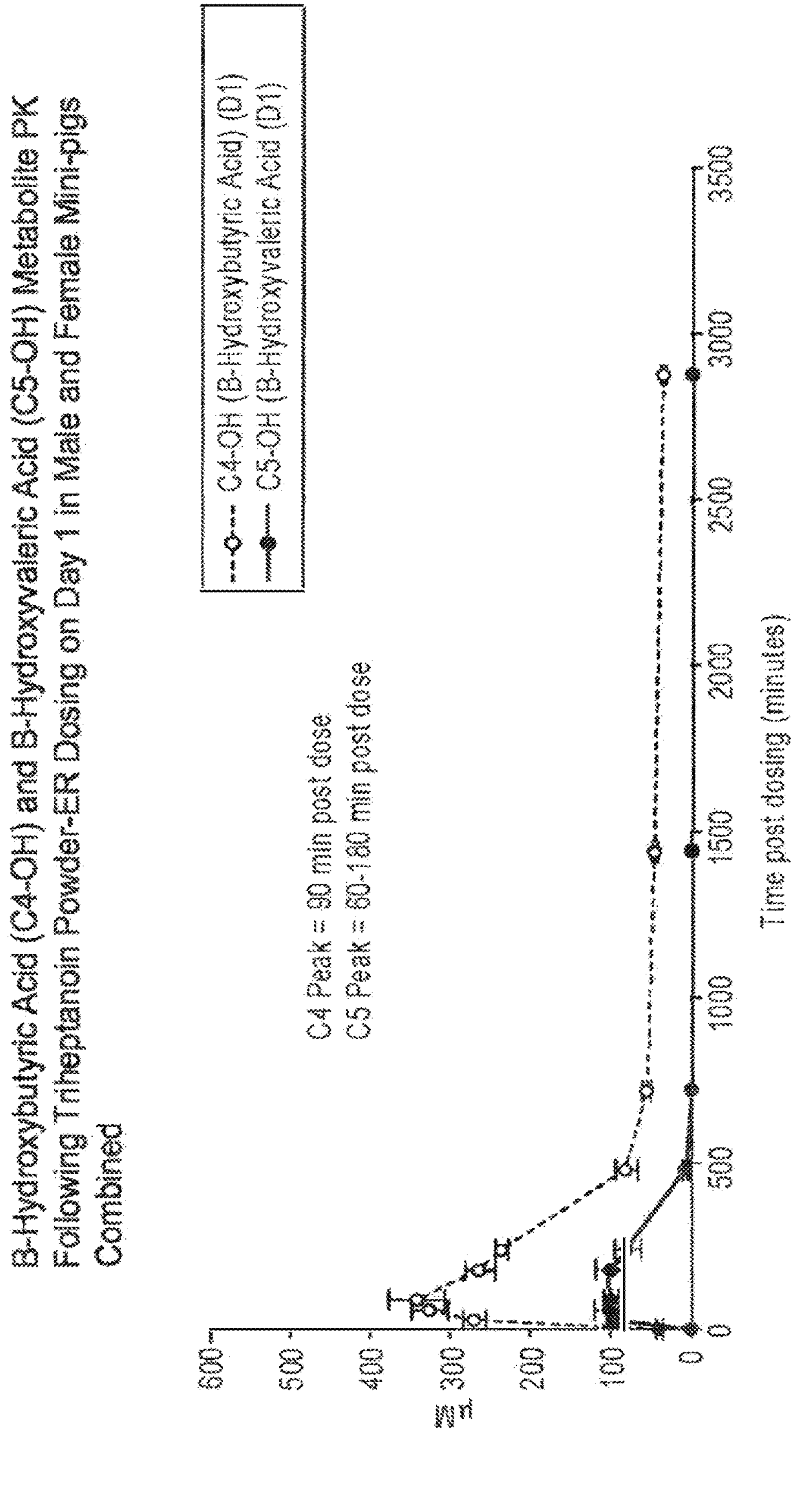
FIG. 5 is the metabolite PK profile of B-hydroxybutyric acid (C4-OH) and B-hydroxyvaleric acid (C5-OH) following triheptanoin powder-ER dosing on Day 1 in male and female mini-pigs combined.
Figure 6:
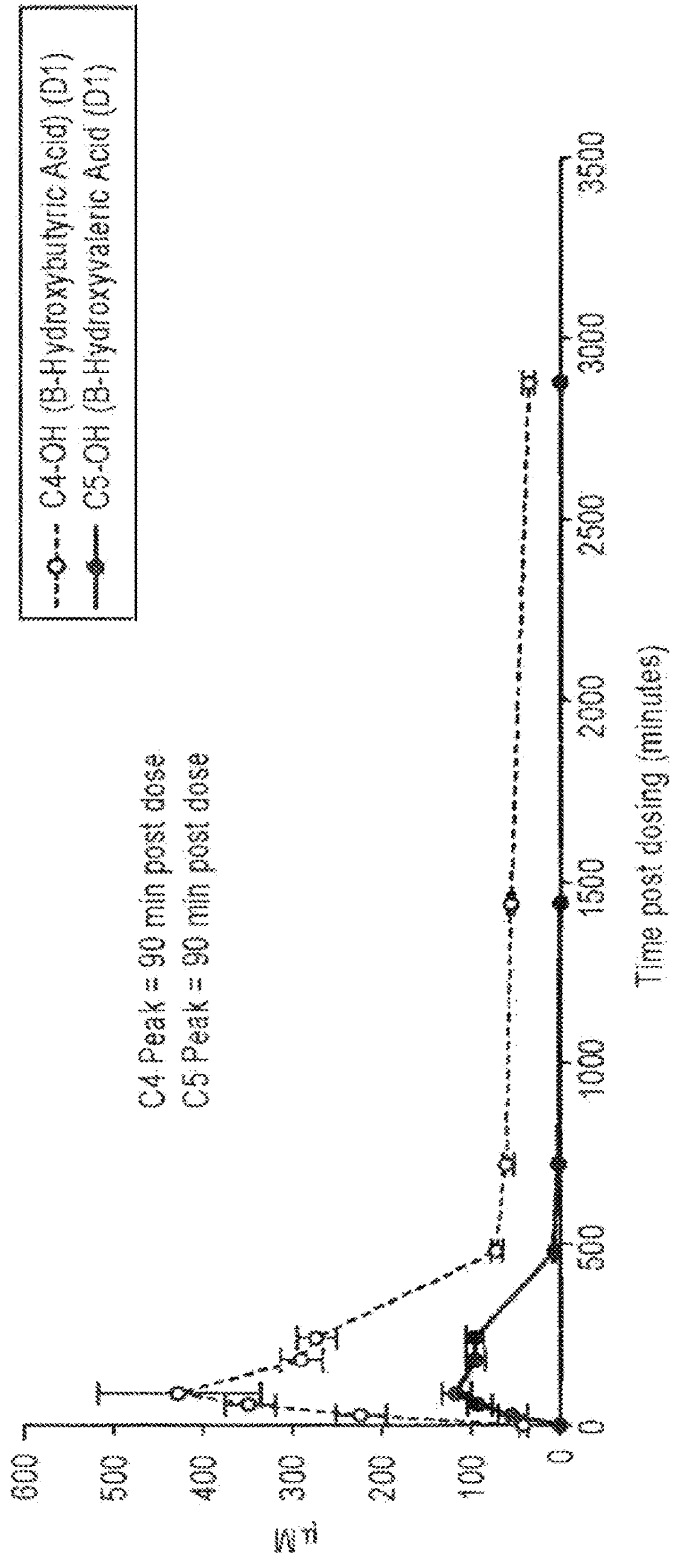
FIG. 6 is the metabolite PK profile of B-hydroxybutyric acid (C4-OH) and B-hydroxyvaleric acid (C5-OH) following triheptanoin oil dosing on Day 1 in male and female mini-pigs combined.
Figure 7:
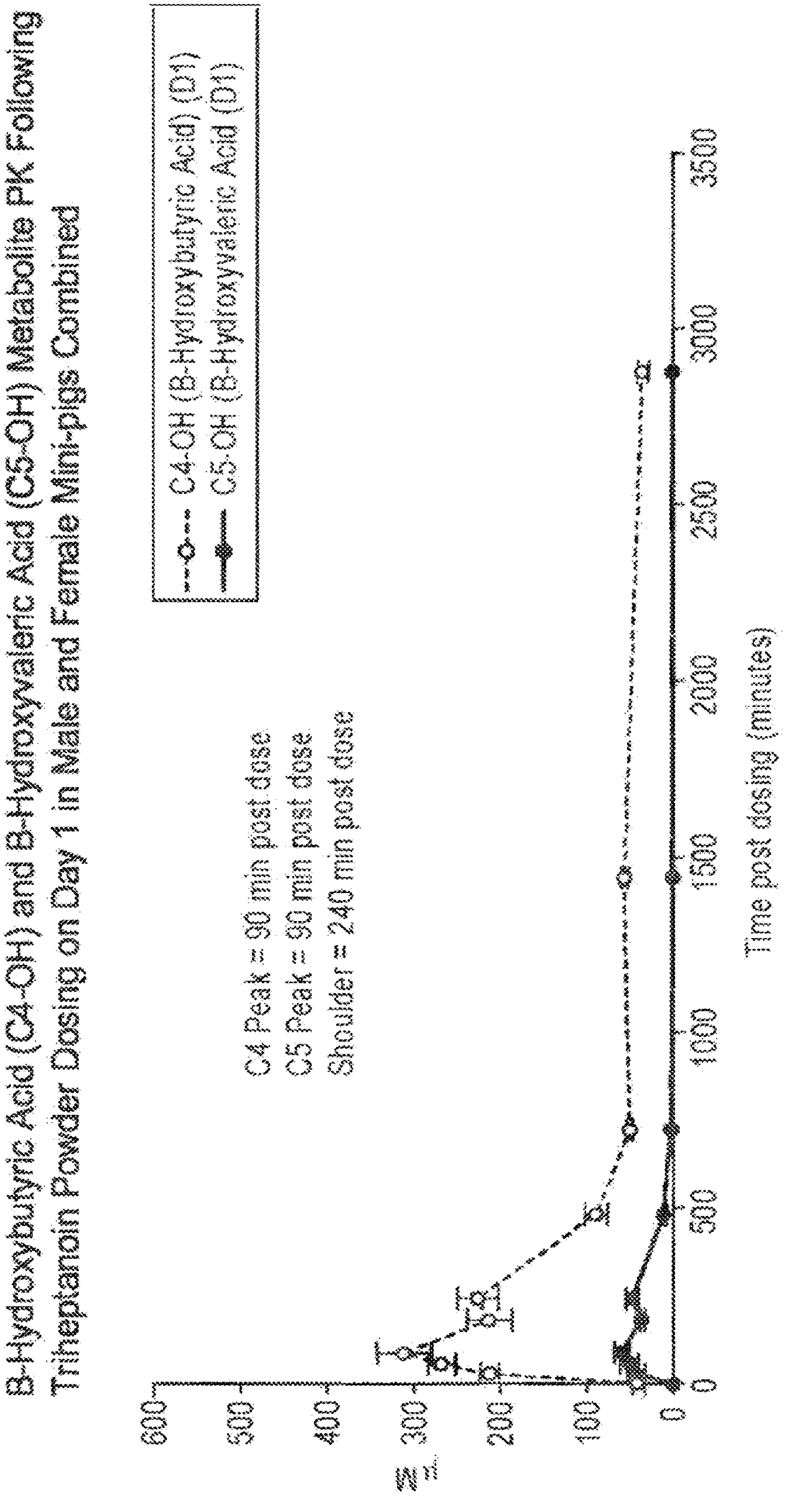
FIG. 7 is the metabolite PK profile of B-hydroxybutyric acid (C4-OH) and B-hydroxyvaleric acid (C5-OH) following triheptanoin powder dosing on Day 1 in male and female mini-pigs combined.
Figure 8:
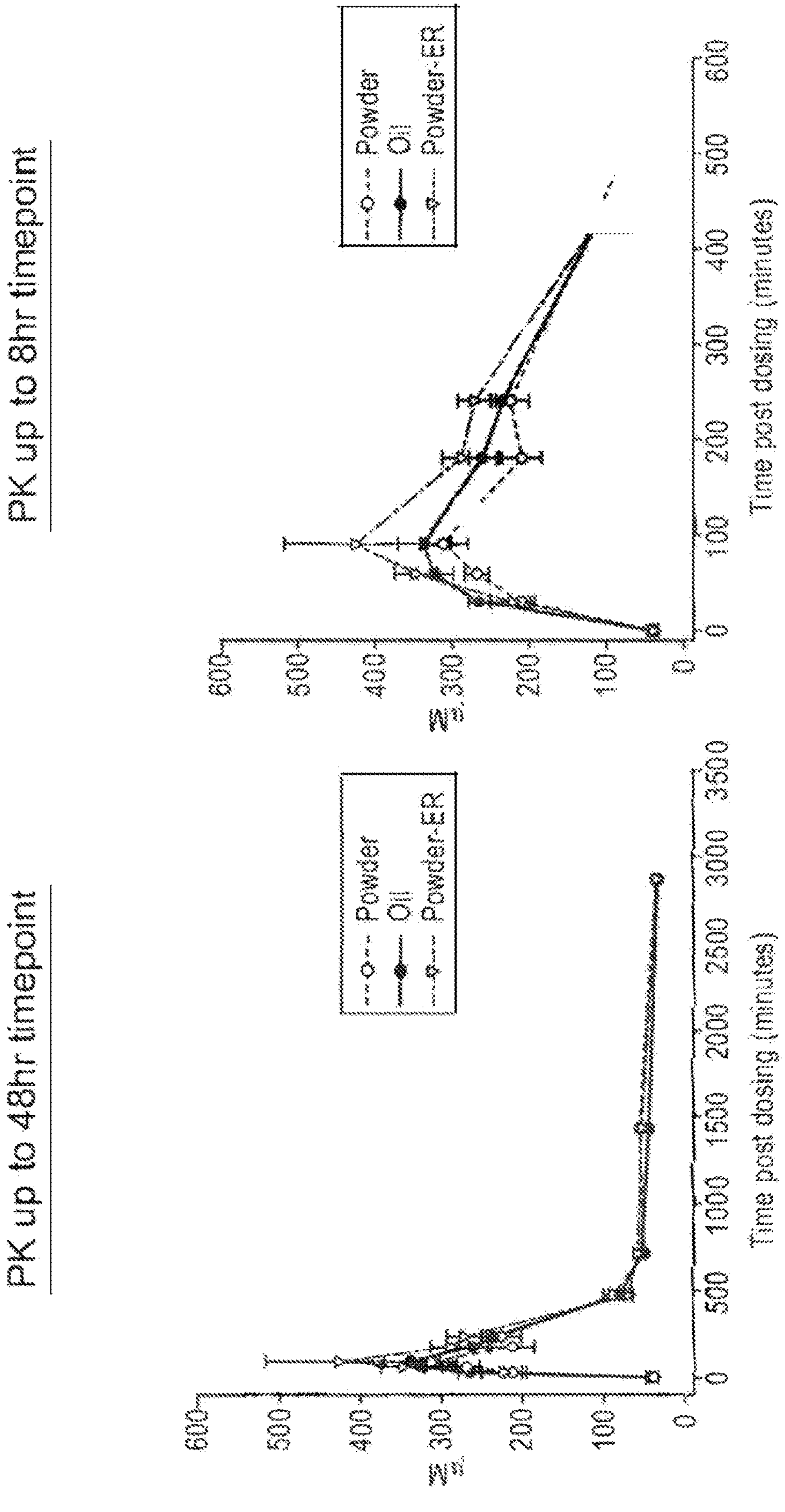
FIG. 8 is the metabolite PK profile up to 48 hours (left) or 8 hours (right) of B-hydroxybutyric acid (C4-OH) following triheptanoin oil, powder and powder-ER dosing on Day 1 in male and female mini-pigs combined. B-Hydroxybutyric acid (C4-OH) metabolite PK following triheptanoin oil, powder and powder-ER dosing on Day 1 in male and female mini-pigs combined.
Figure 9:
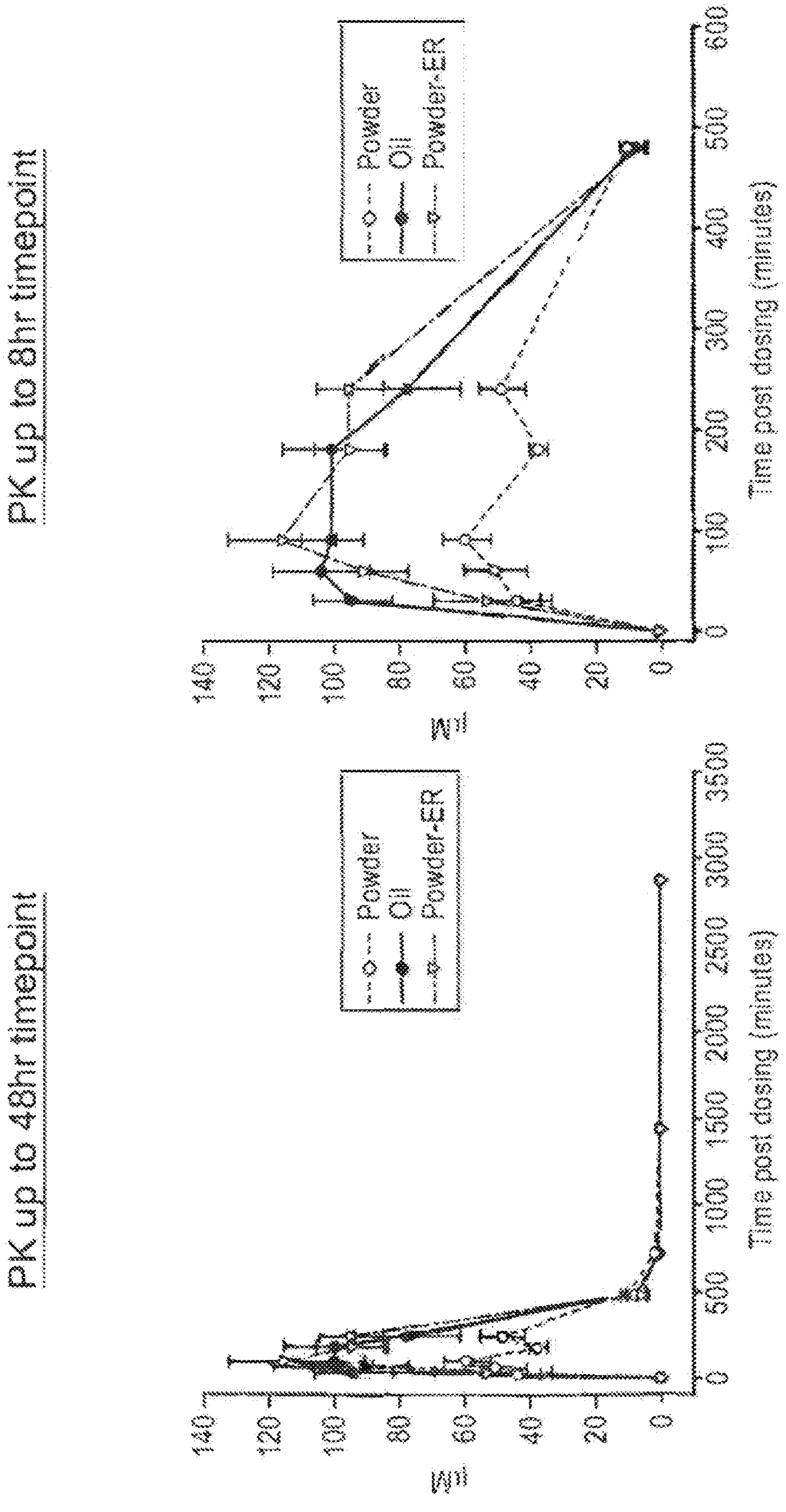
FIG. 9 is the metabolite PK profile up to 48 hours (left) or 8 hours (right) of B-hydroxyvaleric acid (C5-OH) following triheptanoin oil, powder and powder-ER dosing on Day 1 in male and female mini-pigs combined. B-Hydroxyvaleric acid (C5-OH) metabolite PK following triheptanoin oil, powder and powder-ER dosing on Day 1 in male and female mini-pigs combined.

A solid composition in accordance with the present invention comprises an ester derived from a polyol and one or more fatty acids as an active ingredient, and a solid substance. The term "polyol" denotes an alcohol containing two or more hydroxyl groups. Examples of polyols include, but are not limited to, diol (e.g., ethylene glycol, propylene glycol, and resorcinol), triol (e.g., glycerol and ethane-1,1,2-triol), tetraol (e.g., pentaerythritol), and sugar alcohols (e.g., maltitol, sorbitol, xylitol, and erythritol,). In one embodiment, the polyol is glycerol.

In one embodiment, the present solid compositions are particularly useful as pharmaceutical formulation with both improved physical properties and physiological properties. In one embodiment, the solid compositions are easier to be administered because they are miscible with food, drink, or other comestible compositions with ease. In another embodiment, the solid compositions, such as powder or granule dosage forms, are more portable and easier to handle and dispense during regular daily use or while traveling. In another embodiment, the solid compositions are more stable during storage and easier to be handled and transported during manufacture and commercialization. In another embodiment, the solid compositions may have masked taste and improve dose tolerability and reduce side effects. In another embodiment, the solid compositions, e.g., the powder dosage forms, have delayed release characteristics in the stomach, with limited gastric upset, distress, or spasms. In another embodiment, the solid compositions do not cause diarrhea from the oil leading to excess lubrication of the GI tract through its delayed release and stabilized physical presence allowing better and more complete digestion during passage in the gastrointestinal tract. In another embodiment, the solid compositions comprising a plurality of particles wherein the active ingredient oil is adsorbed on the surface of solid substance thereby enhancing the surface area of the oil on substrate particles. Such enhanced surface area of the oil can enhance absorption efficiency for each dose thereby improving efficacy and reducing diarrhea at the same time. In one embodiment, the solid composition can reduce the gastric stress and other side effects, enhance the therapeutic effect, and improve patient compliance. In another embodiment, the solid composition can reduce gastric and diarrheal tolerability issues, allow higher daily doses of triheptanoin to be achieved and allow for better, and more complete digestion and absorption via the suspended stabilized particles in the GI tract with high surface area.

Triglycerides Solid Compositions

In the present invention, "triglyceride" refers to an ester derived from glycerol and one or more fatty acids. The fatty acids can have a carbon chain that is optionally substituted alkyl, optionally substituted alkenyl, or optionally substituted aryl.

"Alkyl," by itself or as part of another substituent, refers to a saturated branched, straight-chain or cyclic monovalent hydrocarbon radical derived by the removal of one hydrogen atom from a single carbon atom of a parent alkane. The term "alkyl" includes "cycloakyl" as defined herein below. Typical alkyl groups include, but are not limited to, methyl; ethyl; propyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl) or 1 to 4 carbon atoms ($C_1$-$C_4$ alkyl). $C_1$-$C_6$ alkyl is also known as "lower alkyl".

"Alkenyl," by itself or as part of another substituent, refers to an unsaturated branched, straight-chain or cyclic monovalent hydrocarbon radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, an alkenyl group comprises from 2 to 20 carbon atoms ($C_2$-$C_{20}$ alkenyl). In other embodiments, an alkenyl group comprises from 2 to 10 carbon atoms ($C_2$-$C_{10}$ alkenyl). In still other embodiments, an alkenyl group comprises from 2 to 6 carbon atoms ($C_2$-$C_6$ alkenyl) or 2 to 4 carbon atoms ($C_2$-$C_4$ alkenyl). $C_2$-$C_6$ alkenyl is also known as "lower alkenyl".

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 10 carbon atoms ($C_6$-$C_{10}$ aryl). In a specific embodiment, an aryl group comprises a phenyl group.

The term "substituted" specifically envisions and allows for one or more substitutions that are common in the art. However, it is generally understood by those skilled in the art that the substituents should be selected so as to not adversely affect the useful characteristics of the compound or adversely interfere with its function. Suitable substituents may include, for example, halogen groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, arylalkyl or heteroarylalkyl groups, arylalkoxy or heteroarylalkoxy groups, amino groups, alkyl- and dialkylamino groups, carbamoyl groups, alkylcarbonyl groups, carboxyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, cycloalkyl groups, cyano groups, $C_1$-$C_6$ alkylthio groups, arylthio groups, nitro groups, keto groups, acyl groups, boronate or boronyl groups, phosphate or phosphonyl groups, sulfamyl groups, sulfonyl groups, sulfinyl groups, and combinations thereof. In the case of substituted combinations, such as "substituted arylalkyl," either the aryl or the alkyl group may be substituted, or both the aryl and the alkyl groups may be substituted with one or more substituents. Additionally, in some cases, suitable substituents may combine to form one or more rings as known to those of skill in the art.

The term "optionally substituted" denotes the presence or absence of the substituent group(s). That is, it means "substituted or unsubstituted". For example, optionally substituted alkyl includes both unsubstituted alkyl and substituted alkyl. The substituents used to substitute a specified group can be further substituted, typically with one or more of the same or different groups selected from the various groups specified above.

In some embodiments, the triglyceride is an ester derived from glycerol and three fatty acids independently selected from the odd-numbered carbon fatty acids of C5, C7, C9, C11, C13, and C15. In some embodiments, the triglyceride is an ester derived from glycerol and three fatty acids independently selected from phenylalkanoic acids and phenylalkenoic acids.

The present invention is based, in part, on the discovery that triglycerides with one or more odd-numbered carbon fatty acids, such as C5, C7, C9, C11, C13, C15, and any combinations thereof, having a purity greater than food grade can be formulated with a solid substance to form a solid composition. In one embodiment, the solid composition contains at least about 50% by weight the triglycerides, which can be in either solid or oil form prior to being formulated with the solid substance. In one embodiment, the triglycerides are an oil prior to being formulated with the solid substance to form the solid composition.

In one embodiment, the present invention provides a solid composition comprising triglycerides with one or more odd-numbered carbon fatty acids as an active ingredient and a solid substance; wherein the active ingredient has purity greater than 98% and the one or more odd-numbered carbon fatty acids are selected from the group consisting of C5, C7, C9, C11, C13, C15, and any combinations thereof; and the solid composition comprises at least about 50% by weight the triglycerides. In one embodiment, the triglyceride is an ester derived from glycerol and three fatty acids independently selected from the odd-numbered carbon fatty acids of C5, C7, C9, C11, C13, and C15. In one specific embodiment, the triglyceride is an ester derived from glycerol and three C7 fatty acids, i.e., triheptanoin. In one embodiment, the solid composition comprises triglycerides with seven carbon fatty acids. In another embodiment, the solid composition further comprises triglycerides with one or more odd-numbered carbon fatty acids selected from the group consisting of C5, C9, C11, C13, C15, and any combinations thereof. In another embodiment, the triglycerides with seven carbon fatty acids is a triheptanoin oil comprising greater than about 98% pure glycerol triheptanoate as an active ingredient.

In some embodiment, the present invention provides a solid composition comprising triglycerides with one or more phenylalkanoic acids and/or phenylalkenoic acids as an active ingredient and a solid substance; wherein the active ingredient has purity greater than 95% and the solid composition comprises at least about 50% by weight the triglycerides. In one embodiment, the triglyceride is an ester derived from glycerol and three fatty acids independently selected from phenylalkanoic acids and phenylalkenoic acids. In one embodiment, the triglyceride is a compound of formula (I):

(I)

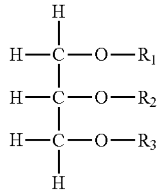

wherein $R_1$, $R_2$, and $R_3$ are independently H,

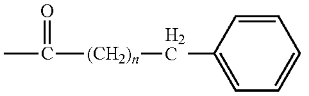

or

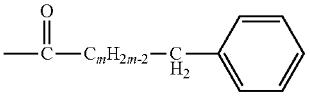

, and n is zero or an even number from 2-24 and m is an even number from 2-24, provided that at least one of $R_1$, $R_2$, and $R_3$ is other than H. In one embodiment, n and m are an even number from 2 to 24. In one embodiment, n and m are 0, 2, 4, or 6. In one specific embodiment, the triglyceride is an ester derived from glycerol and three phenylbutyrate, i.e., glycerol phenylbutyrate (e.g., RAVICTI®). Examples of triglycerides with one or more phenylalkanoic acids and/or phenylalkenoic acids are further described in U.S. Pat. No. 5,968,979, the contents of which are hereby incorporated by reference in entirety for all purpose.

In one embodiment, the solid composition comprises at least about 50%, about 55%, about 60%, about 65%, about 70%, about 75%, about 80%, about 85%, or about 90% of the triglycerides. In another embodiment, the solid composition comprises at least about 55%, about 60%, about 65%, about 70%, about 75%, about 80%, or about 85% of the triglycerides. In one specific embodiment, the solid composition comprises about 60% of the triglycerides. In one specific embodiment, the solid composition comprises about 75%, about 80%, or about 85% of the triglycerides.

In some embodiments, the active ingredient in the solid composition has a purity of about or at least about 95, 95.5, 96, 96.5, 97, 97.5, 97.6, 97.7, 97.8, 97.9, 98, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, or 99.9% or more, or any range derivable therein.

In one embodiment, the solid composition is in a powder form which comprises a plurality of particles, and each particle comprises triglycerides with one or more odd-numbered carbon fatty acids as an active ingredient adsorbed onto a solid substance. In one embodiment, the solid substance has a surface area of at least 20 $m^2/g$.

In one embodiment, the solid substance comprises a solid carrier. The term "solid carrier", as used herein, denotes any pharmaceutically acceptable solid material, which has a high surface area and does not adversely interact with the present triglycerides. By "high surface area", it is meant that the solid carrier has a surface area of at least 20 $m^2/g$, or at least 30 $m^2/g$, or at least 50 $m^2/g$, or at least 70 $m^2/g$, or at least 100 $m^2/g$, or at least 150 $m^2/g$, or at least 180 $m^2/g$. In one embodiment, the solid carrier can have surface areas of up to 200 $m^2/g$, up to 400 $m^2/g$, or up to 600 $m^2/g$, or more. The surface area of the substrate can be measured using standard procedures, such as low-temperature nitrogen adsorption, based on the Brunauer, Emmett, and Teller (BET) method, which is well known in the art.

In one embodiment, the particles have an average diameter of less than about 100 micron. In one embodiment, the particles have an average diameter of less than about 90 micron, less than about 80 microns, less than about 70 microns, less than about 60 microns, less than about 50 microns, less than about 40 microns, less than about 30 microns, less than about 20 microns, or less than about 10 microns. In another embodiment, the particles have an average diameter of less than about 9 microns, less than about 8 microns, less than about 7 microns, less than about 6 microns, less than about 5 microns, less than about 4 microns, less than about 3 microns, less than about 2 microns, less than about 1000 nm, less than about 900 nm, less than about 800 run, less than about 700 nm, less than about 600 nm, less than about 500 nm, less than about 400 nm, less than about 300 nm, less than about 290 nm, less than about 280 nm, less than about 270 nm, less than about 260 nm, less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, less than about 50 nm, less than about 40 nm, less than about 30 nm, less than about 20 nm, less than about 10 nm, less than about 9 nm, less than about 8 nm, less than about 7 nm, less than about 6 nm, or less than about 5 nm. The powder may first be formed in the form of small particles ranging in size of from about 5 nm to about 1 micron, or from about 10 nm to about 50 nm, or from about 20 nm to about 100 nm. These particles may in turn form agglomerates ranging in size from about 10 nm to about 100 micron, or 20 nm to about 100 micron, or about 50 nm to about 100 micron.

Examples of the solid carrier include fumed silica and inorganic oxides, such as $SiO_2$, $TiO_2$, $ZnO_2$, ZnO, $Al_2O_3$, MgAlSilicate, CaSilicate, $Al(OH)_2$, zeolites, and other inorganic molecular sieves; water insoluble polymers, such as cross-linked cellulose acetate phthalate, cross-linked hydroxypropyl methyl cellulose acetate succinate, cross-linked polyvinyl pyrrolidinone, (also known as cross povidone) microcrystalline cellulose, polyethylene/polyvinyl alcohol copolymer, polyethylene polyvinyl pyrrolidone copolymer, cross-linked carboxymethyl cellulose, sodium starch glycolate, cross-linked polystyrene divinyl benzene; and activated carbons, including those made by carbonization of polymers such as polyimides, polyacylonitrile, phenolic resins, cellulose acetate, regenerated cellulose, and rayon. In some specific embodiments, the solid carrier can be Cab-O-Sil, Neusilin, hypromellose acetate succinate (HPMCAS), Casein, or combinations thereof. In one embodiment, the solid carrier is fumed silica. Suitable fumed silica are availble from any major producers under various brand names, such as are Evonik (who sells it under the name Aerosil), Cabot Corporation (Cab-O-Sil), Wacker Chemie (HDK), Dow Corning, and OCI (Konasil).

In one embodiment, the solid substance further comprises one or more sustained release polymer. In one embodiment, the one or more sustained release polymer comprises one or more pH dependent polymers. In one embodiment, the pH dependent polymer is selected from a group consisting of a methyl acrylate-methacrylic acid copolymer, a cellulose acetate succinate, a hydroxy propyl methyl cellulose phthalate, a hydroxy propyl methyl cellulose acetate succinate (hypromellose acetate succinate), a polyvinyl acetate phthalate (PVAP), a methyl methacrylate-methacrylic acid copolymer, alginate and stearic acid, and any combinations thereof.

In one embodiment, the solid composition may further comprise one or more additional pharmaceutically acceptable excipient, such as fillers, surfactants, and flavorants. Those excipients can be added to improve the powder flowability, dissolvability, and taste.

"Pharmaceutically acceptable" refers to being suitable for use in contact with the tissues of humans and animals without undue toxicity, irritation, allergic response, and the like, commensurate with a reasonable benefit/risk ratio, and effective for their intended use within the scope of sound medical judgment. "Excipient" denotes a diluent, adjuvant, vehicle or carrier with which the active ingredient is administered. Examples of the pharmaceutically acceptable excipient include, are not limited to a filler (or diluent), a binder, a disintegrant, a lubricant, or a combination thereof.

Fillers may be one or more compounds which are capable of providing compactability and good flow. Examples of fillers include microcrystalline cellulose, starch, lactose, sucrose, glucose, mannitol, maltodextrin, sorbitol, dextrose, silicic acid, dibasic calcium phosphate, or a combination comprising at least one of the foregoing fillers. Exemplary lactose forms include lactose monohydrate, NF (Fast Flo), lactose spray-dried monohydrate, and lactose anhydrous. Exemplary microcrystalline celluloses (MCC) include, for example, AVICEL® PH101 and AVICEL® PH102, which are commercially available from FMC Biopolymer, Philadelphia, PA.

Binders may be used to impart cohesive qualities to a formulation, for example, a tablet formulation, and thus ensure that the tablet remains intact after compaction. Examples of binders include starches (for example, Starch 1500® or pregelatinized starch), alignates, gelatin, carboxymethylcellulose, sugars (for example, sucrose, glucose, dextrose, and maltodextrin), polyethylene glycol, waxes, natural and synthetic gums, polyvinylpyrrolidone, and cellulosic polymers (for example, microcrystalline cellulose, hydroxypropyl cellulose, hydroxypropyl methylcellulose, methyl cellulose, and hydroxyethyl cellulose) and combinations comprising one or more of the foregoing binders.

Disintegrants are used to facilitate disintegration or "breakup" of a composition, for example, a tablet, after administration. Examples of disintegrants include sodium starch glycolate, sodium croscarmellose (cross-linked carboxy methyl cellulose), crosslinked polyvinylpyrrolidone (PVP-XL), anhydrous calcium hydrogen phosphate, agar-agar, potato or tapioca starch, alginic acid, or a combination comprising one or more of the foregoing disintegrants.

A lubricant may be added to the composition for a minimum period of time to obtain good dispersal. Examples of lubricants include magnesium stearate, calcium stearate, zinc stearate, stearic acid, talc, glyceryl behenate, polyethylene glycol, polyethylene glycol, polyethylene oxide, sodium lauryl sulfate, magnesium lauryl sulfate, sodium oleate, sodium stearyl fumarate, DL-leucine, colloidal silica, or a combination comprising one or more of the foregoing lubricants.

If desired, the solid composition may optionally comprise small amounts of nontoxic auxiliary substances such as wetting or emulsifying agents, or pH buffering agents, for example, sodium acetate, sorbitan monolaurate, triethanolamine sodium acetate, triethanolamine oleate, sodium lauryl sulfate, dioctyl sodium sulfosuccinate, and polyoxyethylene sorbitan fatty acid esters.

In another embodiment of the present invention, the solid composition comprises one or more sustained release polymer. In one embodiment, the solid substance comprises one or more sustained release polymer. By "sustained release polymer", it is meant any polymer which can control the release of the active ingredient from the composition in such a way to obtain the desired release profile. In one embodiment, the sustained release polymer is a hydrophilic polymer. The term "hydrophilic polymer" refers to a polymer having a strong affinity for water and tending to dissolve in, mix with, or be wetted by water. Examples of the hydrophilic polymer include, but are not limited to polyethylene oxide, hydroxypropyl cellulose, hydroxypropyl methyl hydroxyethyl cellulose, cellulose, sodium carboxymethylcellulose, calcium carboxymethyl cellulose, methyl cellulose, polyacrylic acid, maltodextrin, pre-gelatinized starch, guar gum, sodium alginate, polyvinyl alcohol, chitosan, locust bean gum, amylase, any other water-swelling polymer, and a combination thereof. In another embodiment, the sustained release polymer is a film-forming, water insoluble polymer. Examples of the film-forming, water insoluble polymer include, but are not limited to ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate), poly(ethylene), poly (ethylene) low density, poly(ethylene) high density, poly (propylene), poly(ethylene oxide), poly(ethylene terephthalate), poly(vinyl isobutyl ether), poly(vinyl acetate), poly(vinyl chloride) or polyurethane, or any other water insoluble polymer, or mixtures thereof. In another embodiment, the sustained release polymer is a film-forming, water soluble polymer. Examples of the film-forming, water soluble polymer include, but are not limited to polyvinyl alcohol, polyvinylpyrrolidone, methyl cellulose, hydroxypropyl cellulose, hydroxypropylmethyl cellulose and polyethylene glycol, Pluronic F108, Pluronic F127, Pluronic F68 or mixtures thereof. In one embodiment, the present solid composition comprises one or more the film-forming, water insoluble polymers. In one specific embodiment, the present solid composition comprises cellulose acetate.

In another embodiment, the sustained release polymer comprises one or more pH dependent polymers. By "pH dependent polymers", it is meant polymers which are not soluble at the highly acidic pH but soluble in neutral to basic pH environment. Examples of pH dependent polymers include, but are not limited to, methyl acrylate-methacrylic acid copolymers, cellulose acetate succinates, hydroxy propyl methyl cellulose phthalates, hydroxy propyl methyl cellulose acetate succinates (hypromellose acetate succinates), polyvinyl acetate phthalates (PVAP), methyl methacrylate-methacrylic acid copolymers, alginate and stearic acid, and any combinations thereof. Furthermore, materials, such as fatty acids, waxes, shellac, plastics, and plant fibers, may also be suitable for pH dependent polymers.

The solid compositions as described herein can be used alone for various purposes, such as in treatment methods as described herein. In this regard, the solid compositions can be pharmaceutically acceptable.

The present solid compositions can be formed by a spray-drying process. In one embodiment, the solid particles are formed by spray drying a spray suspension comprising the triglycerides with one or more odd-numbered carbon fatty acids as an active ingredient and the solid substance. The spray suspension contains the triglycerides dissolved in a solvent and the solid substance suspended therein. Such spray suspension is spray-dried to form a solid powder by rapidly removing the solvent. The formed powder particles may have the triglycerides adsorbed on the surface of the solid substance or the triglycerides and the solid substance interspersed with one another to form a matrix. In another embodiment, the solid composition further comprises a sustained release polymer. For example, the solid particles may be formed by spray drying a spray suspension comprising the triglycerides and the sustained release polymer dissolved in a solvent with the solid substance suspended therein. The spray suspension is spray-dried to form a solid powder by rapidly removing the solvent.

In one embodiment, some powder formulations (with 75%, 80%, 85%, and 90% loading of triheptanoin on solid carrier) were prepared. The triheptanoin oil as described herein was first dissolved in acetone and then mixed with the solid carrier, such as Cab-O-Sil, to form a suspension. The sustained release polymer, e.g., Eudragit, was optionally added. The resulting suspension was spray dried to obtain a powder. The spray dried powder is then dried further to reduce the amount of solvent (acetone) to a desirable level.

Triheptanoin Oil

In one embodiment, the triglyceride in the present solid composition is a triheptanoin oil. Triheptanoin oil as described herein comprises triglycerides with seven carbon fatty acids. Triheptanoin, also known as glycerol triheptanoate, glycerol trienanthate, glyceryl triheptanoate, 1,3-di(heptanoyloxy)propan-2-yl heptanoate, trienanthin, 1,2,3-trienanthoylglycerol, and propane-1,2,3-triyl triheptanoate, is a triglyceride of the seven carbon (C7) fatty acid heptanoate (CAS Registry No. 620-67-7) and has the following structure:

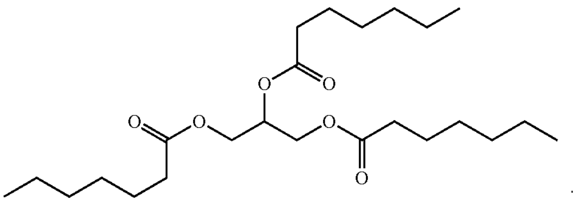 [SMILES: CCCCCCC(=O)OCC(COC(=O)CCCCCC)OC(=O)CCCCCC]

Triheptanoin oil as described herein is of a purity or grade greater than food grade triheptanoin oil. In some embodiments, the triheptanoin oil is considered ultrapure pharmaceutical grade triheptanoin oil.

In one embodiment, the present triheptanoin oil has the general properties listed in Table 1:

| Physical and chemical property | Triheptanoin with Pharmaceutical Grade Purity |
|---|---|
| Form | Liquid |
| Color | Light yellow |
| Cloud point | <0° C. |
| Flash point | ca. 220° C. |
| Vapor pressure | <0.01 hPa; 20° C. |
| Relative Density | ca. 0.96 g/cm$^3$; 20° C. |
| Water solubility | <0.01 g/l; 20° C. |
| Partition coefficient (n-octanol/water) | Log Pow: >3.0; glycerides of saturated $C_7$ fatty acid |
| Viscosity, dynamic | ca. 20 mPa · s at 20° C. |
| Refractive Index | 1.4440 to 1.4465 |

Typically, the total concentration of impurities in triheptanoin oil is less than the total concentration of impurities in food grade triheptanoin oil. In some embodiments, food grade triheptanoin oil can have a purity of about or at most about 95, 95.5, 96, 96.5, 97, or 97.5%, or any range derivable therein.

In some embodiments, total impurities in triheptanoin oil amount to less than 5% w/w. In some embodiments, total impurities in triheptanoin oil amount to less than 5, 4.5, 4, 3.5, 3, 2.5, 2, 1.5, 1, or 0.5% w/w or less, or any range derivable therein.

In one embodiment, triheptanoin oil comprises less than 2% w/w of triglycerides esterified with acids other than C7 acids (e.g., C2, C3, C4, C5, C6, C8, or C9 acids, or others, or combinations thereof ("non-C7 triglycerides")). In some embodiments, triheptanoin oil comprises less than 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2 or 0.1% w/w or less of non-C7 triglycerides, or any range derivable therein.

In one embodiment, triheptanoin oil comprises glycerol triheptanoate of a purity of greater than 97.5%. In some embodiments, triheptanoin oil comprises glycerol triheptanoate of a purity of about or at least about 97.5, 97.6, 97.7, 97.8, 97.9, 98, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8, or 99.9% or more, or any range derivable therein.

In one embodiment, triheptanoin oil comprises less than 0.01% w/w ash. In some embodiments, triheptanoin oil comprises less than about 0.01, 0.009, 0.008, 0.007, 0.006, 0.005, 0.004, 0.003, 0.002, or 0.001% w/w ash or less, or any range derivable therein.

In one embodiment, triheptanoin oil comprises less than 0.04% w/w water. In some embodiments, triheptanoin oil comprises less than about 0.04, 0.035, 0.03, 0.025, 0.02, 0.015, 0.01, 0.005, or 0.001% w/w water or less, or any range derivable therein.

In one embodiment, triheptanoin oil comprises less than 2.5% w/w glycerol. In some embodiments, triheptanoin oil comprises less than 2.5, 2.4, 2.3, 2.2, 2.1, 2.0, 1.9, 1.8, 1.7, 1.6, 1.5, 1.3, or 1.2% w/w glycerol or less, or any range derivable therein.

In one embodiment, triheptanoin oil comprises less than 1.5% w/w monoheptanoate. In some embodiments, triheptanoin oil comprises less than 1.5, 1.4, 1.3, 1.2, 1.1, 1.0, 0.9, 0.8, 0.7, 0.6% w/w monoheptanoateor less, or any range derivable therein.

In one embodiment, triheptanoin oil comprises less than 3.0% w/w diheptanoate. In some embodiments, triheptanoin oil comprises less than 3.0, 2.9, 2.8, 2.7, 2.6, 2.5, 2.4, 2.3, 2.2, 2.1, 1.9, 1.8, or 1.7% w/w diheptanoateor less, or any range derivable therein.

In one embodiment, triheptanoin oil comprises less than 2.5% w/w Hexano-Diheptanoate. In some embodiments, triheptanoin oil comprises less than 2.5, 2.4, 2.3, 2.2, 2.1, 2.0, 1.9, 1.8, 1.7, 1.6, 1.5, 1.3, or 1.2% w/w Hexano-Diheptanoateor less, or any range derivable therein.

In one embodiment, triheptanoin oil comprises less than 2.5% w/w Hexanoic acid. In some embodiments, triheptanoin oil comprises less than 2.5, 2.4, 2.3, 2.2, 2.1, 2.0, 1.9, 1.8, 1.7, 1.6, 1.5, 1.3, or 1.2% w/w glycerol or less, or any range derivable therein.

In some embodiments, the triheptanoin oil as described herein is a colorless oil of low viscosity and is odorless and tasteless. Triheptanoin oil as described herein is typically stored at room temperature and protected from light, and its stability can exceed 24 months under such conditions.

In one embodiment, the present invention provides a solid composition comprises triheptanoin as the active ingredient; fumed silica; and cellulose acetate. In a further embodiment, the solid composition a plurality of solid particles, each particle comprising triheptanoin adsorbed onto a solid substance comprising fumed silica and cellulose acetate. In a further embodiment, the solid composition comprises, by weight of the composition, about 50% to about 80% of triheptanoin; about 10% to about 30% of fumed silica; and about 10% to about 30% of cellulose acetate. In another embodiment, the solid composition comprises, by weight of the composition, about 60% of triheptanoin; about 20% of fumed silica; and about 20% of cellulose acetate.

In one specific embodiment, the present triheptanoin oil has the characteristics listed in Table 2:

| Parameter | Specification | Method |
|---|---|---|
| | IDENTITY | |
| Triheptanoate | Comparable to reference | Ph. Eur. 2.2.28 |
| | QUALITY | |
| Appearance | Clear substance and substance is not more intensely colored than reference solution $Y_3$ | Ph. Eur. 2.2.1, 2.2.2. method I |
| Relative density | 0.95-0.98 | Ph. Eur. 2.2.5 |
| Refractive index | 1.4440-1.4465 | Ph. Eur. 2.2.6 |
| Viscosity | 15 mPa · s-23 mPa · s | Ph. Eur. 2.2.9 |
| | PURITY | |
| Composition of fatty acids | | |
| Heptanoic acid | >99% | Ph. Eur. 2.4.22 method C |
| Hexanoic acid | Max. 0.8% | |
| All other, each | <0.03% | |
| Saponification value | 360 to 410 mg KOH/g | Ph. Eur. 2.5.6 |
| Acid value | Max. 0.2 mg KOH/g | Ph. Eur. 2.5.1 |
| Hydroxyl value | Max. 10 mg KOH/g | Ph. Eur. 2.5.3 method A |
| Peroxide value | Max. 1.0 mg KOH/g | Ph. Eur. 2.5.5 method A |
| Water | Max. 0.2% | Ph. Eur. 2.5.12 |
| Total ash | Max. 0.1% | Ph. Eur. 2.4.16 |
| Heavy metals | Max. 10 ppm | Ph. Eur. 2.4.8 |

-continued

| Parameter | Specification | Method |
|---|---|---|
| POTENCY/STRENGTH | | |
| Triheptanoate | 90% to 110% | Ph. Eur. 2.2.28 |

In one specific embodiment, the present triheptanoin oil has the characteristics listed in Table 3:

| Parameter | Specification | Method |
|---|---|---|
| IDENTITY | | |
| Triheptanoate | Comparable to reference | Ph. Eur. 2.2.28 |
| IR (infrared) | Comparable to reference | Ph. Eur. 2.2.24 |
| QUALITY | | |
| Appearance | | |
| Clarity and Opalescence | Clear substance | Ph. Eur. 2.2.1 |
| Color | Substance is not more intensely colored than reference solution $Y_3$ | Ph. Eur. 2.2.2. method I |
| PURITY | | |
| Composition of fatty acids | | |
| Heptanoic acid | ≥99.0% | Ph. Eur. 2.4.22 method C |
| Hexanoic acid | ≤1.0% | |
| Individual Unidentified Impurities | ≤0.10% | |
| Impurities | | |
| Glycerol | ≤1.0% | Ph. Eur. 2.2.28 |
| Monoheptanoate | ≤0.5% | |
| Diheptanoate | ≤1.5% | |
| Hexano-Diheptanoate | ≤1.0% | |
| Individual Unidentified Impurities | ≤0.5% | |
| Total Impurities | ≤5.0% | |
| Elemental Inpurities | | |
| As | ≤0.02 ppm | Ph. Eur. 2.2.57 or 2.2.58 |
| Cd | ≤0.19 ppm | |
| Pb | ≤0.08 ppm | |
| Hg | ≤0.12 ppm | |
| Acid value | Max. 0.2 mg KOH/g | Ph. Eur. 2.5.1 |
| Water | Max. 0.2% | Ph. Eur. 2.5.12 |
| Total ash | Max. 0.1% | Ph. Eur. 2.4.16 |
| ASSAY | | |
| Triheptanoate | 95% to 103% | Ph. Eur. 2.2.28 |

In certain specific embodiments, the triheptanoin oil has the characteristics listed in Table 4:

| Parameter | Example A | Example B |
|---|---|---|
| Triheptanoate | Comparable to reference | Comparable to reference |
| Triheptanoate | 99.0% | 98.2% |
| Impurities: | | |
| Glycerol | not detectable | not detectable |
| Monoheptanoate | not detectable | not detectable |
| Diheptanoate | 0.66% | 0.62% |
| Hexano-Diheptanoate | 0.39% | 0.40% |
| Individual Unidentified Impurities | 0.20% (RRT* 1.258) | 0.18% (RRT 1.258) |
| Total Impurities | 1.25% | 1.20% |
| Elemental Inpurities | | |
| As | not detected | not detected |
| Cd | not detected | not detected |
| Pb | not detected | not detected |
| Hg | not detected | not detected |

*RRT: relative retention time.

Triheptanoin Oil Precursors and Manufacture of Triheptanoin Oil

Also provided herein are precursors to triheptanoin oil. In some embodiments, a precursor is n-heptanoic acid. n-Heptanoic acid has the following structure:

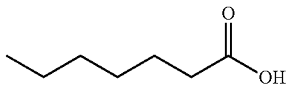

n-Heptanoic acid as described herein is of a purity or grade greater than food grade n-heptanoic acid. In some embodiments, purity of food grade n-heptanoic acid is between 90% and 98%. In some embodiments, purity of food grade n-heptanoic acid is between 95% and 98%. In some embodiments, purity of food grade n-heptanoic acid is between 95% and 97.5%. In some embodiments, purity of food grade n-heptanoic acid has a maximum purity of 98, 97.9, 97.6, 97.5, 97.4, 97.3, 97.2, 97.1, 97.0, 96.9, 96.8, 96.7, 96.6, 96.5, 96.4, 96.3%, 96.2, 96.1, 96.0, 95.9 95.8, 95.7, 95.6, 95.5, 95.4, 95.3, 95.2, or 95.1%.

In some embodiments, n-heptanoic acid as described herein is considered ultrapure pharmaceutical grade n-heptanoic acid.

Typically, the total concentration of impurities in n-heptanoic acid is less than the total concentration of impurities in food grade n-heptanoic acid. In some embodiments, total impurities in n-heptanoic acid amount to less than 4.0% w/w. In some embodiments, total impurities amount to less than about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, or 0.01% w/w or less, or any range derivable therein.

In one embodiment, n-heptanoic acid comprises less than 2% w/w of triglycerides esterified with acids other than C7 acids (e.g., C2, C3, C4, C5, C6, C8, or C9 acids, or others, or combinations thereof ("non-C7 triglycerides")). In some embodiments, n-heptanoic acid comprises less than 2, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2 or 0.1% w/w or less of non-C7 triglycerides, or any range derivable therein.

In one embodiment, an n-heptanoic acid composition comprises a sum of C7 carboxylic acids having greater than 97% purity. In some embodiments, the purity is greater than 97, 97.1, 97.2, 97.3, 97.4, 97.5, 97.6, 97.7, 97.8, 97.9, 98, 98.1, 98.2, 98.3, 98.4, 98.5, 98.6, 98.7, 98.8, 98.9, 99, 99.1, 99.2, 99.3, 99.4, 99.5, 99.6, 99.7, 99.8 or 99.9%, or more, or any range derivable therein. Compositions, such as pharmaceutical compositions, comprising n-heptanoic acid are also provided. Further, any composition comprising n-heptanoic acid can optionally be further defined as a pharmaceutical composition.

Triheptanoin oil can be prepared from n-heptanoic acid as described herein or a composition comprising n-heptanoic acid. For example, n-heptanoic acid can be esterified with glycerol to produce triheptanoin oil, such as in the presence of a basic catalyst and heat.

In one embodiment, an n-heptanoic acid composition comprises less than 3.0% w/w of 2-methylhexanoic acid. In some embodiments, the composition comprises less than 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1% w/w 2-methylhexanoic acid, or less, or any range derivable therein.

In one embodiment, an n-heptanoic acid composition comprises less than 0.1% w/w water. In some embodiments, a composition comprises less than 0.1, 0.09, 0.08, 0.07, 0.06, 0.05, 0.04, 0.03, 0.02, or 0.01% w/w of water or less, or any range derivable therein.

In one embodiment, an n-heptanoic acid composition comprises a carbonyl content of less than 0.2% w/w. Carbonyl content measurements are well-known in the art. In some embodiments, the carbonyl content is less than 0.15, 0.1, 0.05, or 0.01% w/w, or less, or any range derivable therein.

In one embodiment, an n-heptanoic acid composition comprises an iodine number of less than 0.5%. Iodine number measurements are well-known in the art. In some embodiments, the iodine number is less than 0.5, 0.4, 0.3, 0.2, or 0.1% or less, or any range derivable therein.

In one embodiment, an n-heptanoic acid composition comprises less than 0.2 mg/kg iron. In some embodiments, a composition comprises less than 0.2, 0.15, 0.1, 0.05, or 0.01 mg/kg iron, or any range derivable therein.

In one embodiment, a composition comprising n-heptanoic acid has a platinum/cobalt color number of less than 0.25. Determination of the platinum/cobalt color number is well-known in the art. In some embodiments, the platinum/cobalt color number is less than 0.25, 0.2, 0.15, 0.1, or 0.05 or less, or any range derivable therein.

Therapeutic Treatments

Provided herein in some embodiments are methods of using the present solid composition for treatment. The solid composition can be administered to a subject in need thereof in an amount effective to treat the subject.

For example, a subject may suffer from any one or more of the following: a fatty acid oxidation disorder or deficiency; adult polyglucosan body disease; a mitochondrial fat oxidation defect (e.g., relating to carnitine palmitoyl transferase I, carnitine palmitoyl transferase II, carnitine acylcarnitine translocase, very long chain acyl-CoA dehydrogenase, trifunctional protein, long chain hydroxyacyl-CoA dehydrogenase, multiple acyl-CoA dehydrogenase, short chain acyl CoA dehydrogenase, alpha glucosidase, brancher enzyme, debrancher enzyme, myophosphorylase, or phosphofructokinase); a glycogen storage disease (e.g., glycogen storage disease Type II); glucose transporter type 1 (GLUT1) deficiency syndrome; or a mitochondrial myopathy. In some embodiments, triheptanoin oil as described herein or a pharmaceutical composition comprising triheptanoin oil can be used to treat any condition described in U.S. Pat. No. 8,106,093.

In another embodiment, a subject may suffer from urea cycle disorders (UCD), which include several inherited deficiencies of enzymes or transporters necessary for the synthesis of urea from ammonia, including enzymes involved in the urea cycle; or hepatic encephalopathy (HE), which a spectrum of neurologic signs and symptoms believed to result from hyperammonemia, which frequently occur in subjects with cirrhosis or certain other types of liver disease. In some embodiments, glycerol phenylbutyrate as described herein or a pharmaceutical composition comprising glycerol phenylbutyrate can be used to treat these conditions. Further details of methods of treatment using glycerol phenylbutyrate can be found in U.S. Pat. Nos. 8,404,215 and 8,642,012, the contents of which are hereby incorporated by reference in entirety for all purpose.

In one embodiment, the solid compositions can be administered to a patient directly in various dosage forms (e.g., powders, granules, tablets, capsules, and the like) without mixing with food, drink, or other comestible compositions. In another embodiment, the solid compositions, such as powders or granules, can be taken together with food, drink, or other comestible compositions by mixing the solid compositions into the food, drink, or comestible compositions. The food, drink, or comestible compositions can be in any form including liquid, solid, semi-solid, foamy material, paste, gel, cream, lotion, and combinations thereof. The solid compositions can provide therapeutic effects while minimize gastric upset and gastrin release, and co-administration with food, drink, or other comestible compositions can enhance such tolerability benefit. In addition, co-administration of food, drink, or other comestible compositions with the solid composition can provide delayed and/or extended release of the active ingredients and thus allow less frequent dosing, longer term of energy exposure, and potentially higher efficiency in absorption from the GI tract. The delayed and/or extended release characteristic of the solid composition can also be independently achieved by including one or more sustained release polymers in the solid compositions as discussed above.

As used herein, the term "effective" (e.g., "an effective amount") means adequate to accomplish a desired, expected, or intended result. An effective amount can be a therapeutically effective amount. A "therapeutically effective amount" refers to the amount of an active ingredient that, when administered to a subject, is sufficient to effect such treatment of a particular disease or condition. The "therapeutically effective amount" will vary depending on, e.g., the disease or condition, the severity of the disease or condition, and the age, weight, etc., of the subject to be treated.

In general, "treating" or "treatment" of any condition, disease or disorder refers, in some embodiments, to ameliorating the condition, disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to inhibiting the condition, disease or disorder, either physically, (e.g., stabilization of a discernible symptom), physiologically, (e.g., stabilization of a physical parameter) or both. In some embodiments, "treating" or "treatment" refers to delaying the onset of a condition, disease, or disorder.

EXAMPLES

Example 1

Table 5 shows the high purity of exemplary triheptanoin oil samples and solid samples comprising triheptanoin oil in accordance with the present invention.

Further, the stability of an exemplary solid composition (solid sample 2 in Table 5) comprising triheptanoin oil was tested. Measurements were conducted after storage at 25° C./60% RH (relative humidity) in double LDPE (low density polyethylene) bags in a 60 cc induction sealed HDPE (high density polyethylene) bottle and results are shown in Table 6. Measurements were also conducted after storage at 40° C./75% RH in double LDPE bags in a 60 cc induction sealed HDPE bottle and results are shown in Table 7.

TABLE 5

Initial Purity Test Results

| | Parameter | | | | | |
|---|---|---|---|---|---|---|
| Impurities | Specification | OIL Sample 1 | OIL Sample 2 | SOLID Sample 1 | SOLID Sample 2 | SOLID Sample 3 |
| Glycerol | ≤1.0% | ND | ND | ND | ND | ND |
| Monoheptanoate | ≤0.5% | ND | ND | ND | ND | ND |
| Diheptanoate | ≤1.5% | 1.2% | 0.7% | 1.1% | 1.1% | 1.1% |
| Hexano-Diheptanoate | ≤1.0% | 0.4% | 0.4% | 0.4% | 0.4% | 0.4% |
| Individual Unidentified Impurities: RRT* (%) | ≤0.5% | RRT 0.91: 0.06%<br>RRT 1.05: 0.16%<br>RRT 1.06: 0.17%<br>RRT 1.07: 0.11%<br>RRT 1.25: 0.06%<br>RRT 1.26: 0.23%<br>RRT 1.30: 0.10%<br>RRT 1.36: 0.11% | RRT 1.26: 0.20% | RRT 0.91: 0.06%<br>RRT 1.05: 0.16%<br>RRT 1.06: 0.17%<br>RRT 1.07: 0.11%<br>RRT 1.25: 0.06%<br>RRT 1.26: 0.23%<br>RRT 1.30: 0.10%<br>RRT 1.36: 0.11% | RRT 0.91: 0.06%<br>RRT 1.05: 0.16%<br>RRT 1.06: 0.17%<br>RRT 1.07: 0.11%<br>RRT 1.25: 0.06%<br>RRT 1.26: 0.23%<br>RRT 1.30: 0.10%<br>RRT 1.36: 0.11% | RRT 0.91: 0.06%<br>RRT 1.05: 0.16%<br>RRT 1.06: 0.17%<br>RRT 1.07: 0.11%<br>RRT 1.25: 0.06%<br>RRT 1.26: 0.24%<br>RRT 1.30: 0.10%<br>RRT 1.36: 0.11% |
| Total Impurities | ≤5.0% | 2.6% | 1.3% | 2.6% | 2.6% | 2.6% |

RRT = relative retention time.

ND = not detected.

TABLE 6

Stability Study Results for an exemplary solid composition stored at 25° C./60% RH:

| | | Time points (months) | | |
|---|---|---|---|---|
| Parameter | Specification | Freshly Made (Five months before) | 0 | 1 |
| Appearance | White to off-white powder | Conforms | Conforms | Conforms |
| Impurities | | | | |
| Glycerol | ≤1.0% | ND | ND | ND |
| Monoheptanoate | ≤0.5% | ND | ND | ND |
| Diheptanoate | ≤1.5% | 1.1% | 1.1% | 1.1% |
| Hexano-Diheptanoate | ≤1.0% | 0.4% | 0.4% | 0.4% |
| Individual Unidentified Impurities: RRT (%) | ≤0.5% | RRT 0.91: 0.06%<br>RRT 1.05: 0.16%<br>RRT 1.06: 0.17%<br>RRT 1.07: 0.11%<br>RRT 1.25: 0.06%<br>RRT 1.26: 0.23%<br>RRT 1.30: 0.10%<br>RRT 1.36: 0.11% | RRT 0.91: 0.06%<br>RRT 1.05: 0.16%<br>RRT 1.06: 0.17%<br>RRT 1.07: 0.11%<br>RRT 1.25: 0.06%<br>RRT 1.26: 0.24%<br>RRT 1.30: 0.10%<br>RRT 1.36: 0.11% | RRT 0.91: 0.05%<br>RRT 1.05: 0.16%<br>RRT 1.06: 0.17%<br>RRT 1.07: 0.11%<br>RRT 1.25: 0.06%<br>RRT 1.26: 0.23%<br>RRT 1.30: 0.09%<br>RRT 1.36: 0.09% |
| Total Impurities | ≤5.0% | 2.6% | 2.6% | 2.5% |
| Water | NMT 5% | NS | 0.29% | 0.35% |
| Triheptanoate | 90%-110% | 99% | 101% | 100% |
| Acetone | ≤200 ppm | <100 ppm | NS | NS |

RRT = relative retention time.

NMT = not more than.

ND = not detected.

TABLE 7

Stability Study Results for an exemplary solid composition stored at 40° C./75% RH:

| Parameter | Specification | Time points (months) Freshly Made (Five months before) | 0 | 1 |
|---|---|---|---|---|
| Appearance | White to off-white powder | Conforms | Conforms | Conforms |
| Impurities | | | | |
| Glycerol | ≤1.0% | ND | ND | ND |
| Monoheptanoate | ≤0.5% | ND | ND | ND |
| Diheptanoate | ≤1.5% | 1.1% | 1.1% | 1.1% |
| Hexano-Diheptanoate | ≤1.0% | 0.4% | 0.4% | 0.4% |
| Individual Unidentified Impurities: RRT (%) | ≤0.5% | RRT 0.91: 0.06%<br>RRT 1.05: 0.16%<br>RRT 1.06: 0.17%<br>RRT 1.07: 0.11%<br>RRT 1.25: 0.06%<br>RRT 1.26: 0.23%<br>RRT 1.30: 0.10%<br>RRT 1.36: 0.11% | RRT 0.91: 0.06%<br>RRT 1.05: 0.16%<br>RRT 1.06: 0.17%<br>RRT 1.07: 0.11%<br>RRT 1.25: 0.06%<br>RRT 1.26: 0.24%<br>RRT 1.30: 0.10%<br>RRT 1.36: 0.11% | RRT 0.91: 0.05%<br>RRT 1.05: 0.16%<br>RRT 1.06: 0.17%<br>RRT 1.07: 0.11%<br>RRT 1.25: 0.06%<br>RRT 1.26: 0.23%<br>RRT 1.30: 0.09%<br>RRT 1.36: 0.10% |
| Total Impurities | ≤5.0% | 2.6% | 2.6% | 2.5% |
| Water | NMT 5% | NS | 0.29% | 0.45% |
| Triheptanoate | 90%-110% | 99% | 101% | 98% |
| Acetone | ≤200 ppm | <100 ppm | NS | NS |

RRT = relative retention time.
NMT = not more than.
ND = not detected.

Example 2

Single dose study of each arm with full pharmacokinetics (PK) profile through 48 hours post dose was performed to determined when metabolites return to baseline (one week washout between each arm) as well as if acute release of gastrin and cholesystokinin (CCK) hormones cause spasmodic stomach contractions. Blood samples were collected from each arm 0-90 min plus anytime outside this window if gastric distress observed.

More specifically, animals (n=3/sex) were fasted prior to dose and fed 4 hrs post dose. Blood samples for PK analysis of triheptanoin and metabolites were collected pre-dose through 48 hrs post dose. As seen in the multiple dose study (Example 3), there were no major differences between males and females thus data was combined for all metabolites.

In FIGS. 1-21, animals were administered a single oral gavage dose level of a triheptanoin oil sample (i.e., the oil) or exemplary solid samples comprising triheptanoin oil in accordance with the present invention. The two exemplary solid compositions comprise 1) 60%:20%:20% of triheptanoin oil:Cab-O-Sil:cellulose acetate (i.e., the Powder-ER); and 2) 80%:20% of triheptanoin oil:Cab-O-Sil (i.e., the Powder), respectively.

Triheptanoin and Heptanoic Acid

Triheptanoin is metabolized to heptanoic acid. The metabolite PK profiles for the three samples are shown in FIGS. 1-4. Bio-modal peaks were observed for heptanopic acid on three arms. It is contemplated that: 1) the first peak may be when the triheptanoin hits the stomach and the second peak may be when the triheptanoin hits the duodenum; 2) fat soluble materials can be dissolved in the stomach but free heptanoin is absorbed in the duodenum (higher $2^{nd}$ peak for the powders); and 3) the cellulose acetate in the Powder-ER formulation delays delivery by ~one hour.

Energy Metabolites: Ketones

As seen in FIGS. 5-9, we observed comparable levels of ketones with oil treatment and powder-ER treatment. Delivery of C4 ketones were faster with powders but also blunted by the powders. The ratio C4 ketone: C5 ketone indicates the state of feeding; as this ratio increases it indicates that triheptanoin is being used as a source of calories.

Energy Metabolites: Aspartate

Figure 10:
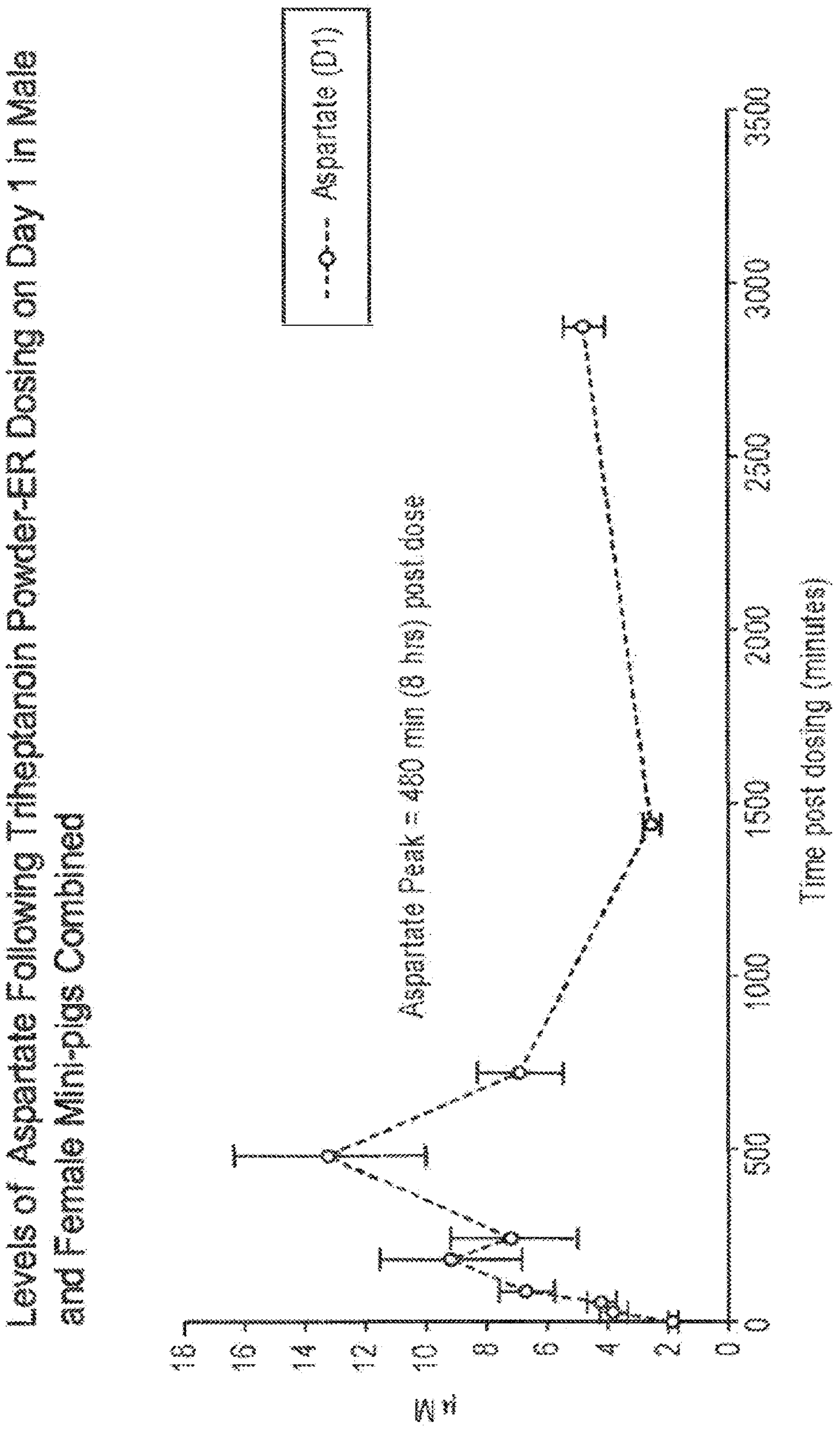
FIG. 10 is the metabolite PK profile of aspartate following triheptanoin powder-ER dosing on Day 1 in male and female mini-pigs combined.
Figure 11:
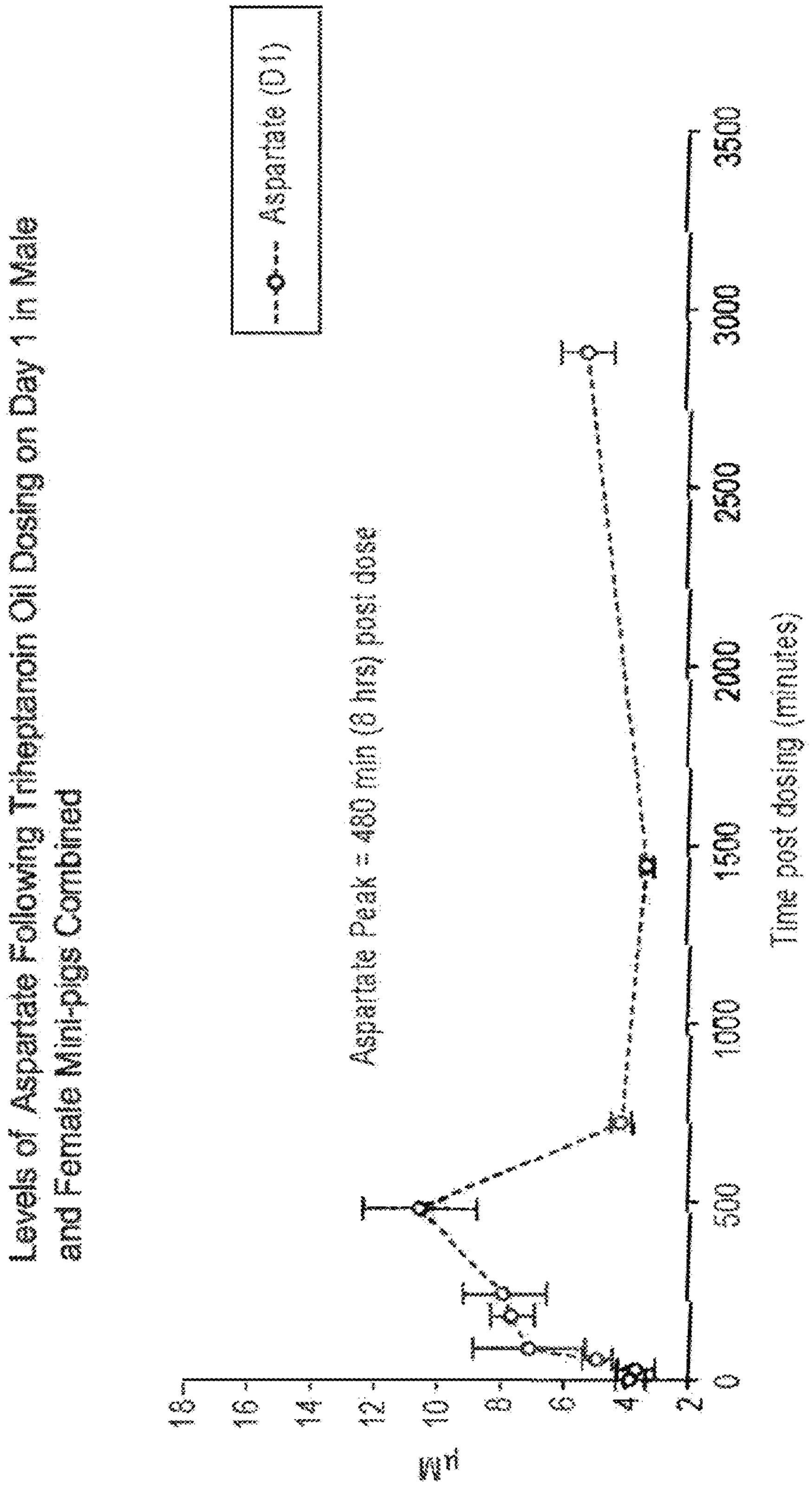
FIG. 11 is the metabolite PK profile of aspartate following triheptanoin oil dosing on Day 1 in male and female mini-pigs combined.
Figure 12:
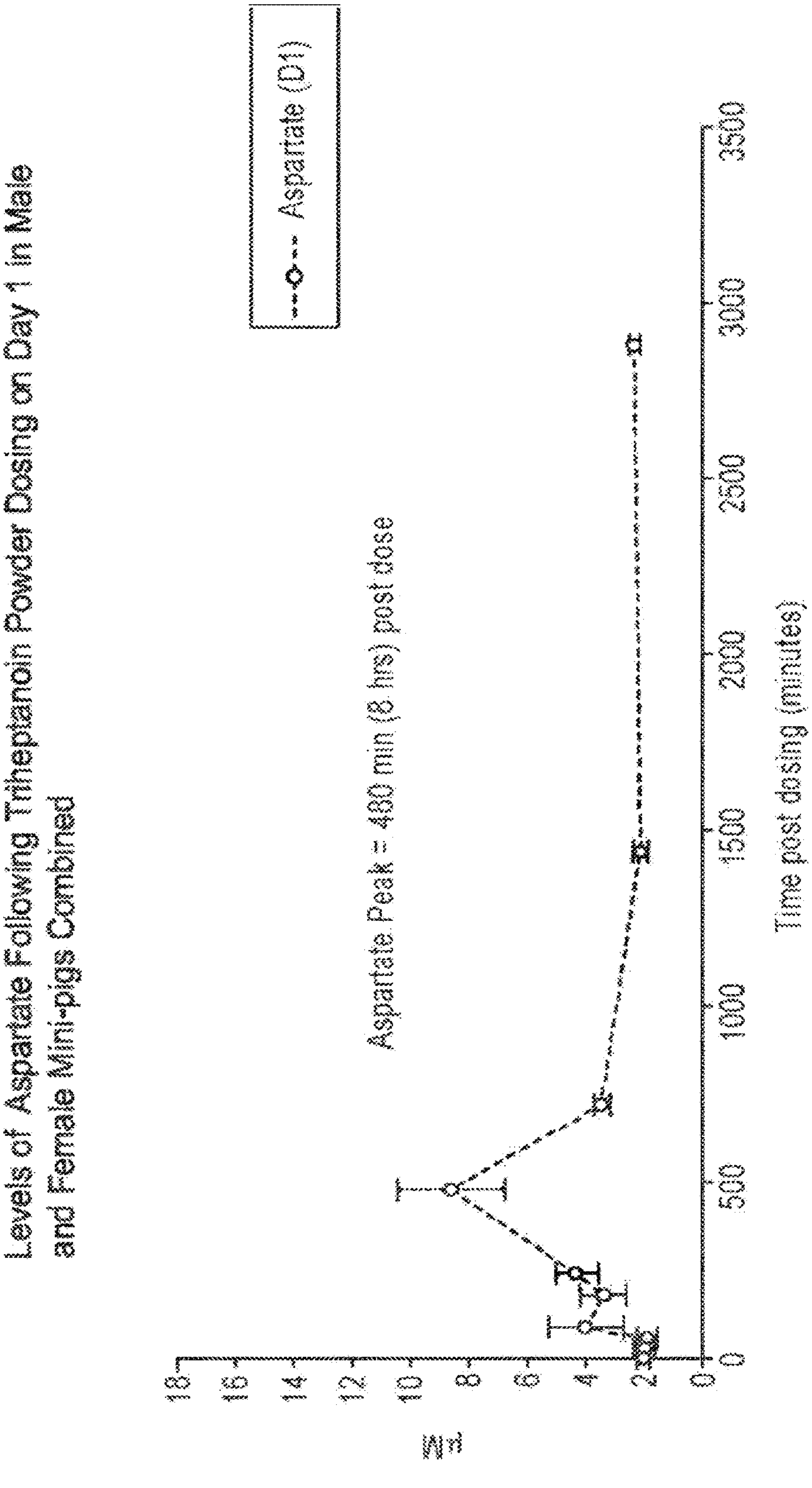
FIG. 12 is the metabolite PK profile of aspartate following triheptanoin powder dosing on Day 1 in male and female mini-pigs combined.

The levels of aspartate of the three samples are shown in FIGS. 10-12. We observed sustained release with the Powder-ER. It also showed a more favorable effect on gluconeogenic precursors because of the delay in release. The levels of aspartate of the Oil and the powder return to baseline at 8 hrs, while that of the powder-ER returns to baseline at 24 hrs post dose.

Energy Metabolites: Glutamate

Figure 13:
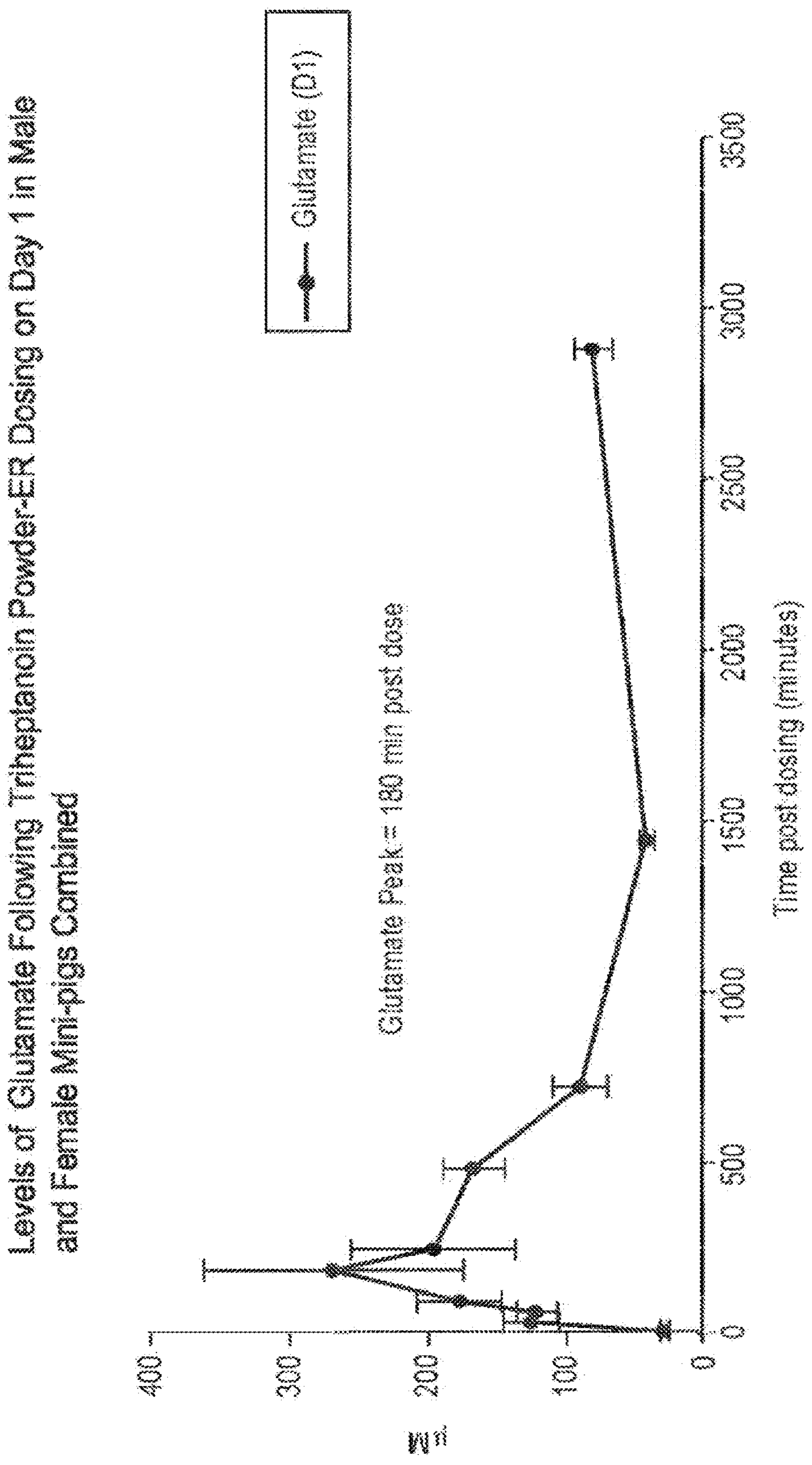
FIG. 13 is the metabolite PK profile of glutamate following triheptanoin powder-ER dosing on Day 1 in male and female mini-pigs combined.
Figure 14:
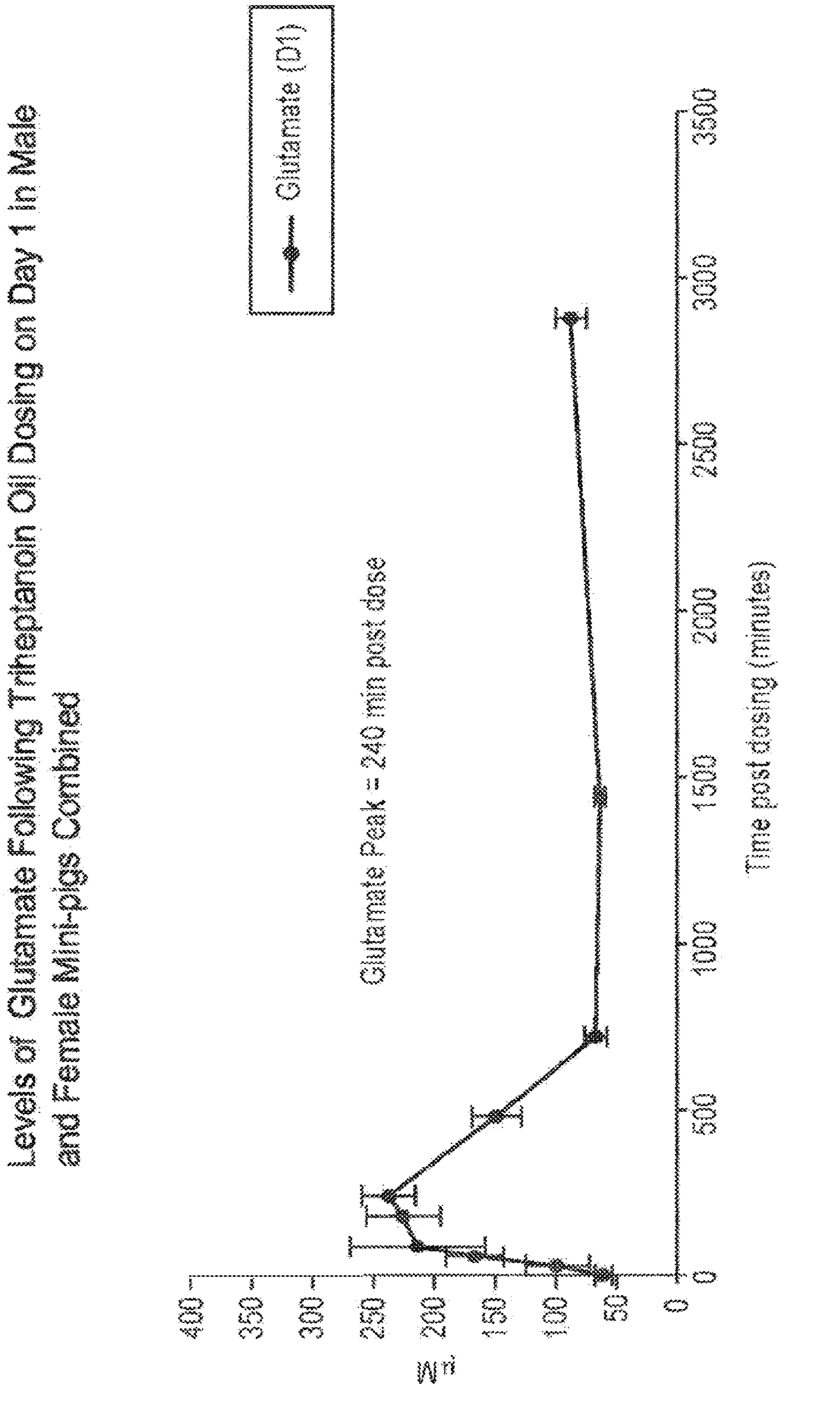
FIG. 14 is the metabolite PK profile of glutamate following triheptanoin oil dosing on Day 1 in male and female mini-pigs combined.
Figure 15:
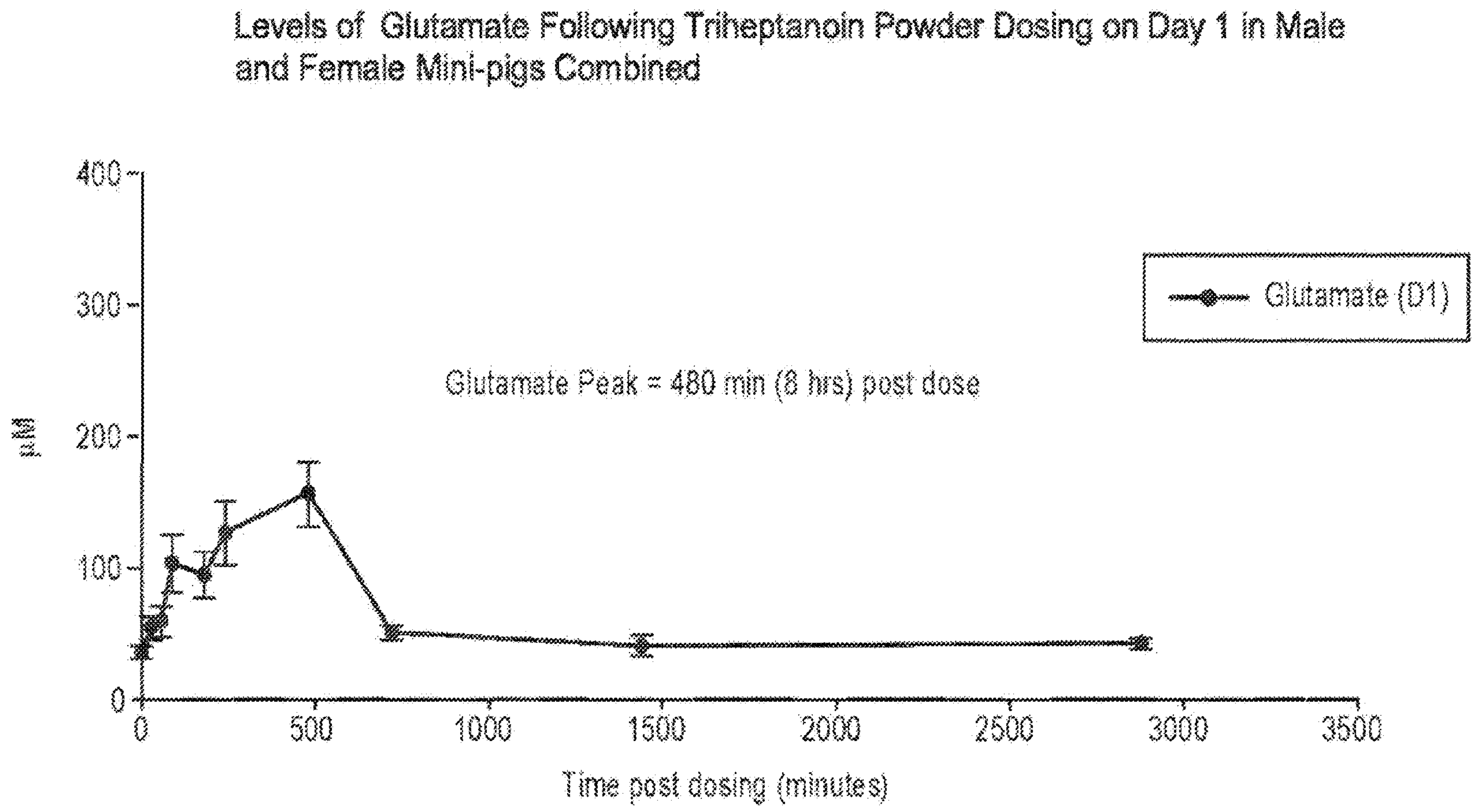
FIG. 15 is the metabolite PK profile of glutamate following triheptanoin powder dosing on Day 1 in male and female mini-pigs combined.

The levels of glutamate of the three samples are shown in FIGS. 13-15. When glutamate increases, the trend indicates that triheptanoin protects against hypoglycemia. Triheptanoin increases the chemicals that can be made into glucose. Livers in minipigs store gluconeogenic precursors in the form of glutamate based on presence in the blood.

Alternative Metabolites

Figure 16:
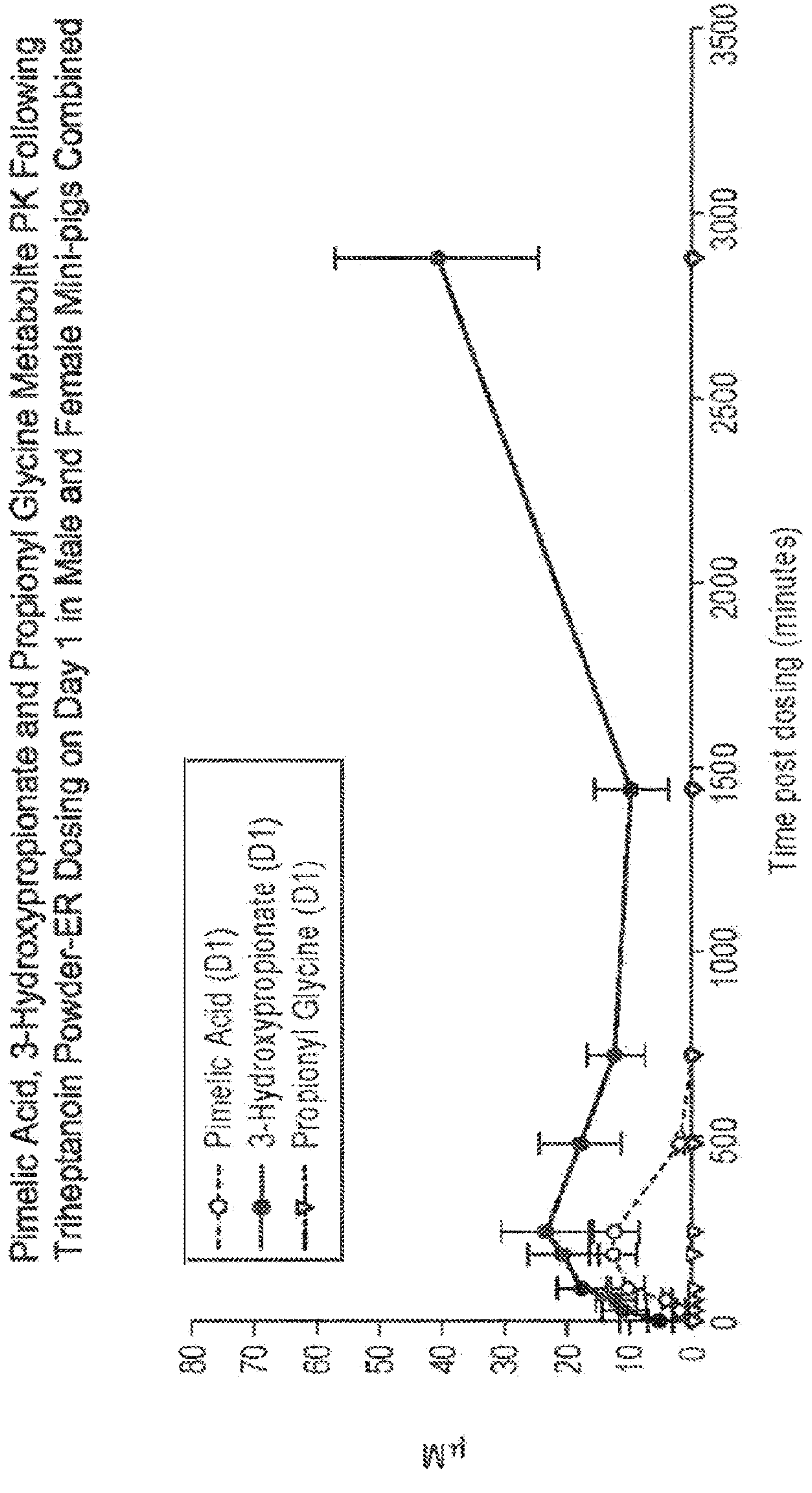
FIG. 16 is the metabolite PK profile of pimelic acid, 3-hydroxypropionate and propionyl glycine following triheptanoin powder-ER dosing on Day 1 in male and female mini-pigs combined.
Figure 17:
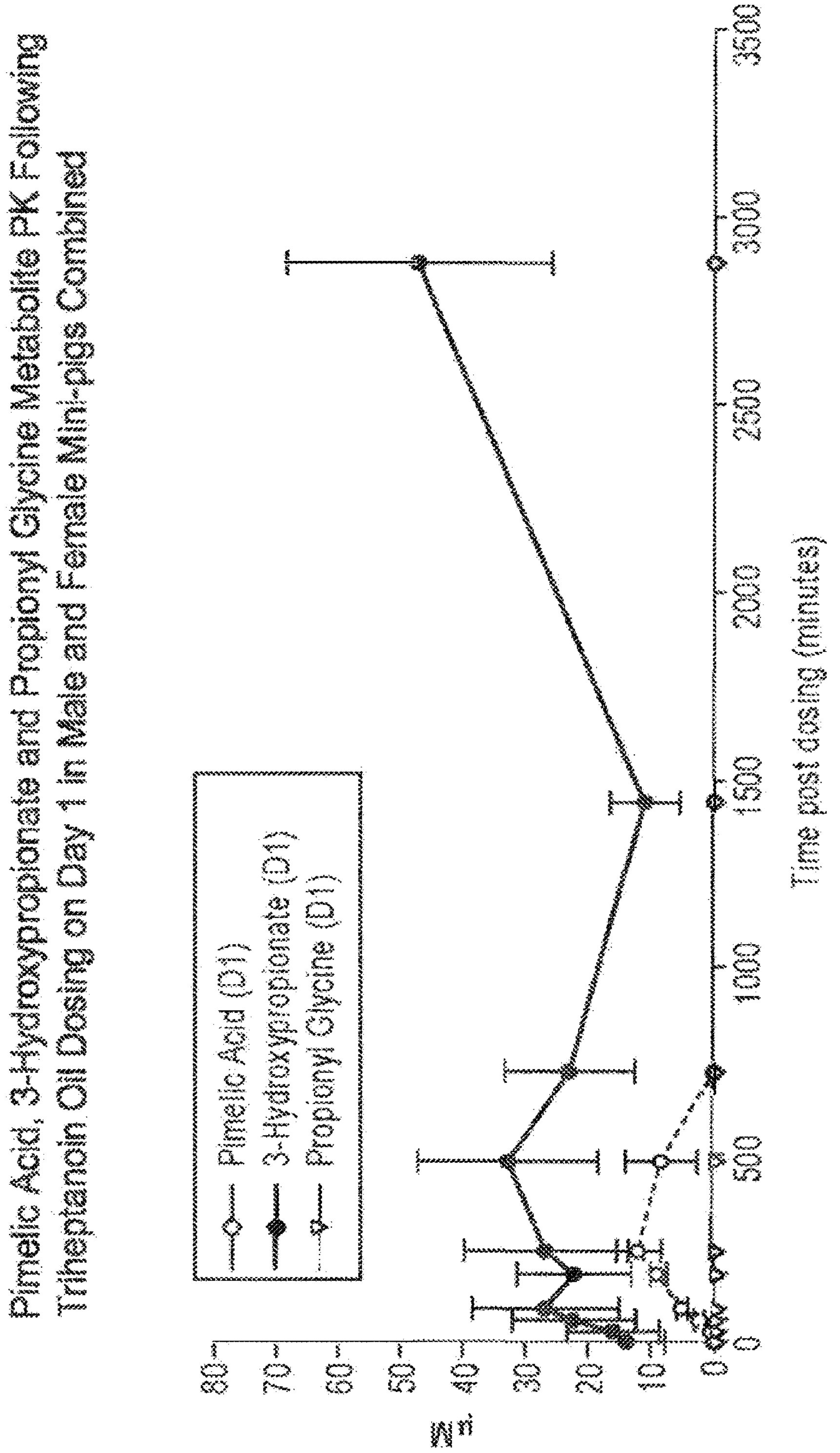
FIG. 17 is the metabolite PK profile of pimelic acid, 3-hydroxypropionate and propionyl glycine following triheptanoin oil dosing on Day 1 in male and female mini-pigs combined.
Figure 18:
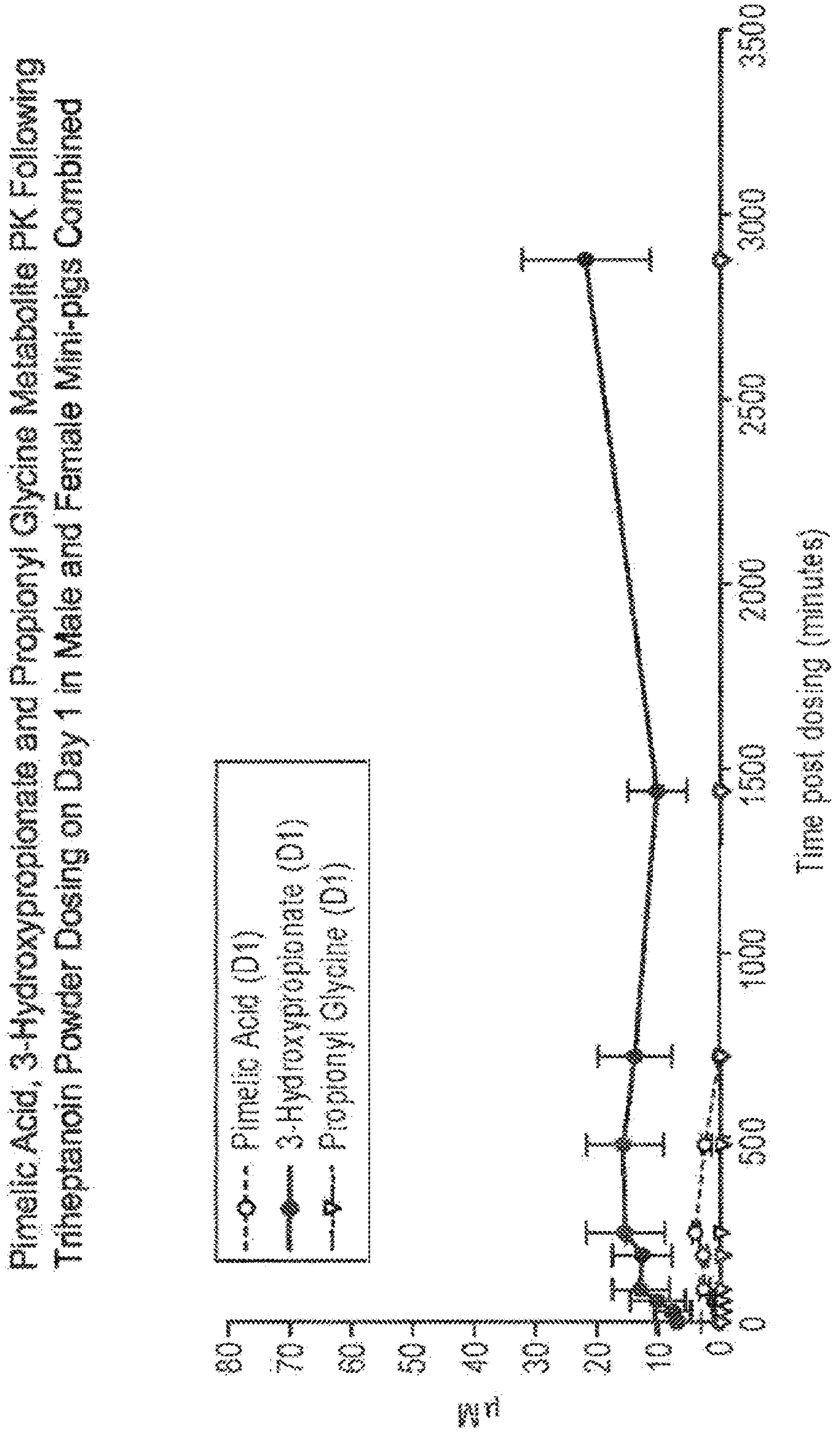
FIG. 18 is the metabolite PK profile of pimelic acid, 3-hydroxypropionate and propionyl glycine following triheptanoin powder dosing on Day 1 in male and female mini-pigs combined.

The metabolite PK profiles of alternative metabolites including pimelic acid, 3-hydroxypropionate and propionyl glycine are shown in FIGS. 16-18. Pimelic acid and 3-hydroxypropionate production was not increased with the Powder-ER when compared to the oil. The levels were lower for the powder. 3-hydroxyproprionate is a normal acid made by gut bacteria, but very dependent on the individual animal.

Figure 19:
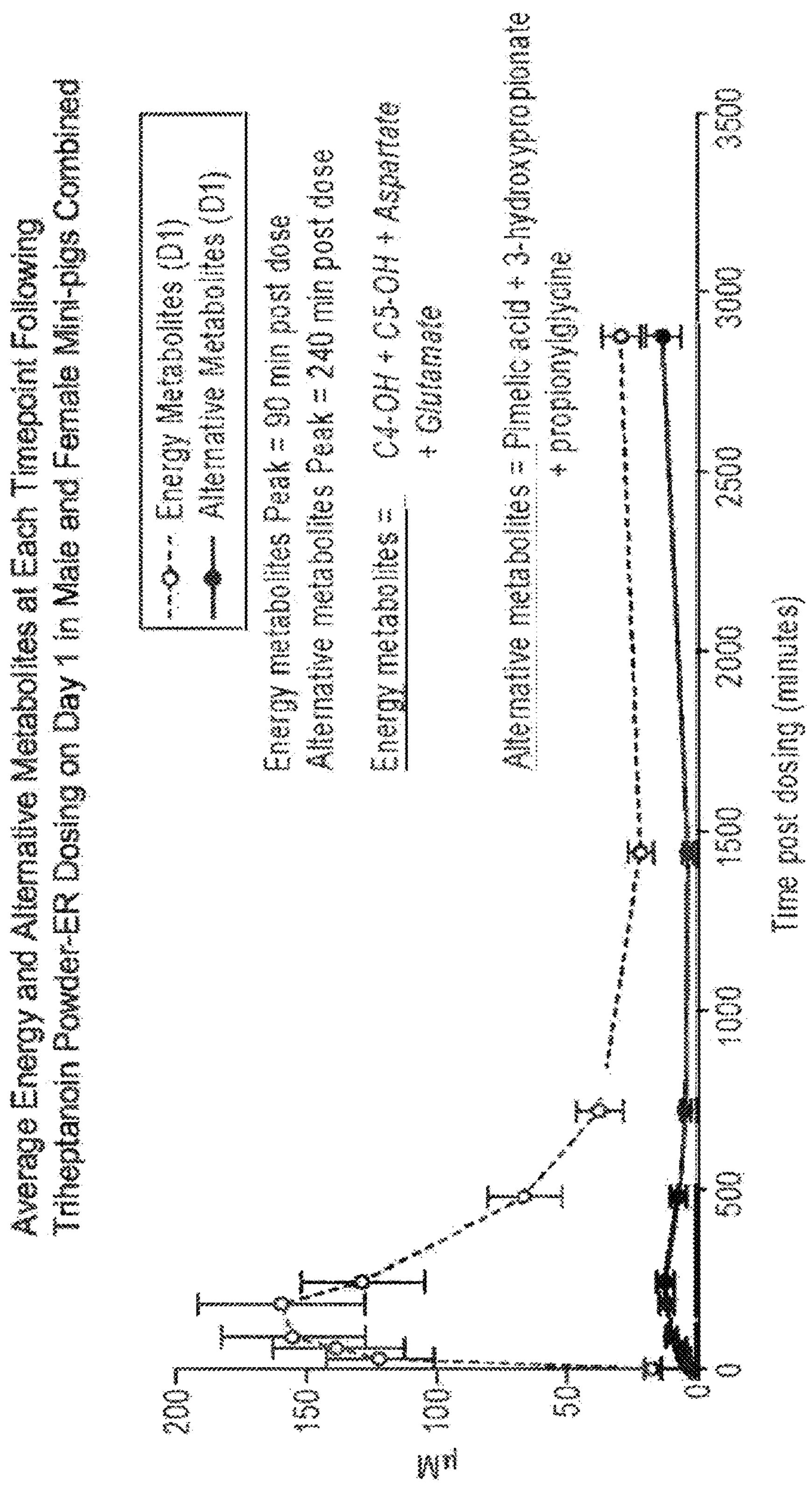
FIG. 19 is the profile of average energy and alternative metabolites following triheptanoin powder-ER dosing on Day 1 in male and female mini-pigs combined.
Figure 20:
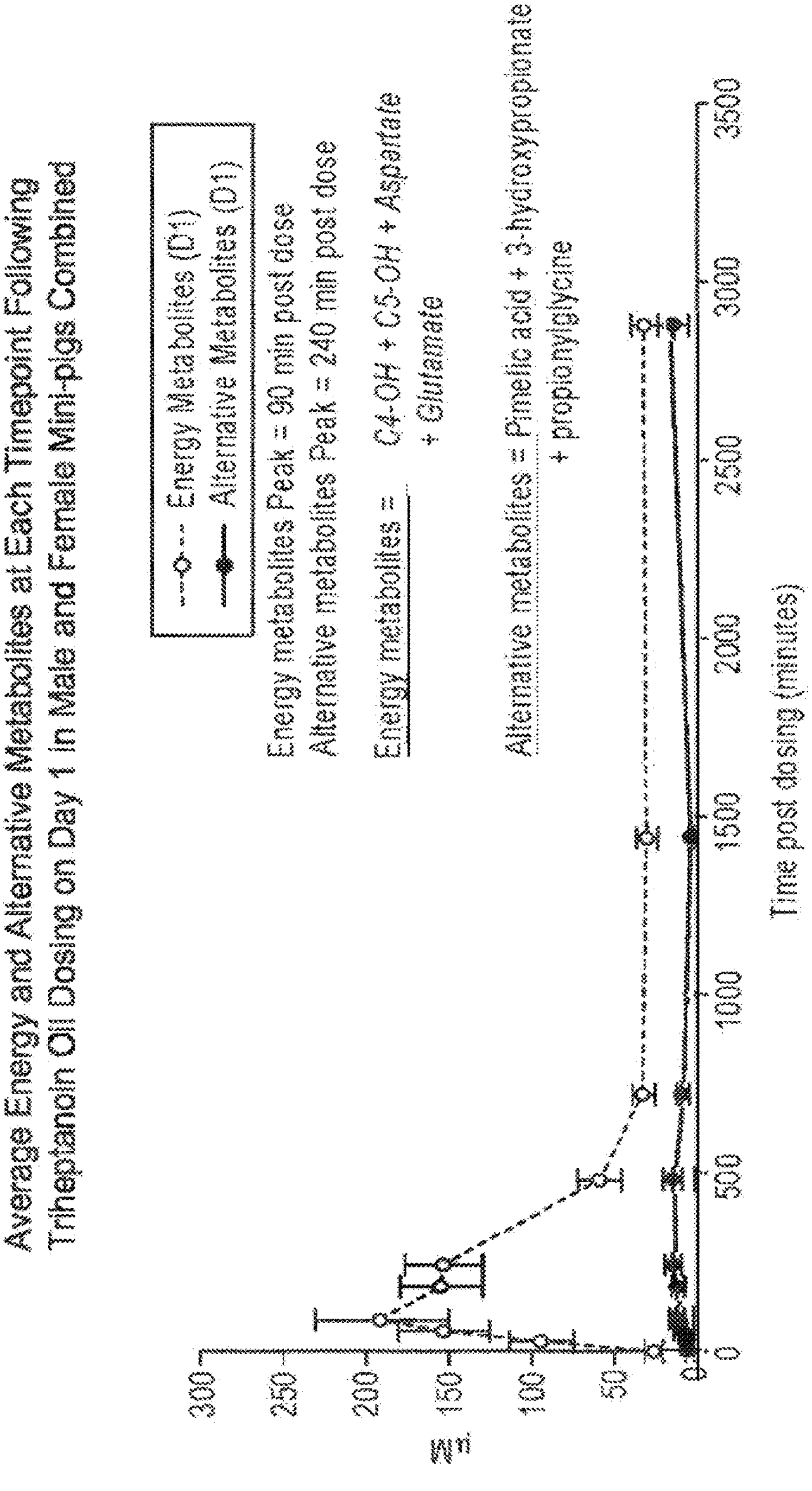
FIG. 20 is the profile of average energy and alternative metabolites following triheptanoin oil dosing on Day 1 in male and female mini-pigs combined.
Figure 21:
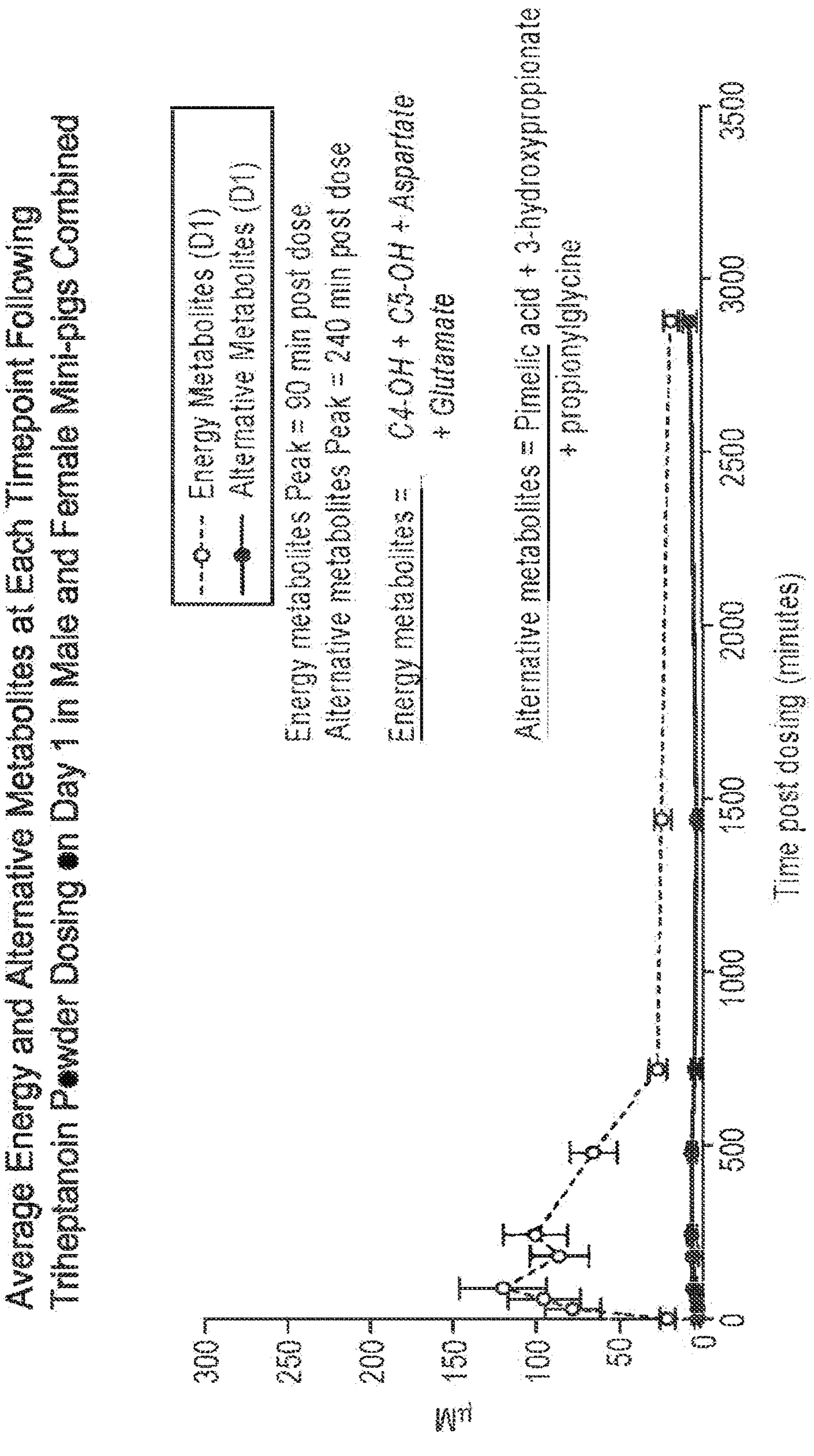
FIG. 21 is the profile of average energy and alternative metabolites following triheptanoin powder dosing on Day 1 in male and female mini-pigs combined.

We have increased co-enzyme A activity by giving triheptanoin. In addition, the levels of average energy and alternative metabolites are shown in FIGS. 19-21.

Example 3

Multiple dose study was performed on the oil, the Powder and the Powder-ER as used in Example 2 and the results are shown below.

Powder Arm:

Day 1: Animal #6501 vomited ~1 hour post dose

Day 3: Animal #6502 vomited

Day 3: Animal #6510 gastric distressed observed

Oil Arm:

Day 1: Animal #6501 vomited ~3 hours post dose

Day 1: Animal #6516 vomited ~3 hours post dose

Day 5: Animal #6509 gastric distressed observed

Powder ER Arm:

No vomiting or gastric distress observed

Heptanoic Acid Across Dose Groups

Figure 22:
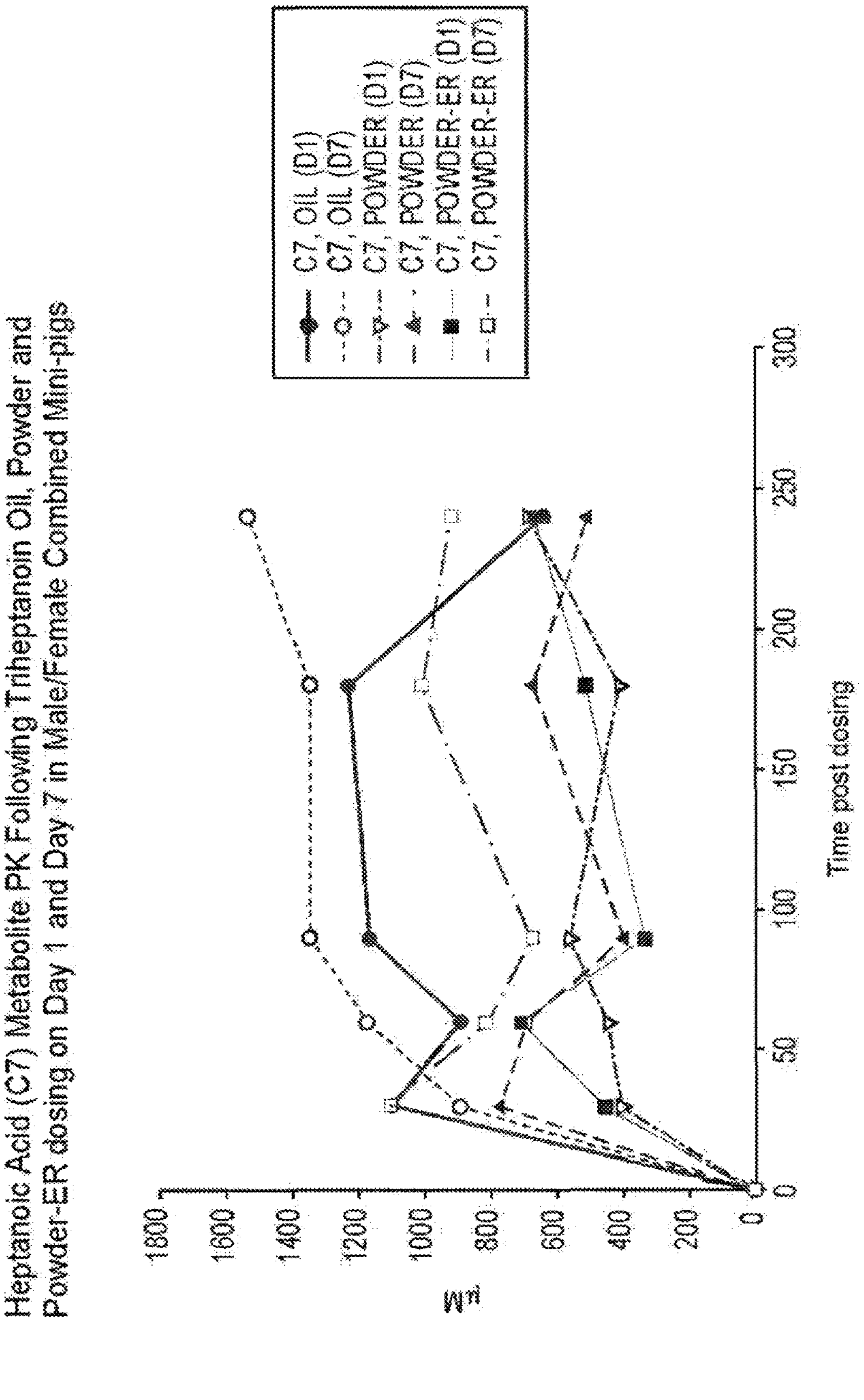
FIG. 22 is the metabolite PK profile of heptanoic acid following triheptanoin oil dosing on Day 1 and Day 7 in male and female mini-pigs combined.

Overall, results as expected, the triheptanoin releases heptanoic acid. Referring to FIG. 22, triheptanoin was metabolized primarily in liver to C7 fatty acids and ketone bodies which distribute via circulation to other tissues to provide an energy source. There were no triheptanoin values in oil arm. All triheptanoin oil was converted to C7.

Trace amounts of triheptanoin were observed in powder arm. The powder matrix may have caused a delay in the lipase action, this delay is slowing the release of C7. The Powder ER arm released slightly higher levels of heptanoic acid than the powder arm but not as high as the oil.

Energy Metabolites

Figure 23:
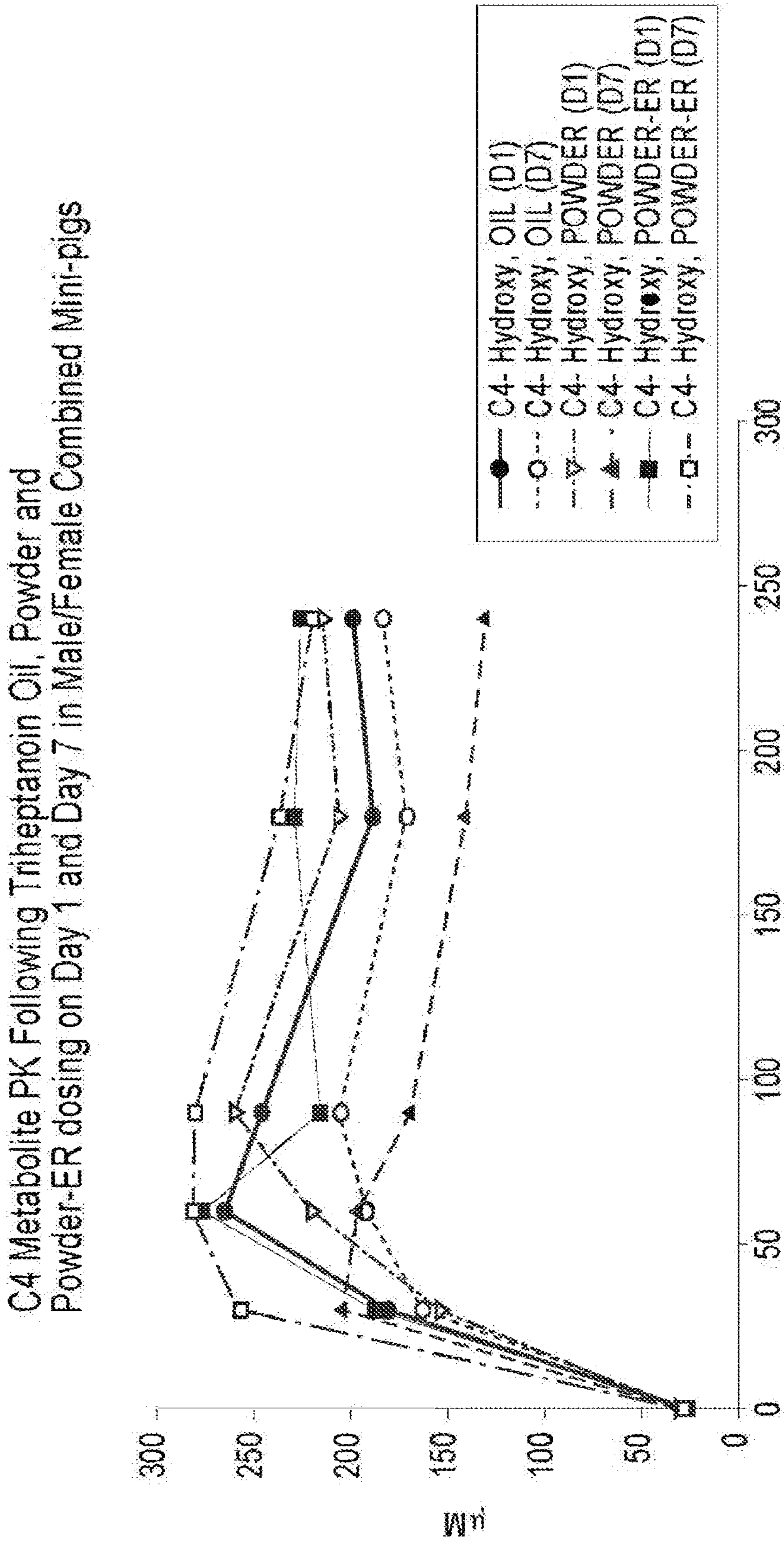
FIG. 23 is the metabolite PK profile of C4-hydroxy following triheptanoin oil, powder and powder-ER dosing on Day 1 and Day 7 in male and female mini-pigs combined.
Figure 24:
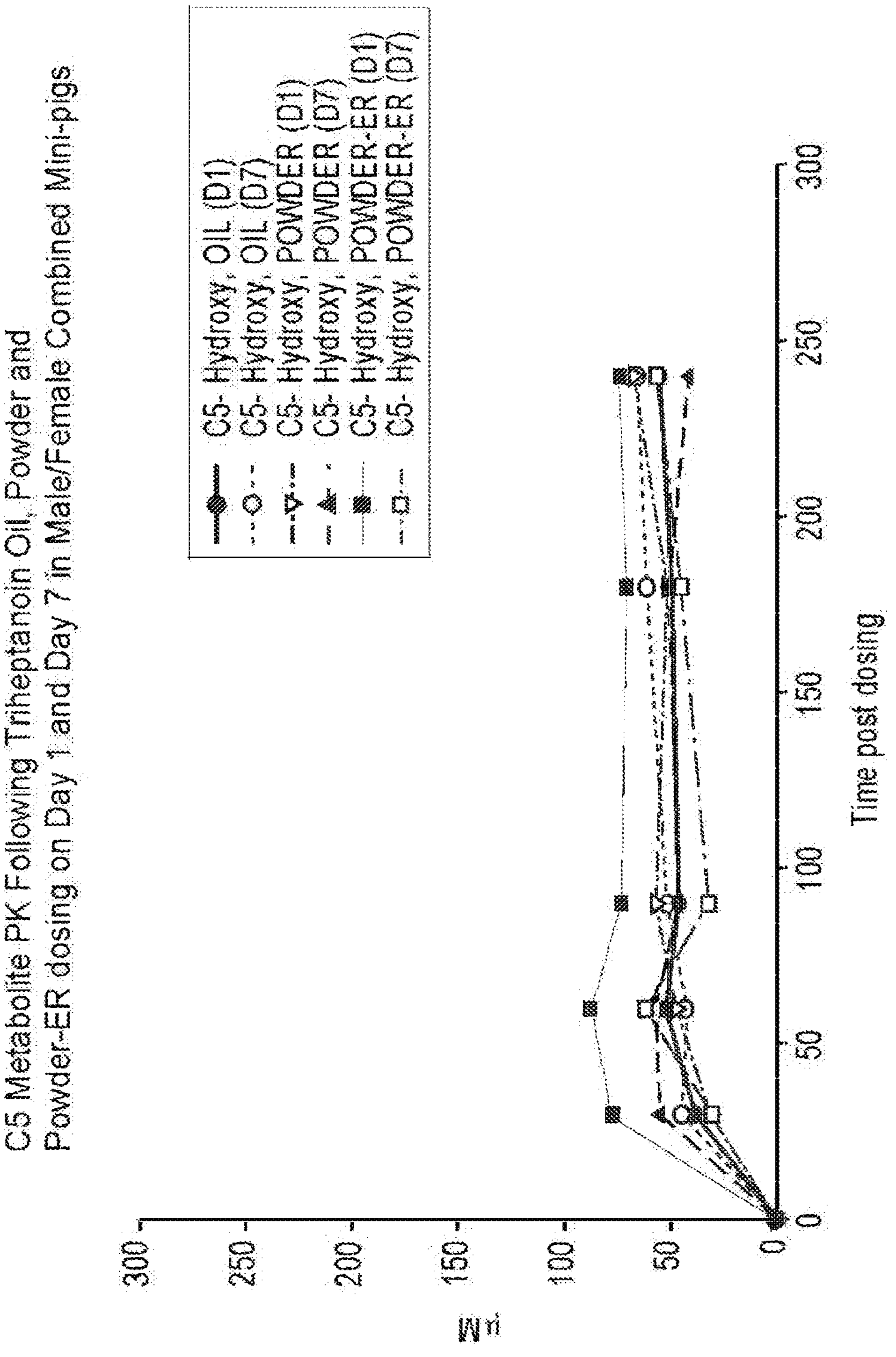
FIG. 24 is the metabolite PK profile of C5-hydroxy following triheptanoin oil, powder and powder-ER dosing on Day 1 and Day 7 in male and female mini-pigs combined.

As seen in FIGS. 23 and 24, beta hydroxy levels rose 10-fold above resting state while ketone bodies did not increase from Day 1 to Day 7, which indicated no chance for ketosis.

Figure 25:
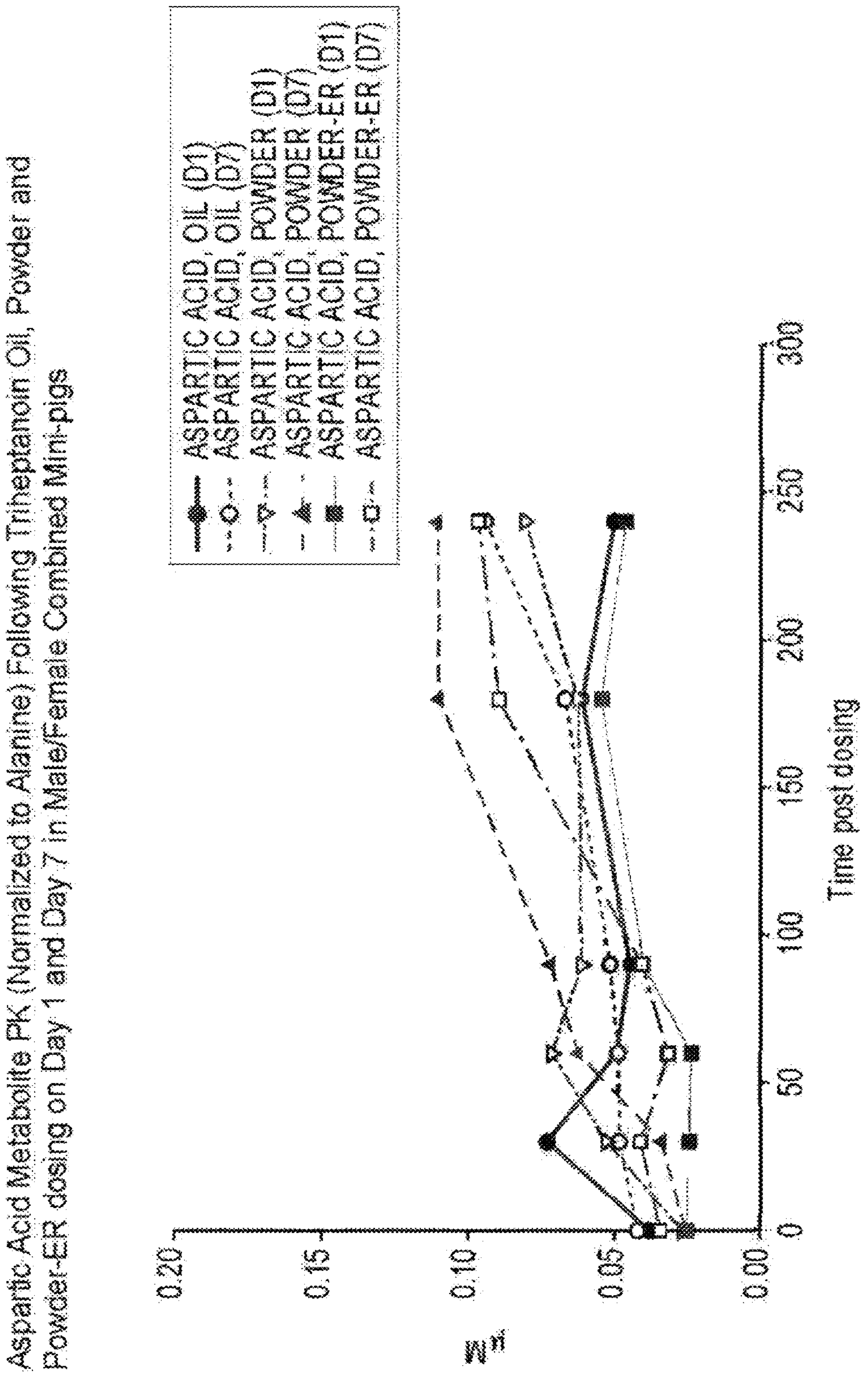
FIG. 25 is the metabolite PK profile of aspartic acid following triheptanoin oil, powder and powder-ER dosing on Day 1 and Day 7 in male and female mini-pigs combined.
Figure 26:
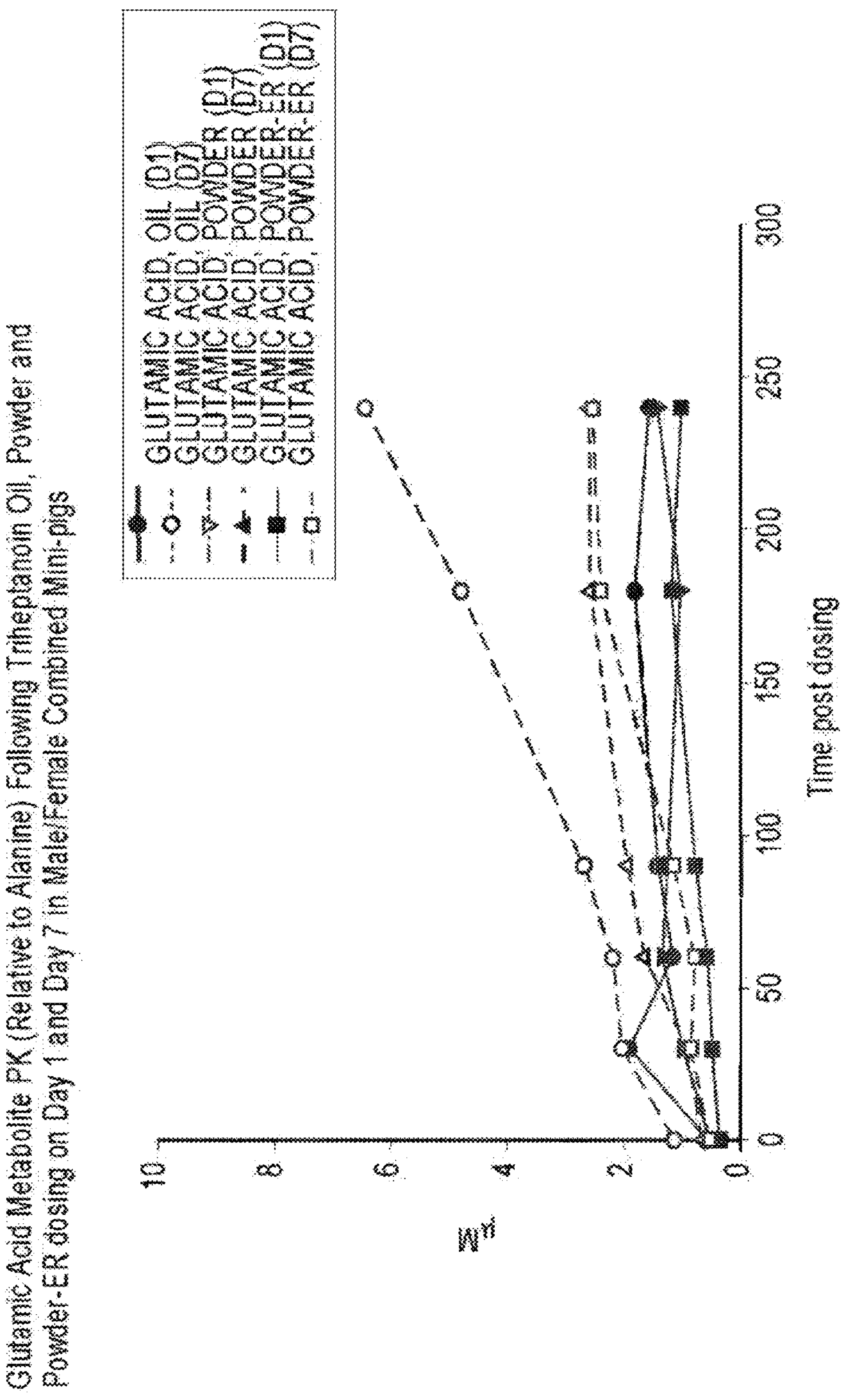
FIG. 26 is the metabolite PK profile of glutamic acid following triheptanoin oil, powder and powder-ER dosing on Day 1 and Day 7 in male and female mini-pigs combined.

Referring to FIGS. 25 and 26, we observed glutamic acid and aspartic acid increased and the Powder had higher levels of both metabolites than the powder ER. Glutamic acid and aspartic acid are gluconeogenic amino acids, and can represent a novel source of energy.

Figure 27:
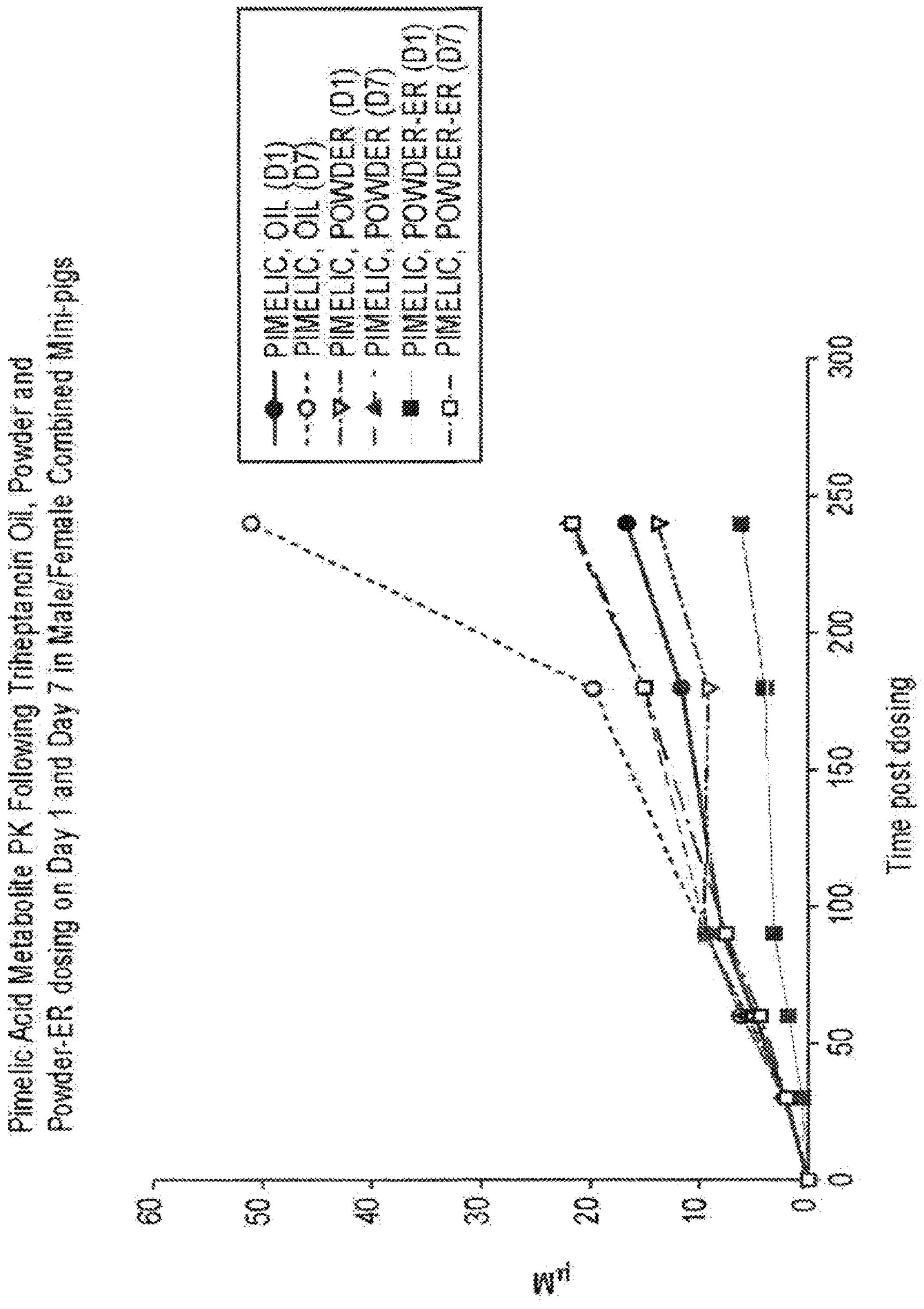
FIG. 27 is the metabolite PK profile of pimelic acid following triheptanoin oil, powder and powder-ER dosing on Day 1 and Day 7 in male and female mini-pigs combined.
Figure 28:
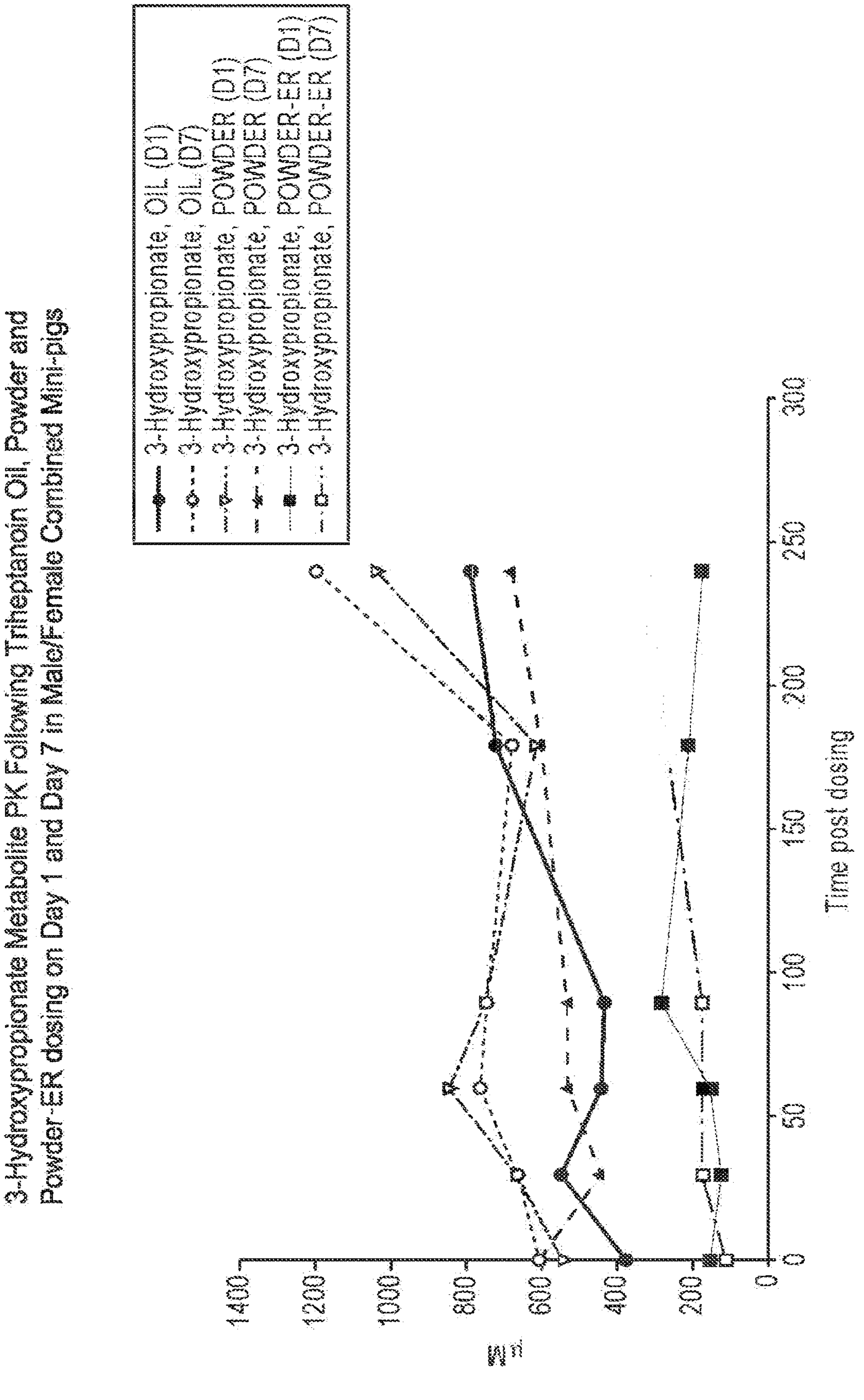
FIG. 28 is the metabolite PK profile of 3-hydroxypropionate following triheptanoin oil, powder and powder-ER dosing on Day 1 and Day 7 in male and female mini-pigs combined.
Figure 29:
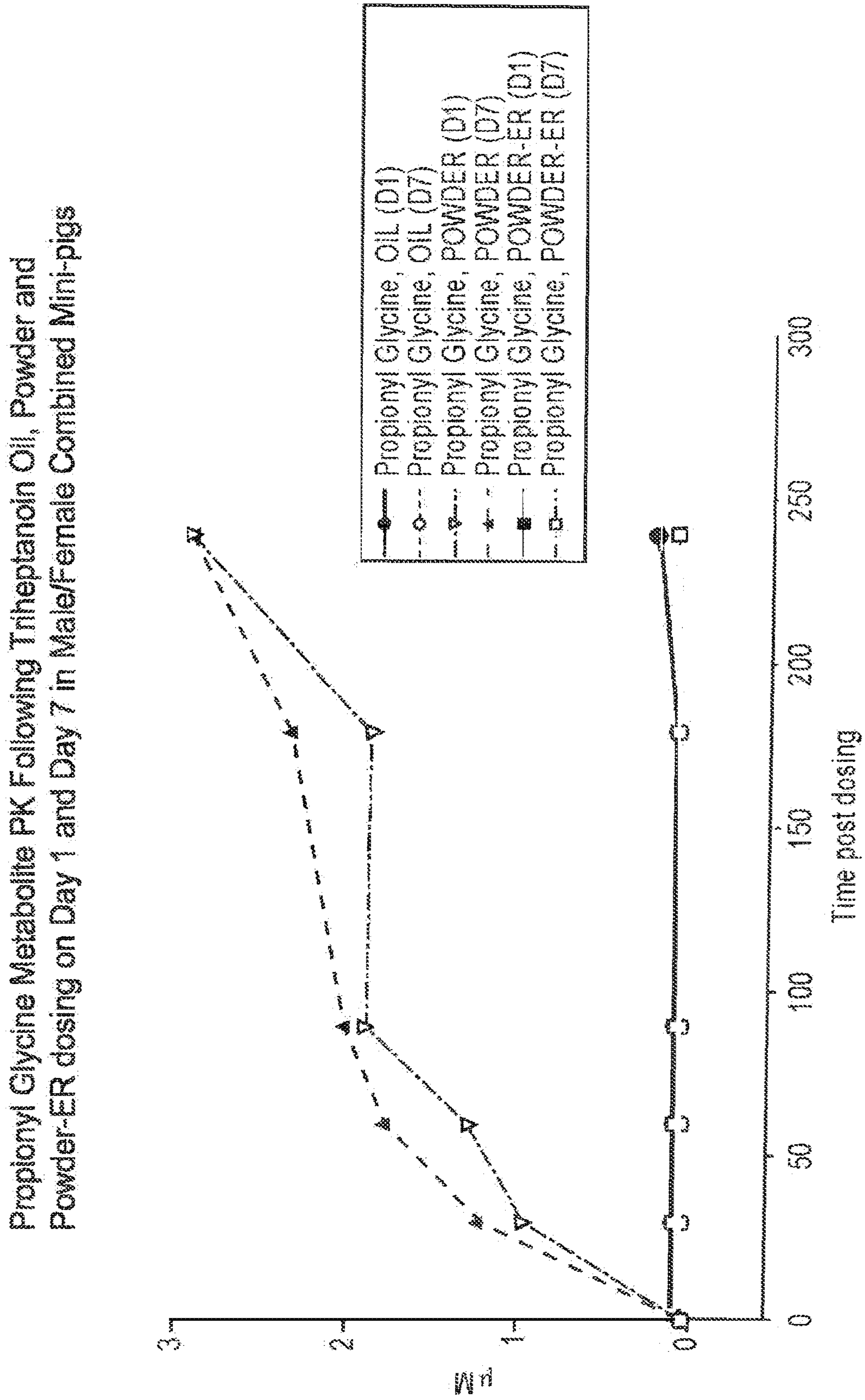
FIG. 29 is the metabolite PK profile of propionyl glycine following triheptanoin oil, powder and powder-ER dosing on Day 1 and Day 7 in male and female mini-pigs combined.

FIGS. 27-29 shows PK profiles of additional metabolites: A) pimelic acid, B) 3-hydroxypropionate, and C) propionylglycine following dosing on Day 1 and Day 7. The oil had the highest amount of pimelic acid compared to the powders. 3-Hydroxypropionate was increasing in all 3 groups but the powder-ER had the smallest increase and the lowest levels. Propionylglycine was essentially zero for the oil and the powder-ER but the powder dosing caused an increase. Overall, the Powder ER produced the least amount of excess metabolites.

Figure 30:
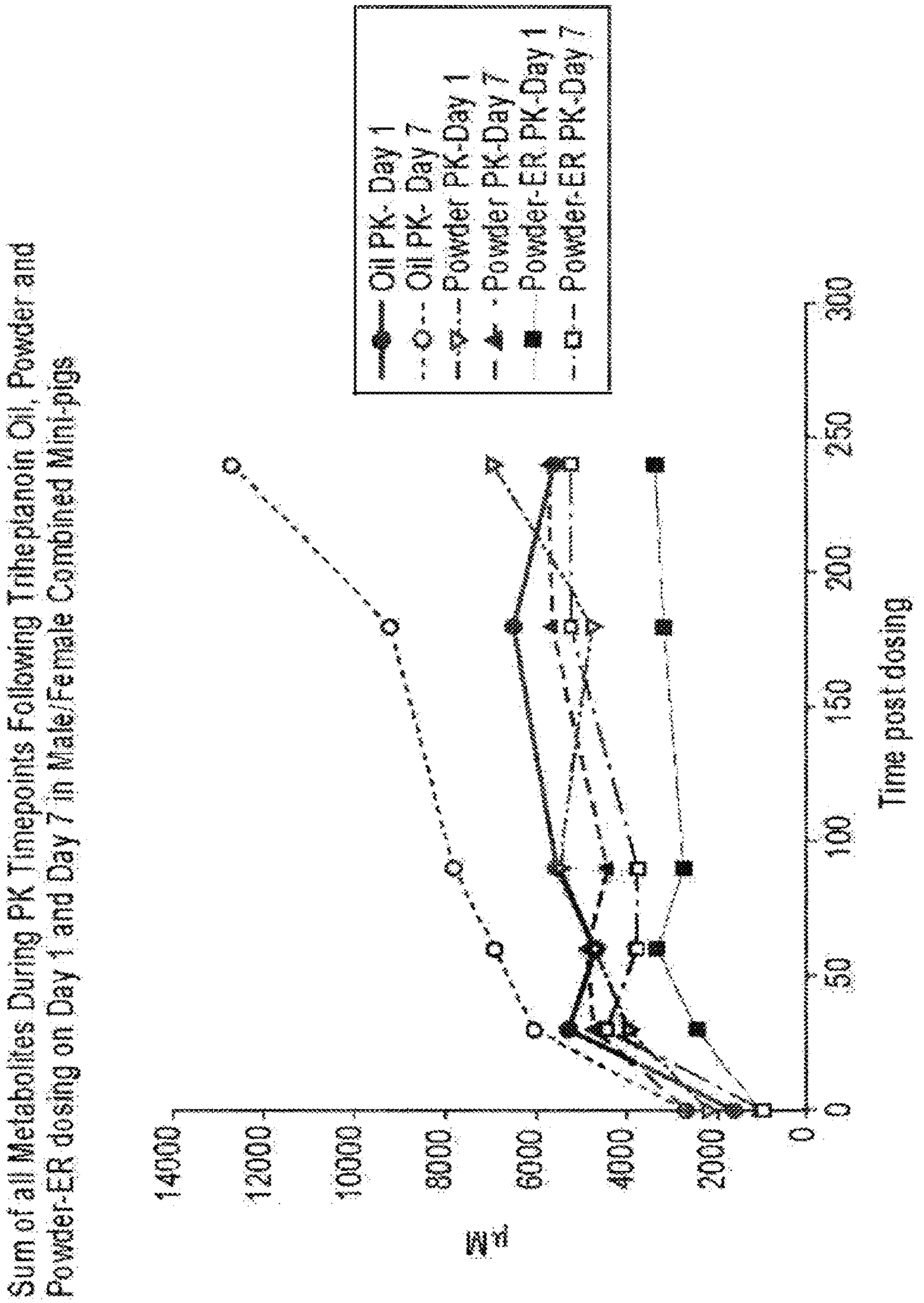
FIG. 30 is the sum of all metabolite PK profiles following triheptanoin oil, powder and powder-ER dosing on Day 1 and Day 7 in male and female mini-pigs combined.
Figure 31:
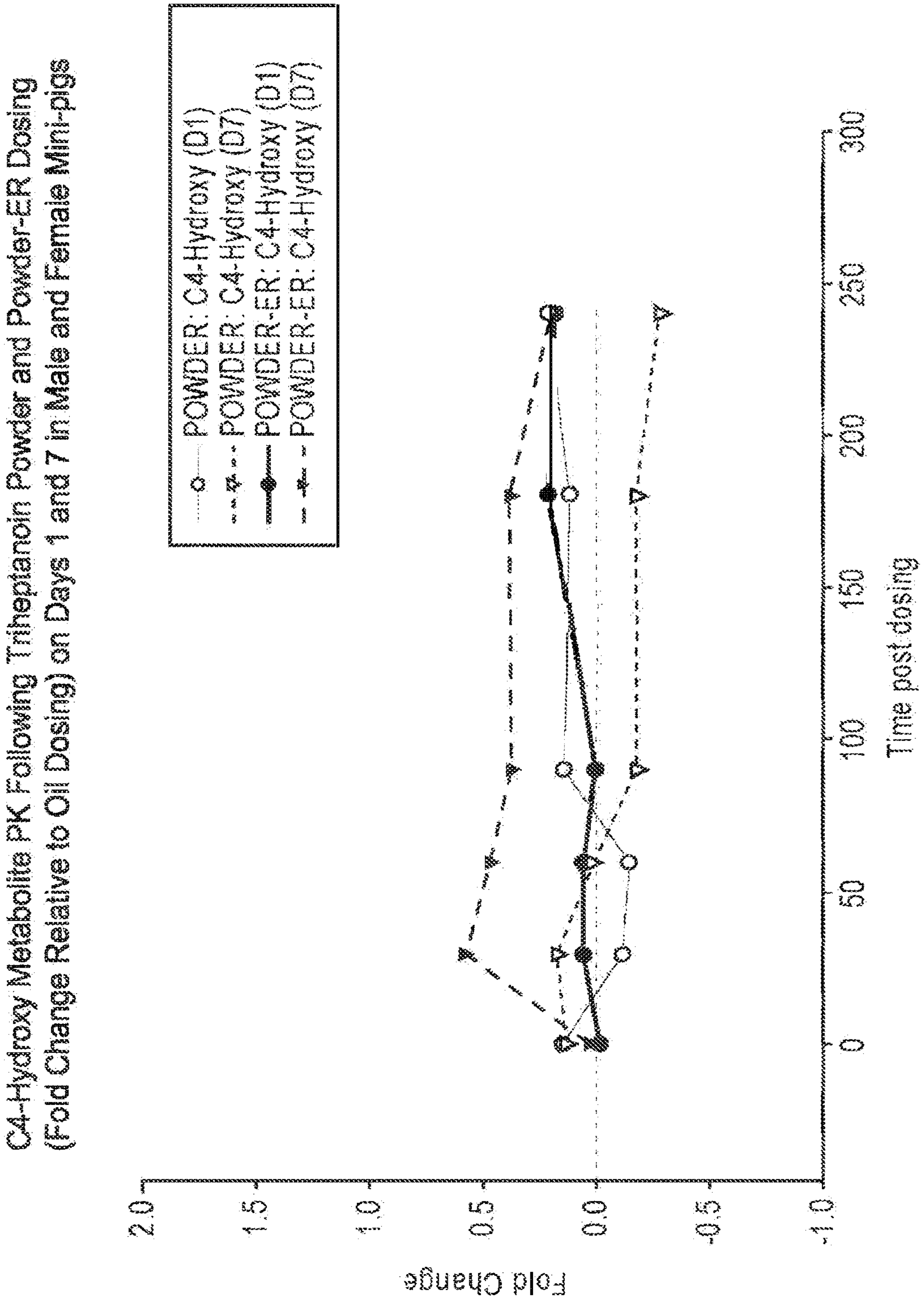
FIG. 31 is the metabolite PK profile of C4-hydroxy following triheptanoin powder and powder-ER dosing (fold change relative to the oil dosing) on Day 1 and Day 7 in male and female mini-pigs.
Figure 32:
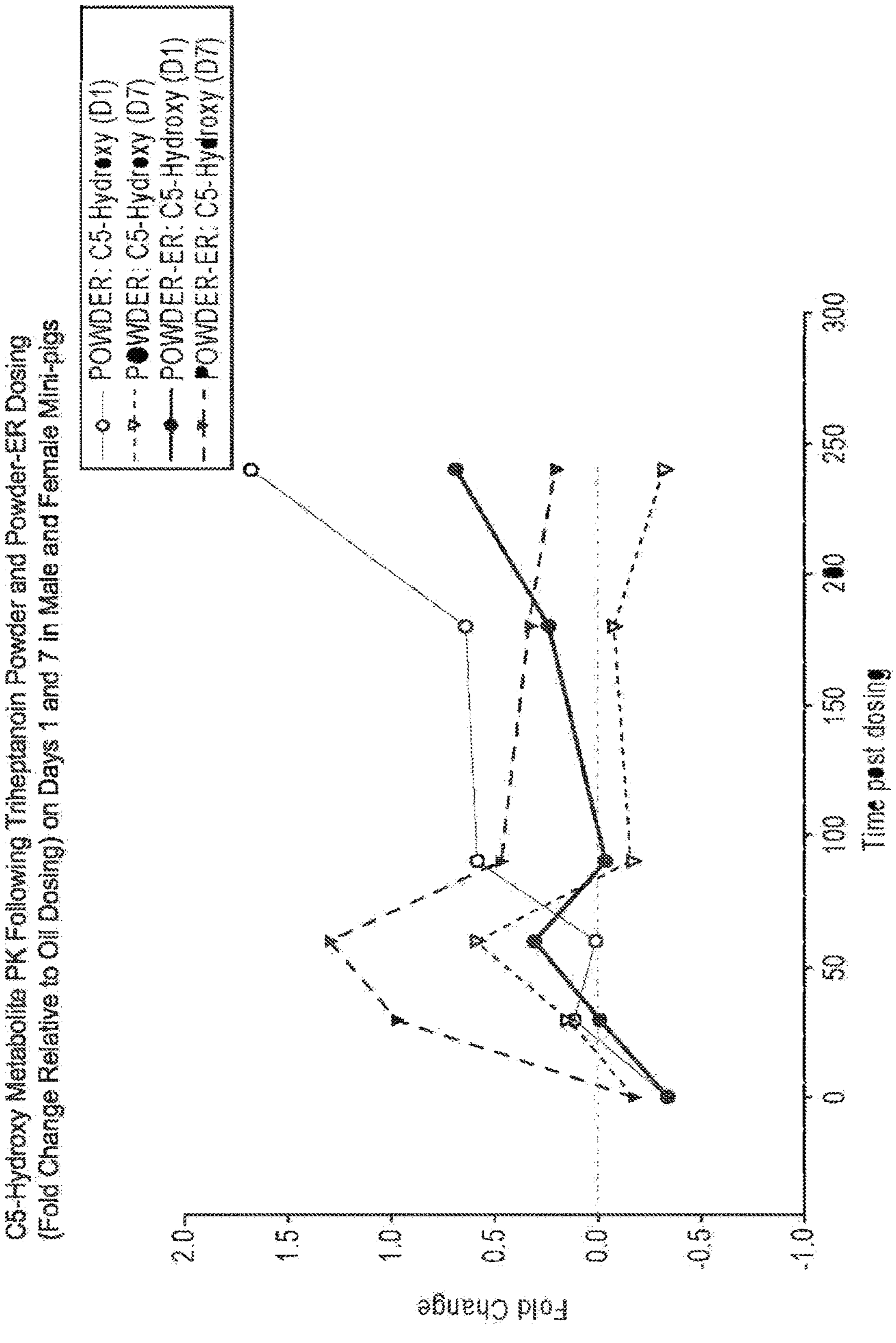
FIG. 32 is the metabolite PK profile of C5-hydroxy following triheptanoin powder and powder-ER dosing (fold change relative to the oil dosing) on Day 1 and Day 7 in male and female mini-pigs.
Figure 33:
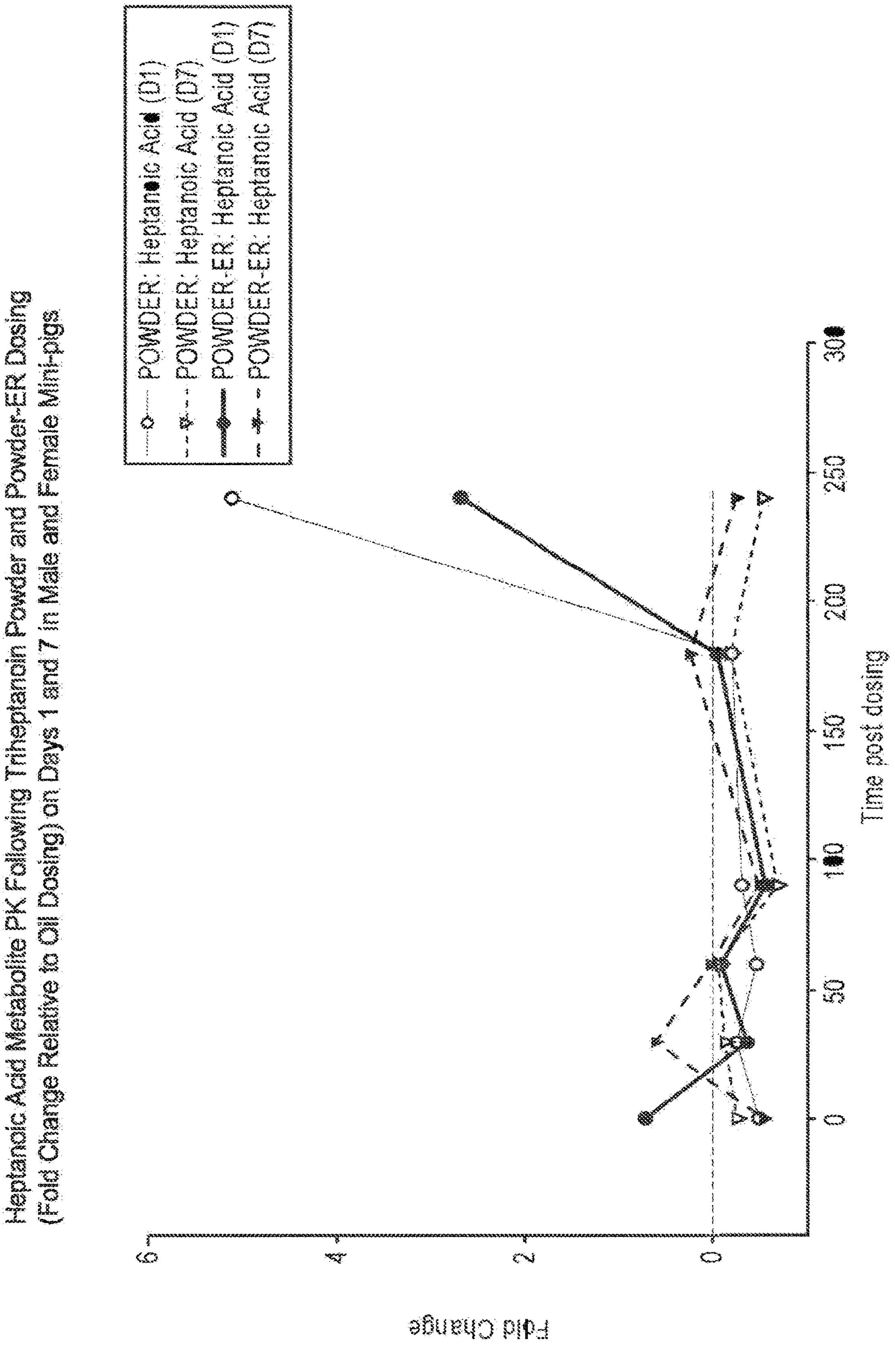
FIG. 33 is the metabolite PK profile of heptanoic acid following triheptanoin powder and powder-ER dosing (fold change relative to the oil dosing) on Day 1 and Day 7 in male and female mini-pigs.
Figure 34:
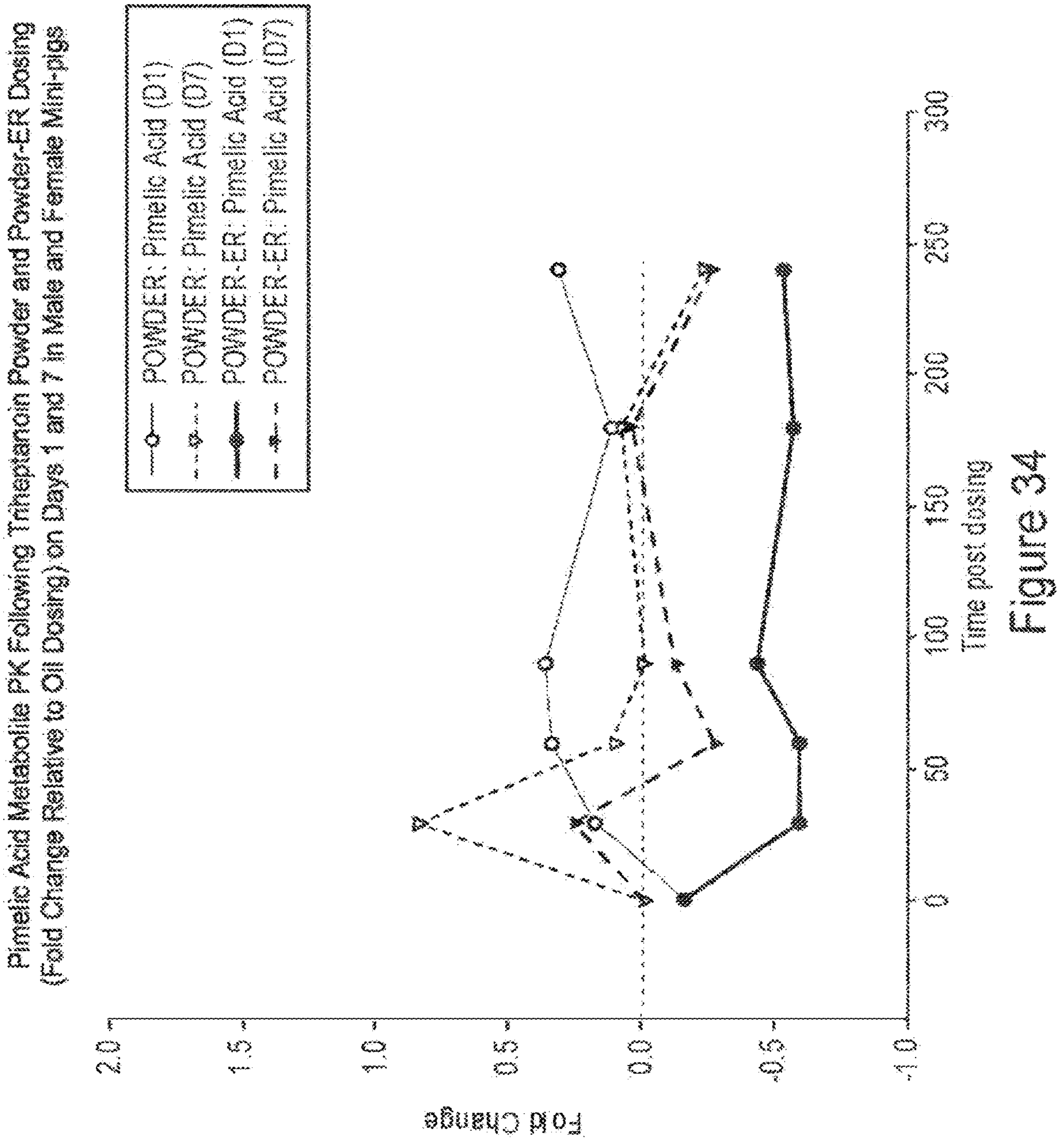
FIG. 34 is the metabolite PK profile of pimelic acid following triheptanoin powder and powder-ER dosing (fold change relative to the oil dosing) on Day 1 and Day 7 in male and female mini-pigs.
Figure 35:
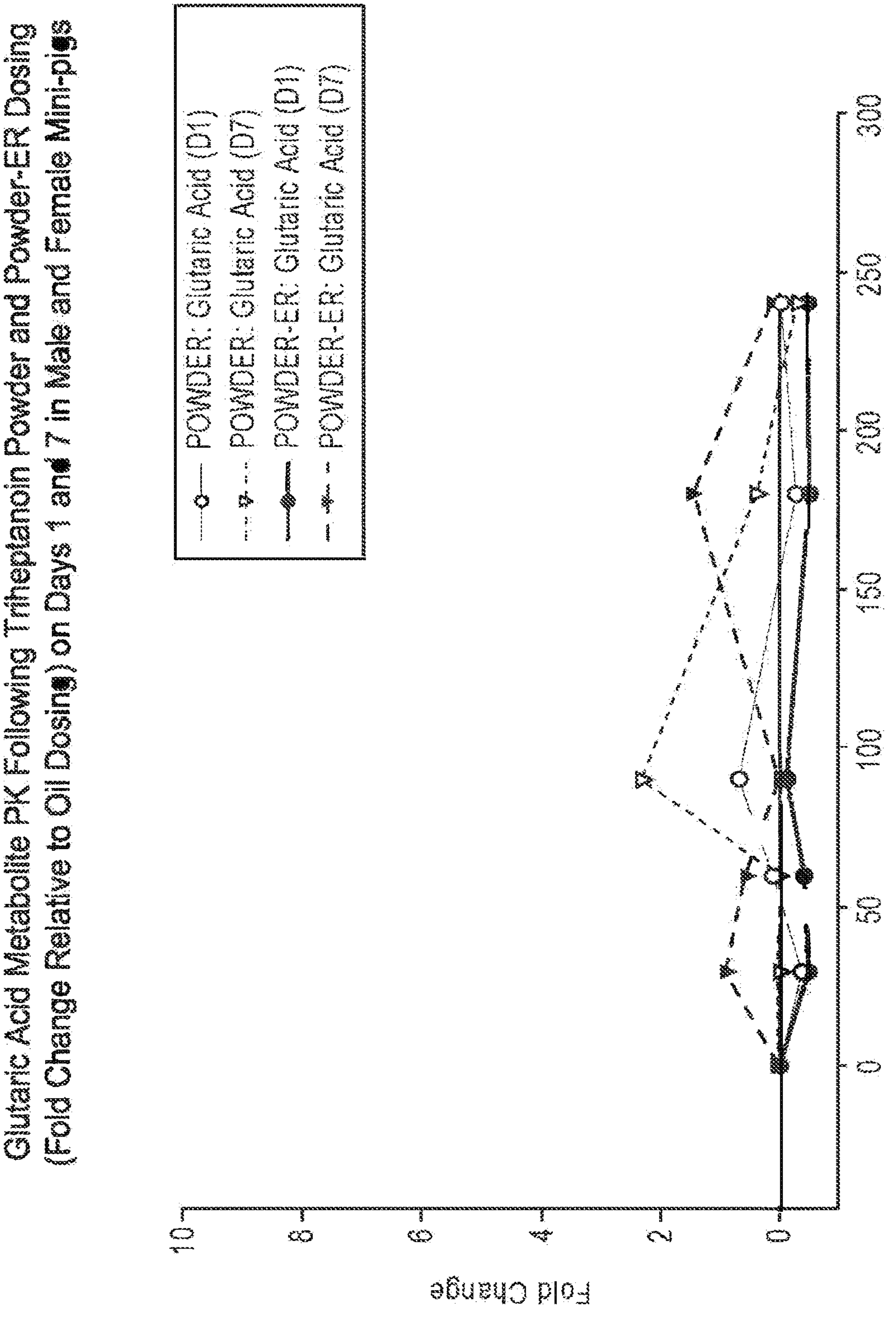
FIG. 35 is the metabolite PK profile of glutaric acid following triheptanoin powder and powder-ER dosing (fold change relative to the oil dosing) on Day 1 and Day 7 in male and female mini-pigs.
Figure 36:
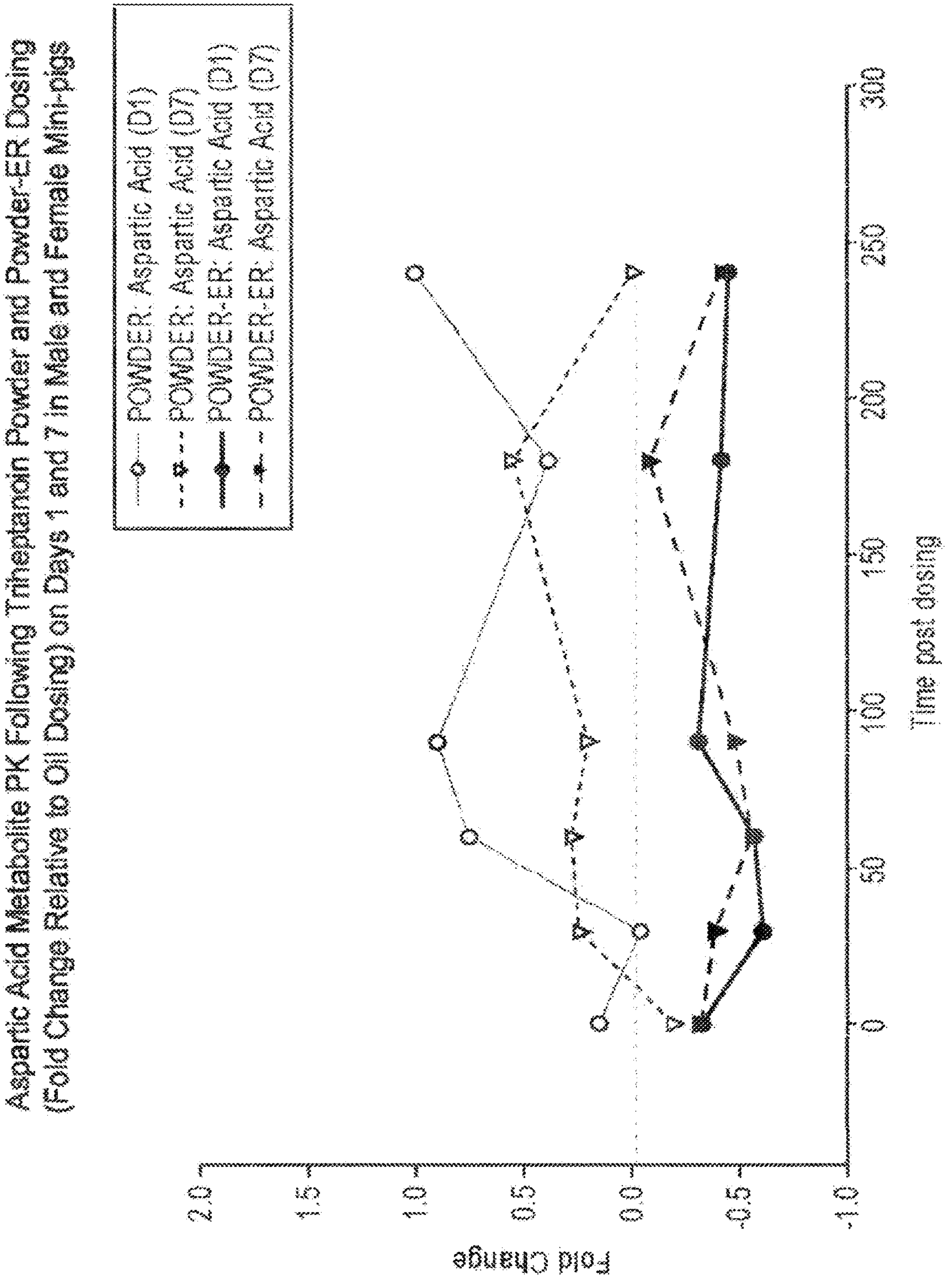
FIG. 36 is the metabolite PK profile of aspartic acid following triheptanoin powder and powder-ER dosing (fold change relative to the oil dosing) on Day 1 and Day 7 in male and female mini-pigs.
Figure 37:
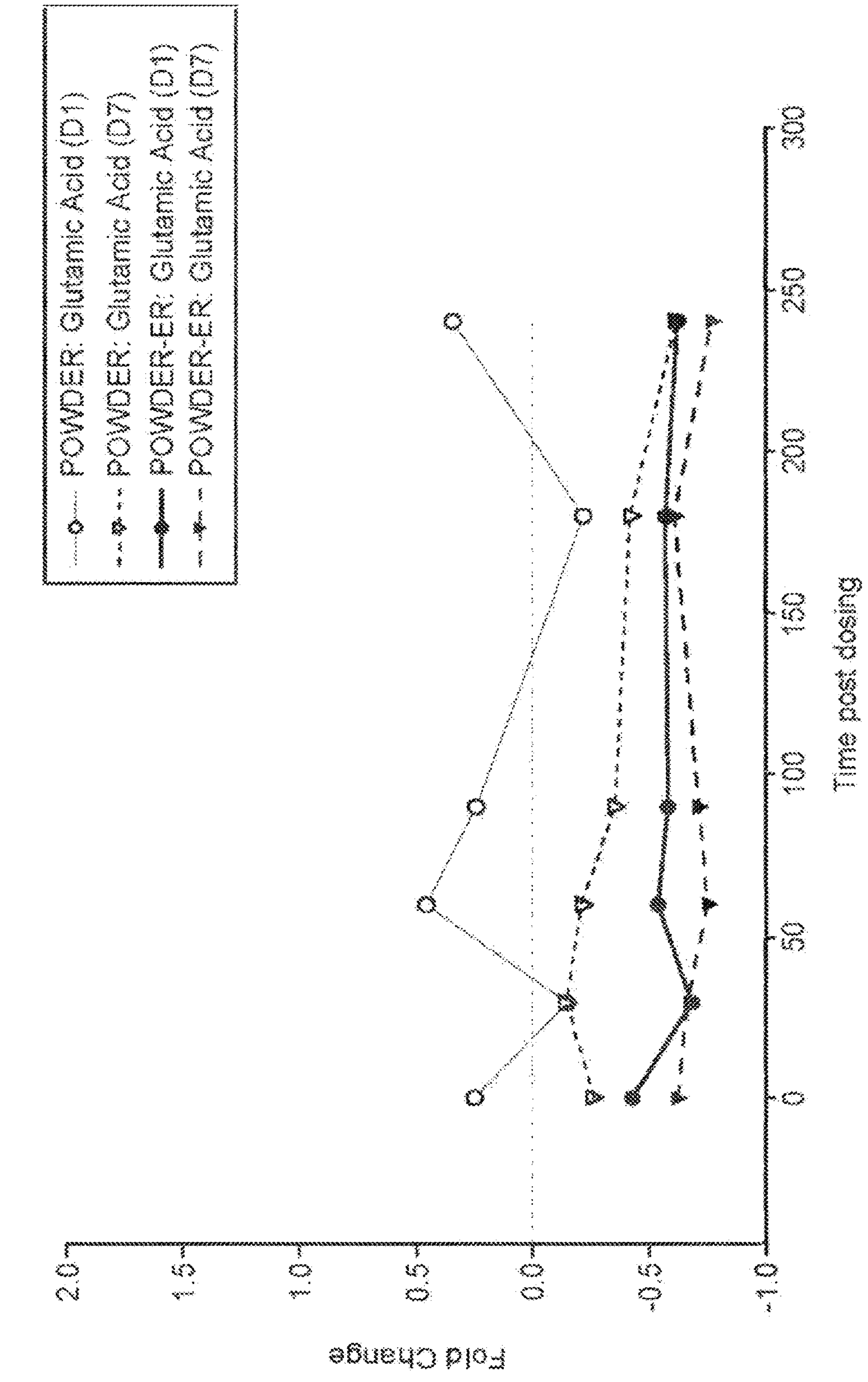
FIG. 37 is the metabolite PK profile of glutamic acid following triheptanoin powder and powder-ER dosing (fold change relative to the oil dosing) on Day 1 and Day 7 in male and female mini-pigs.
Figure 38:
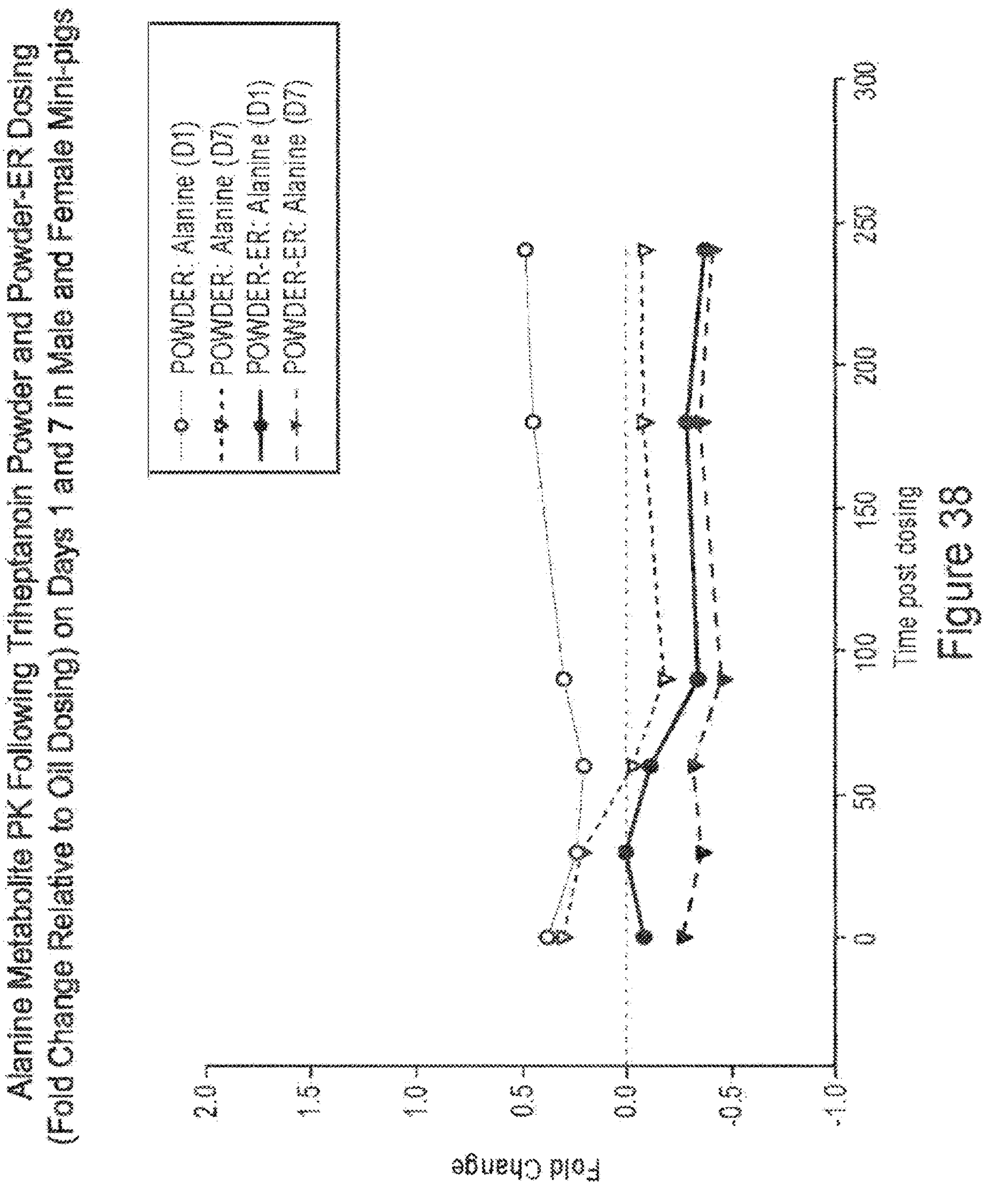
FIG. 38 is the metabolite PK profile of alanine following triheptanoin powder and powder-ER dosing (fold change relative to the oil dosing) on Day 1 and Day 7 in male and female mini-pigs.
Figure 39:
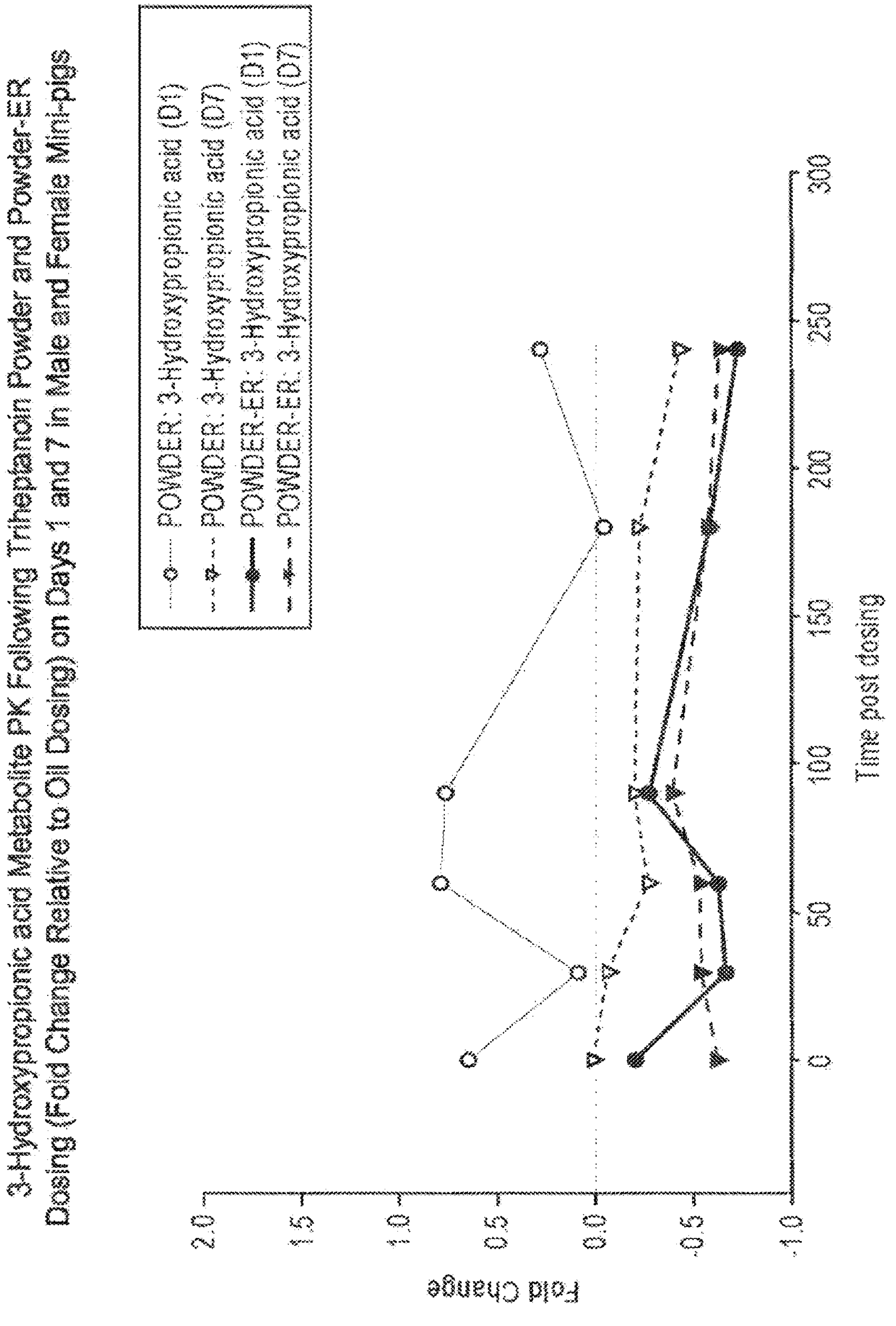
FIG. 39 is the metabolite PK profile of 3-hydroxypropionate following triheptanoin powder and powder-ER dosing (fold change relative to the oil dosing) on Day 1 and Day 7 in male and female mini-pigs.
Figure 40:
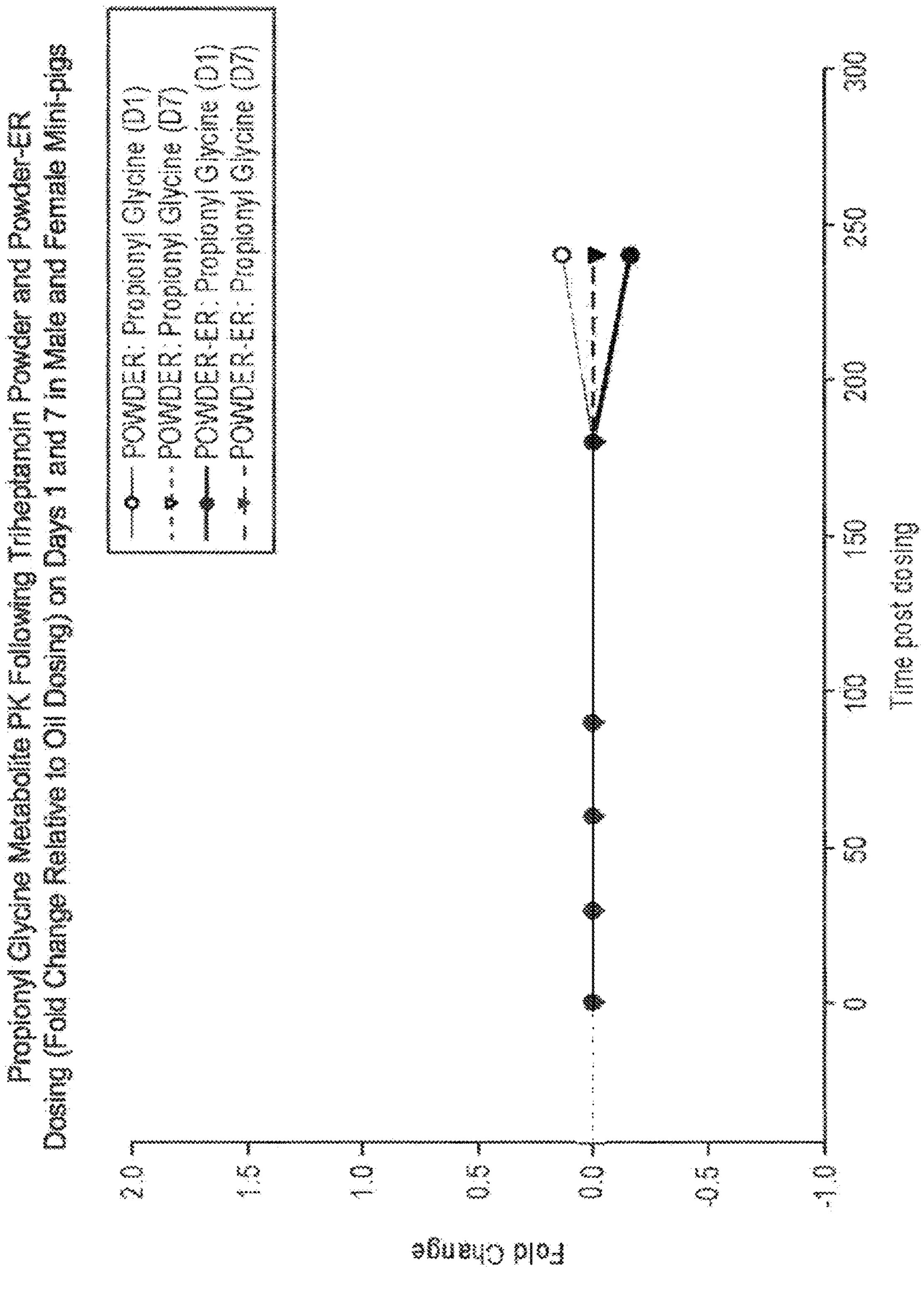
FIG. 40 is the metabolite PK profile of propionyl glycine following triheptanoin powder and powder-ER dosing (fold change relative to the oil dosing) on Day 1 and Day 7 in male and female mini-pigs.

The PK profiles of all metabolites are shown in FIG. 30. The metabolites include Triheptanoin, C4 (Hydroxy and Keto), C5 (Hydroxy and Keto), Heptanoic acid, Pimelic acid, Glutaric acid, Aspartic acid, Glutamic acid, Alanine and 3-Hydroxypropionic acid.

The results of the powder and the powder-ER as compared to that of the oil are shown in FIGS. 31-40. The Powder ER raised the C5-hydroxy levels the most of all the treatments, which indicates it's the most effective at delivering fatty acids to the cells. We observed differences between Days 1 and Day 7 for the powders. Day 7 levels were lower than Day 1, spike at 240 min on Day 1, which indicates that PK sampling can be carried out longer. The Powder-ER dosing resulted in lowest levels of pimelic acid. The Powder had a higher release of aspartic acid than the Powder-ER. The Powder had higher levels of glutamic acid and alanine than the Powder-ER. The Powder also had higher levels of 3-Hydroxypropionate than the Powder-ER.

Following long-standing patent law convention, the terms "a", "an", and "the" refer to "one or more" when used in this application, including the claims.

The use of the term "or" in the claims is used to mean "and/or" unless explicitly indicated to refer to alternatives only or the alternatives are mutually exclusive. It is specifically contemplated that any listing of items using the term "or" means that any of those listed items may also be specifically excluded from the related embodiment.

Throughout this application, the term "about" is used to indicate that a value includes the standard deviation of error for the device or method being employed to determine the value.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

The patents listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings.

What is claimed is:

1. A method for treating a fatty acid oxidation disorder in a human in need thereof, the method comprising:

orally administering to the human a liquid pharmaceutical composition comprising an active ingredient, diheptanoate, and hexano-diheptanoate, wherein the active ingredient is triheptanoin oil;

wherein the triheptanoin oil has a purity greater than 98%;

wherein glycerol is undetectable in the composition;

wherein the composition comprises no more than 0.2% water by weight;

wherein the composition comprises 0.01% to 1.0% hexano-diheptanoate by weight;

wherein the composition comprises 0.01% to 1.5% diheptanoate by weight; and wherein the composition has an assay value of triheptanoin between 95% to 103% as measured by Ph. Eur. 2.2.28.

2. The method of claim 1, wherein the fatty acid oxidation disorder is a deficiency in carnitine palmitoyl transferase I, carnitine acylcarnitine translocase, carnitine palmitoyl transferase II, very long chain acyl-CoA dehydrogenase, trifunctional protein, or long chain hydroxyacyl-CoA dehydrogenase.

3. The method of claim 1, wherein the composition is used as a source of calories.

4. The method of claim 1, wherein the composition comprises 0.01% to 0.7% diheptanoate by weight.

5. The method of claim 1, wherein the composition comprises less than 0.5% monoheptanoate by weight.

6. The method of claim 1, wherein monoheptanoate is undetectable in the composition.

7. The method of claim 1, wherein each individual unidentified impurity in the composition is less than 0.5% by weight.

8. The method of claim 1, wherein the triheptanoin oil has a purity greater than 98% after the composition is stored at room temperature and protected from light for 24 months.

9. The method of claim 1, wherein the triheptanoin oil has a purity greater than 98.5%.

* * * * *